(12) United States Patent
Allen et al.

(10) Patent No.: US 7,057,049 B2
(45) Date of Patent: *Jun. 6, 2006

(54) PROCESS FOR MAKING SUBSTITUTED PYRAZOLES

(75) Inventors: Kimberley C. Allen, Chicago, IL (US); Dennis K. Anderson, St. Charles, MO (US); John E. Baldus, St. Louis, MO (US); Todd Boehlow, Chesterfield, MO (US); Jerry D. Clark, Alton, IL (US); Dan R. Dukesherer, St. Louis, MO (US); Albert D. Edney, St. Peters, MO (US); Tom Fevig, Wildwood, MO (US); Sastry Kunda, St. Louis, MO (US); Jon P. Lawson, Glencoe, MO (US); Patrick H. Lau, Chesterfield, MO (US); Lisa L. McDermott, Sullivan, MO (US); Michael K. Mao, Chesterfield, MO (US); Jodi L. Moe, Buffalo Grove, IL (US); Partha Mudipalli, Skokie, IL (US); Win Naing, Chesterfield, MO (US); Shaun R. Selness, Chesterfield, MO (US); Christine B. Seymour, Glenview, IL (US); Tobin C. Schilke, St. Louis, MO (US); Shekhar Viswanath, Maryland Heights, MO (US); John K. Walker, Maryland Heights, MO (US); Gopichand Yalamanchili, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 235 days.

This patent is subject to a terminal disclaimer.

(21) Appl. No.: 10/406,150

(22) Filed: Apr. 1, 2003

(65) Prior Publication Data

US 2003/0225108 A1 Dec. 4, 2003

Related U.S. Application Data

(63) Continuation-in-part of application No. 10/254,445, filed on Sep. 25, 2002, now Pat. No. 6,897,318.

(60) Provisional application No. 60/383,691, filed on May 28, 2002, provisional application No. 60/381,261, filed on May 17, 2002, provisional application No. 60/324,987, filed on Sep. 25, 2001.

(51) Int. Cl.
*C07D 231/12* (2006.01)
*C07D 211/06* (2006.01)
*C07D 211/16* (2006.01)

(52) U.S. Cl. ............... 546/192; 548/364.1; 544/179; 544/180; 544/182; 544/238; 544/333; 544/405

(58) Field of Classification Search ........... 546/192; 548/364.1
See application file for complete search history.

(56) References Cited

U.S. PATENT DOCUMENTS

| | | | |
|---|---|---|---|
| 3,254,093 A | 5/1966 | Huisgen et al. | 260/295 |
| 3,984,431 A | 10/1976 | Guérémy et al. | 260/310 R |
| 4,000,281 A | 12/1976 | Beiler et al. | 424/263 |
| 5,134,142 A | 7/1992 | Matsuo et al. | 514/255 |
| 5,559,137 A | 9/1996 | Adams et al. | 514/341 |
| 5,569,769 A | 10/1996 | Merkle et al. | 548/373.1 |
| 5,589,439 A | 12/1996 | Goto et al. | 504/261 |
| 6,143,892 A | 11/2000 | Graneto et al. | 544/364 |
| 6,271,253 B1 | 8/2001 | Carter et al. | 514/432 |
| 6,423,713 B1 * | 7/2002 | Anantanarayan et al. | 514/235.8 |
| 6,514,977 B1 | 2/2003 | Anantanarayan et al. | 514/254.01 |
| 6,525,059 B1 | 2/2003 | Anantanarayan et al. | 514/256 |
| 6,617,324 B1 | 9/2003 | Naraian et al. | 514/235.8 |

FOREIGN PATENT DOCUMENTS

| | | |
|---|---|---|
| EP | 0 115 640 | 8/1984 |
| EP | 0 515 041 | 11/1992 |
| JP | 4-145081 | 5/1992 |
| JP | 5-17470 | 1/1993 |
| JP | 5-345772 | 12/1993 |
| WO | WO 83/00330 | 2/1983 |

(Continued)

OTHER PUBLICATIONS

U.S. Appl. No. 10/021,780, filed Dec. 7, 2001, Anantanarayan et al.

(Continued)

*Primary Examiner*—Venkataraman Balasubramanian
(74) *Attorney, Agent, or Firm*—Julie M. Lappin; Charles Ashbrook

(57) ABSTRACT

This invention is directed generally to a process for making substituted pyrazoles, tautomers of the substituted pyrazoles, and salts of the substituted pyrazoles and tautomers. The substituted pyrazoles correspond in structure to Formula (I):

wherein $R^{3A}$, $R^{3B}$, $R^{3C}$, $Y^1$, $Y^2$, $Y^3$, $Y^4$, and $Y^5$ are as defined in the specification.

8 Claims, No Drawings

FOREIGN PATENT DOCUMENTS

| | | |
|---|---|---|
| WO | WO 92/19615 | 11/1992 |
| WO | WO 95/06036 | 3/1995 |
| WO | WO 96/03385 | 2/1996 |
| WO | WO 97/01551 | 1/1997 |
| WO | WO 98/52937 | 11/1998 |
| WO | WO 98/52940 | 11/1998 |
| WO | WO 98/52941 | 11/1998 |
| WO | WO 99/58523 | 11/1999 |
| WO | WO 00/31063 | 6/2000 |
| WO | WO 00/31072 | 6/2000 |
| WO | WO 03/026663 | 4/2003 |

OTHER PUBLICATIONS

U.S. Appl. No. 10/114,297, filed Apr. 2, 2002, Naraian et al.

U.S. Appl. No. 10/374,781, filed Feb. 25, 2003, Naraian et al.

De Laszlo, S.E., et al., *Pyrroles and other heterocycles as inhibitors of p38 kinase*, Bioorg. Med. Chem. Lett., 8:2689-2694 (1998).

Dean, E.W. et al., *A convenient method for the determination of water in petroleum and other organic emulsions*, J. Indus. Eng. Chem., 12(5):486-90 (1920).

Schurig, V., et al., *Kinetic resolution of aliphatic oxiranes mediated by in situ formed molybdenum(VI) (oxo-diperoxo) hydroxy acid amide/chiral diol complexes*, Bull. Soc. Chim. Fr., 131:555-560 (1994).

U.S. Appl. No. 09/083,670, filed Apr. 22, 1998, Anantanarayan et al.

U.S. Appl. No. 09/512,696, filed Feb. 24, 2000, Anantanarayan et al.

U.S. Appl. No. 10/456,933, filed Jun. 5, 2003, Benson et al.

\* cited by examiner

PROCESS FOR MAKING SUBSTITUTED PYRAZOLES

CROSS-REFERENCE TO RELATED PATENT APPLICATIONS

This patent application which is a continuation-in-part, claims priority to U.S. patent application Ser. No. 10/254,445 filed Sep. 25, 2002, now U.S. Pat. No. 6,897,318, which in turn claims priority to U.S. Provisional Application Ser. Nos. 60/383,691, (filed May 28, 2002), 60/381,261 (filed May 17, 2002), and 60/324,987 (filed Sep. 25, 2001). The entire text of each of the above applications is incorporated by reference into this application.

FIELD OF THE INVENTION

This invention is directed to a process for making substituted pyrazoles, including tautomers of the substituted pyrazoles, and salts of the substituted pyrazoles and tautomers. This invention also is directed to compositions (including methods for making such compositions) comprising compounds that may be used as intermediates in such a process. This invention is additionally directed to pharmaceutical compositions (including methods for making such compositions) comprising substituted pyrazoles, tautomers, and pharmaceutically-acceptable salts prepared by such a process. This invention is further directed to using compounds, tautomers, and pharmaceutically-acceptable salts prepared by such a process to treat various conditions.

BACKGROUND OF THE INVENTION

Mitogen-activated protein kinases (MAP) is a family of proline-directed serine/threonine kinases that activate their substrates by dual phosphorylation. The kinases are activated by a variety of signals, including nutritional and osmotic stress, UV light, growth factors, endotoxin, and inflammatory cytokines. The p38 MAP kinase group is a MAP family of various isoforms, including p38α, p38β, and p38γ. These kinases are responsible for phosphorylating and activating transcription factors (e.g., ATF2, CHOP, and MEF2C), as well as other kinases (e.g., MAPKAP-2 and MAPKAP-3). The p38 isoforms are activated by bacterial lipopolysaccharide, physical and chemical stress, and pro-inflammatory cytokines, including tumor necrosis factor ("TNF") and interleukin-1 ("IL-1"). The products of the p38 phosphorylation mediate the production of inflammatory cytokines, including TNF, IL-1, and cyclooxygenase-2.

It is believed that p38α kinase can cause or contribute to the effects of, for example, inflammation generally; arthritis; neuroinflammation; pain; fever; pulmonary disorders; cardiovascular diseases; cardiomyopathy; stroke; ischemia; reperfusion injury; renal reperfusion injury; brain edema; neurotrauma and brain trauma; neurodegenerative disorders; central nervous system disorders; liver disease and nephritis; gastrointestinal conditions; ulcerative diseases; ophthalmic diseases; ophthalmological conditions; glaucoma; acute injury to the eye tissue and ocular traumas; diabetes; diabetic nephropathy; skin-related conditions; viral and bacterial infections; myalgias due to infection; influenza; endotoxic shock; toxic shock syndrome; autoimmune disease; bone resorption diseases; multiple sclerosis; disorders of the female reproductive system; pathological (but non-malignant) conditions, such as hemaginomas, angiofibroma of the nasopharynx, and avascular necrosis of bone; benign and malignant tumors/neoplasia including cancer; leukemia; lymphoma; systemic lupus erthrematosis (SLE); angiogenesis including neoplasia; and metastasis.

TNF is a cytokine produced primarily by activated monocytes and macrophages. Excessive or unregulated TNF production (particularly TNF-α) has been implicated in mediating a number of diseases. It is believed, for example, that TNF can cause or contribute to the effects of inflammation (e.g., rheumatoid arthritis and inflammatory bowel disease), asthma, autoimmune disease, graft rejection, multiple sclerosis, fibrotic diseases, cancer, fever, psoriasis, cardiovascular diseases (e.g., post-ischemic reperfusion injury and congestive heart failure), pulmonary diseases (e.g., hyperoxic alveolar injury), hemorrhage, coagulation, radiation damage, and acute phase responses like those seen with infections and sepsis and during shock (e.g., septic shock and hemodynamic shock). Chronic release of active TNF can cause cachexia and anorexia. And TNF can be lethal.

TNF also has been implicated in infectious diseases. These include, for example, malaria, mycobacterial infection, meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

IL-8 is another pro-inflammatory cytokine, which is produced by mononuclear cells, fibroblasts, endothelial cells, and keratinocytes. This cytokine is associated with conditions including inflammation.

IL-1 is produced by activated monocytes and macrophages, and is involved in inflammatory responses. IL-1 plays a role in many pathophysiological responses, including rheumatoid arthritis, fever, and reduction of bone resorption.

TNF, IL-1, and IL-8 affect a wide variety of cells and tissues, and are important inflammatory mediators of a wide variety of conditions. The inhibition of these cytokines by inhibition of the p38 kinase is beneficial in controlling, reducing, and alleviating many of these disease states.

Various pyrazoles have previously been described:

In U.S. Pat. No. 4,000,281, Beiler and Binon report 4,5-aryl/heteroaryl substituted pyrazoles with antiviral activity against both RNA and DNA viruses, such as myxoviruses, adenoviruses, rhinoviruses, and various viruses of the herpes group.

WIPO Int'l Publ. No. WO 92/19615 (published Nov. 12, 1992) describes pyrazoles as novel fungicides.

In U.S. Pat. No. 3,984,431, Cueremy and Renault report derivatives of pyrazole-5-acetic acid as having anti-inflammatory activity, with [1-isobutyl-3,4-diphenyl-1H-pyrazol-5-yl]acetic acid being specifically described.

In U.S. Pat. No. 3,254,093, Huisgen et al. report a process for preparing pyrazoles.

WIPO Int'l Publ. No. WO 83/00330 (published Feb. 3, 1983) describes a process for preparing diphenyl-3,4-methyl-5-pyrazole derivatives.

WIPO Int'l Publ. No. WO 95/06036 (published Mar. 2, 1995 reports a process for preparing pyrazole derivatives.

In U.S. Pat. No. 5,589,439, T. Goto, et al. report tetrazole derivatives and their use as herbicides.

EP 515,041 reports pyrimidinyl substituted pyrazole derivatives as novel agricultural fungicides.

Japanese Patent 4,145,081 reports pyrazolecarboxylic acid derivatives as herbicides.

Japanese Patent 5,345,772 reports novel pyrazole derivatives as inhibiting acetylcholinesterase.

Pyrazoles have been reported as useful in treating inflammation.

Japanese Patent 5,017,470 reports synthesis of pyrazole derivatives as anti-inflammatory, anti-rheumatic, anti-bacterial, and anti-viral drugs.

EP 115640 (published Dec. 30, 1983) reports 4-imidazolyl-pyrazole derivatives as inhibitors of thromboxane synthesis, with 3-(4-Isopropyl-1-methylcyclohex-1-yl)-4-(imidazol-1-yl)-1H-pyrazole being specifically described.

WIPO Int'l Publ. No. WO 97/01551 (published Jan. 16, 1997) reports substituted pyrazoles as adenosine antagonists, with 4-(3-Oxo-2,3-dihydropyridazin-6-yl)-3-phenylpyrazole being specifically described.

In U.S. Pat. No. 5,134,142, to Matsuo et al. report 1,5-diaryl pyrazoles as having anti-inflammatory activity.

In U.S. Pat. No. 5,559,137, Adams et al. report pyrazoles (1,3,4,-substituted) as inhibitors of cytokines used in the treatment of cytokine diseases, with 3-(4-fluorophenyl)-1-(4-methylsulfinylphenyl)-4-(4-pyridyl)-5H-pyrazole being specifically described.

WIPO Int'l Publ. No. WO 96/03385 (published Feb. 8, 1996) reports 3,4-substituted pyrazoles as having anti-inflammatory activity, with 3-methylsulfonylphenyl-4-aryl-pyrazoles and 3-aminosulfonylphenyl-4-aryl-pyrazoles being specifically described.

Laszlo et al., *Bioorg. Med. Chem. Letters*, 8 (1998) 2689–2694, describes certain furans, pyrroles, and pyrazolones, particularly 3-pyridyl-2,5-diaryl-pyrroles, as inhibitors of p38 kinase.

WIPO Int'l Publ. No. WO 98/52940 (PCT Patent Application No. US98/10436 published on Nov. 26, 1998) reports pyrazoles, compositions containing those pyrazoles, and methods for treating p38-mediated disorders using those pyrazoles.

WIPO Int'l Publ. No. WO 00/31063 (PCT Patent Application No. US99/26007 published on Jun. 2, 2000) also reports pyrazoles, compositions containing those pyrazoles, and methods for making pyrazoles.

In view of the importance of pyrazoles in the prevention and treatment of several pathological conditions (particularly those associated with p38 kinase activity, TNF activity, and/or cyclooxygenase-2 activity), there continues to be a need for processes for making substituted pyrazoles. The following disclosure describes such a process.

SUMMARY OF THE INVENTION

This invention is directed to a method for making substituted pyrazoles that tend to inhibit p38 kinase activity, TNF activity, and/or cyclooxygenase-2 activity.

Briefly, therefore, this invention is directed, in part, to a process for making a substituted pyrazole, a tautomer of the substituted pyrazole, or a salt of the substituted pyrazole or tautomer. The substituted pyrazole corresponds in structure to Formula (I):

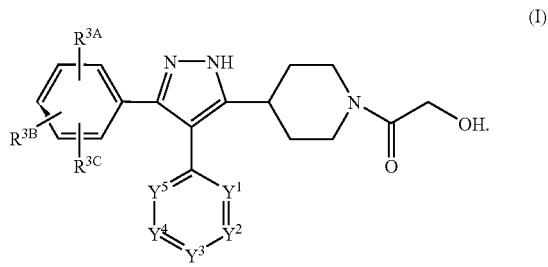

Here:

$R^{3A}$, $R^{3B}$, and $R^{3C}$ are independently selected from the group consisting of hydrogen, halogen, hydroxy, cyano, amino, alkyl, aminoalkyl, monoalkylamino, dialkylamino, alkoxy, and alkoxyalkyl. Any carbon of the alkyl, aminoalkyl, monoalkylamino, dialkylamino, alkoxy, or alkoxyalkyl optionally is substituted with one or more substituents independently selected from the group consisting of halogen, hydroxy, and cyano.

One of $Y^1$, $Y^2$, $Y^3$, $Y^4$, and $Y^5$ is $=C(R^4)-$. One of $Y^1$, $Y^2$, $Y^3$, $Y^4$, and $Y^5$ is $=N-$. And three of $Y^1$, $Y^2$, $Y^3$, $Y^4$, and $Y^5$ are independently selected from the group consisting of $=C(H)-$ and $=N-$.

$R^4$ is hydrogen, halogen, cyano, hydroxy, thiol, carboxy, nitro, alkyl, carboxyalkyl, alkylthio, alkylsulfinyl, alkylsulfonyl, alkylcarbonyl, carbocyclyl, carbocyclylalkyl, carbocyclylalkenyl, carbocyclyloxy, carbocyclylalkoxy, carbocyclyloxyalkyl, carbocyclylthio, carbocyclylsulfinyl, carbocyclylsulfonyl, heterocyclylthio, heterocyclylsulfinyl, heterocyclylsulfonyl, carbocyclylalkoxy, carbocyclylheterocyclyl, heterocyclylalkyl, heterocyclyloxy, heterocyclylalkoxy, amino, aminoalkyl, alkylamino, alkenylamino, alkynylamino, carbocyclylamino, heterocyclylamino, aminocarbonyl, alkoxy, alkoxyalkyl, alkenyloxyalkyl, alkoxyalkylamino, alkylaminoalkoxy, alkoxycarbonyl, carbocyclyloxycarbonyl, heterocyclyloxycarbonyl, alkoxycarbonylamino, alkoxycarbocyclylamino, alkoxycarbocyclylalkylamino, aminosulfinyl, aminosulfonyl, alkylsulfonylamino, alkoxyalkoxy, aminoalkoxy, aminoalkylamino, alkylaminoalkylamino, carbocyclylalkylamino, alkylaminoalkylaminoalkylamino, alkylheterocyclylamino, heterocyclylalkylamino, alkylheterocyclylalkylamino, carbocyclylalkylheterocyclylamino, heterocyclylheterocyclylalkylamino, alkoxycarbonylheterocyclylamino, alkylaminocarbonyl, alkylcarbonylamino, hydrazinyl, alkylhydrazinyl, or carbocyclylhydrazinyl. Any substitutable member of such group optionally is substituted with one or more substituents independently selected from the group consisting of alkyl, alkenyl, hydroxy, halogen, haloalkyl, alkoxy, haloalkoxy, keto, amino, nitro, cyano, alkylsulfonyl, alkylsulfinyl, alkylthio, alkoxyalkyl, carbocyclyloxy, heterocyclyl, and heterocyclylalkoxy.

In some embodiments, the process comprises combining an isonipecotate with an anhydride. The isonipecotate corresponds in structure to Formula (VI):

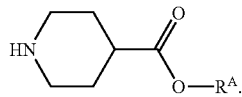
(VI)

The anhydride corresponds in structure to Formula (V):

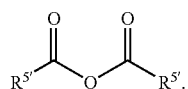
(V)

$R^A$ is alkyl. $R^{5'}$ is $R^{5A}$ or —O—$R^{5B}$. $R^{5A}$ is hydrogen, optionally-substituted alkyl, optionally-substituted aryl, or optionally-substituted heteroaryl. $R^{5B}$ is optionally-substituted alkyl, optionally-substituted alkenyl, optionally-substituted aryl, optionally-substituted arylalkyl, optionally-substituted heteroaryl, or optionally-substituted heteroarylalkyl.

In other embodiments, the process comprises forming a reaction mixture by a process comprising introducing a nitrogen-protected isonipecotate and a methyl heteroaryl into a reactor. The nitrogen-protected isonipecotate corresponds in structure to Formula (VIII):

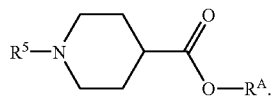
(VIII)

The methyl heteroaryl corresponds in structure to Formula (IX):

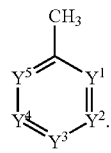
(IX)

Here, $R^A$, $Y^1$, $Y^2$, $Y^3$, $Y^4$, and $Y^5$ are as defined above. $R^5$ is a nitrogen-protecting group.

In other embodiments, the process comprises forming a reaction mixture by a process comprising introducing a ketone and a tosylhydrazide into a reactor. The ketone corresponds in structure to Formula (X):

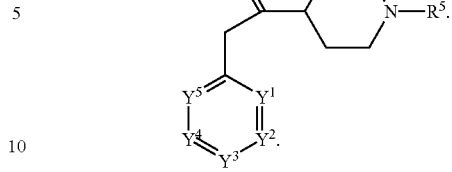
(X)

Here, $Y^1$, $Y^2$, $Y^3$, $Y^4$, $Y^5$, and $R^5$ are as defined above.

In other embodiments, the process comprises combining a hydrazone with a benzoyl halide. The hydrazone corresponds in structure to Formula (II):

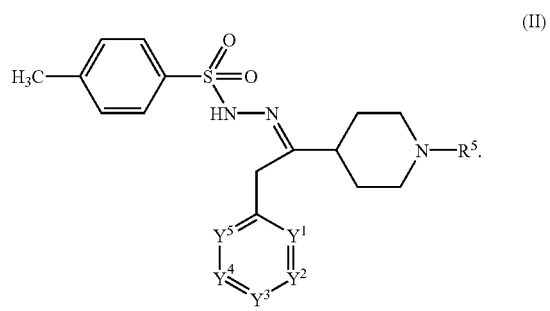
(II)

The benzoyl halide corresponds in structure to Formula (III):

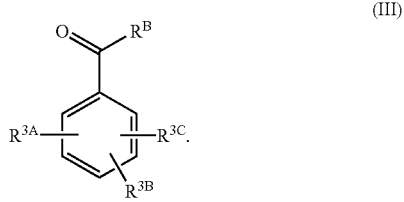
(III)

Here, $R^B$ is halogen. $Y^1$, $Y^2$, $Y^3$, $Y^4$, $Y^5$, and $R^5$ are as defined above.

In one such embodiment, the process comprises forming a mixture by a process comprising introducing a hydrazone of Formula (II) and a benzoyl halide of Formula (III) into a reactor. This mixture is the heated to a temperature of greater than 50° C.

In other embodiments, the process comprises forming a composition. Greater than 30% (by weight) of this composition consists of a protected pyrazole intermediate corresponding in structure to Formula (IV):

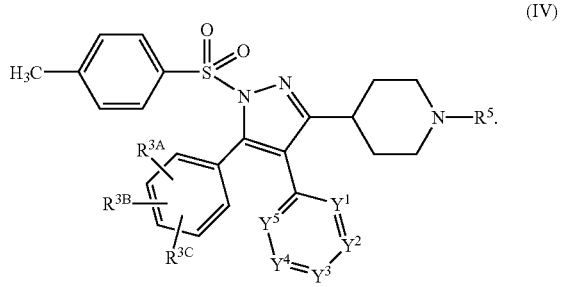
(IV)

Here, $R^{3A}$, $R^{3B}$, $R^{3C}$, $Y^1$, $Y^2$, $Y^3$, $Y^4$, $Y^5$, and $R^5$ are as defined above.

In other embodiments, the process comprises de-protecting at least one nitrogen of a nitrogen-protected substituted pyrazole. The nitrogen-protected substituted pyrazole corresponding in structure to Formula (IV).

In one such embodiment, the process comprises contacting an acid and toluene with a protected pyrazole intermediate corresponding in structure to Formula (IV).

In another such embodiment, the process comprises contacting a protected pyrazole intermediate corresponding in structure to Formula (IV) with an acid to form an acidic mixture. This acidic mixture is subsequently contacted with a base. The temperature of the acidic mixture is maintained at less than 65° C. between the time the acidic mixture is formed and the time a base is added to the acidic mixture.

In another embodiment, the process comprises contacting a protected pyrazole intermediate corresponding in structure to Formula (IV) with an acid to form an acidic mixture. The acidic mixture is subsequently contacted with a base to form a mixture having a greater pH. This mixture with a greater pH is subsequently heated to a temperature of greater than 25° C.

In other embodiments, the process comprises contacting an unsubstituted piperidinyl intermediate with acetonitrile. Here, the unsubstituted piperidinyl intermediate corresponds in structure to Formula (XV):

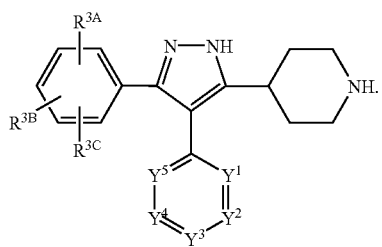

(XV)

Here, $R^{3A}$, $R^{3B}$, $R^{3C}$, $Y^1$, $Y^2$, $Y^3$, $Y^4$, and $Y^5$ are as defined above.

In other embodiments, the process comprises reacting a glycolic acid ester with an unsubstituted piperidinyl intermediate corresponding in structure to Formula (XV).

This invention also is directed, in part, to compositions (and methods of making such compositions) comprising compounds that may be used as intermediates of the above-described process. Greater than 30% (by weight) of these compositions consists of a compound corresponding in structure to Formula (IV).

This invention also is directed to processes for making compounds (as well as tautomers of the compounds, and the salts of the compounds and tautomers) that may, for example, be used as a starting material or intermediate in the above-described process for making the substituted pyrazoles of Formula (I).

In some such embodiments, the process is directed to making a nitrogen-protected isonipecotate corresponding in structure to Formula (VII):

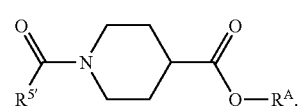

(VII)

Here, $R^A$ and $R^5$ are as defined above. The process comprises combining an isonipecotate of Formula (VI) with an anhydride of Formula (V).

In other embodiments, the process is directed to making a ketone corresponding in structure to Formula (X). The process comprises combining a nitrogen-protected isonipecotate of Formula (III) with a methyl heteroaryl Formula (IX).

In other embodiments, the process is directed to making a hydrazone corresponding in structure to Formula (II). The process comprises combining a ketone of Formula (X) with tosylhydrazide.

In other embodiments, the process is directed to making a nitrogen-protected pyrazole corresponding in structure to Formula (IV). The process comprises combining a hydrazone of Formula (II) with a benzoyl halide of Formula (III).

In other embodiments, the process is directed to making a substituted pyrazole, a tautomer of the substituted pyrazole. Here, the substituted pyrazole corresponds in structure to Formula (XV) or Formula (XVIII):

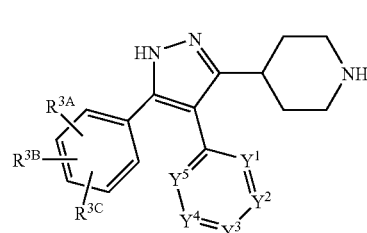

(XV)

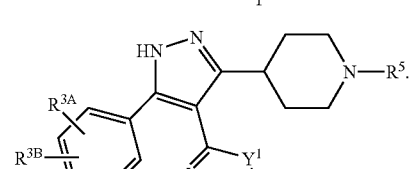

(XVIII)

Here, $R^{3A}$, $R^{3B}$, $R^{3C}$, $Y^1$, $Y^2$, $Y^3$, $Y^4$, $Y^5$, $R^4$, and $R^5$ are as defined above. The process comprises de-protecting at least one nitrogen of a nitrogen-protected substituted pyrazole of Formula (IV).

This invention also is directed to compounds (as well as tautomers of the compounds, and the salts of the compounds and tautomers) that may, for example, be used as a starting material or intermediate in the above-described process for making the substituted pyrazoles of Formula (I).

In some embodiments, the compound comprises a nitrogen-protected isonipecotate corresponding in structure to Formula (VII).

In other embodiments, the compound comprises a ketone corresponding in structure to Formula (X).

In other embodiments, the compound comprises a hydrazone corresponding in structure to Formula (II).

In other embodiments, the compound comprises a nitrogen-protected pyrazole corresponding structure to Formula (IV).

In other embodiments, the compound comprises a substituted pyrazole corresponding in structure to Formula (XVIII).

This invention is also directed, in part, to pharmaceutical compositions (or medicaments) comprising the compounds, tautomers, and salts made in accordance with this invention.

This invention is also directed, in part, to methods of making pharmaceutical compositions comprising the compounds, tautomers, and salts made in accordance with this invention.

This invention is also directed, in part, to methods of treatment using the compounds, tautomers, and salts made in accordance with this invention.

Further benefits of Applicants' invention will be apparent to one skilled in the art from reading this specification.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be various modified.

A. Compounds that may be Prepared by the Methods of this Invention

The compounds that may be prepared by the method of this invention include compounds corresponding in structure to the following Formula (I):

(I)

Here:

$R^{3A}$, $R^{3B}$, and $R^{3C}$ are independently selected from the group consisting of hydrogen, halogen, hydroxy, cyano, amino, alkyl, aminoalkyl, monoalkylamino, dialkylamino, alkoxy, and alkoxyalkyl. Any carbon of the alkyl, aminoalkyl, monoalkylamino, dialkylamino, alkoxy, or alkoxyalkyl optionally is substituted with one or more substituents independently selected from the group consisting of halogen, hydroxy, and cyano.

In some preferred embodiments, $R^{3C}$ is hydrogen; and $R^{3A}$ and $R^{3B}$ are independently selected from the group consisting of halogen, hydroxy, cyano, amino, alkyl, aminoalkyl, monoalkylamino, dialkylamino, alkoxy, and alkoxyalkyl. Any carbon of the alkyl, aminoalkyl, monoalkylamino, dialkylamino, alkoxy, or alkoxyalkyl optionally is substituted with one or more substituents independently selected from the group consisting of halogen, hydroxy, and cyano. In some such embodiments, the compound corresponds in structure to Formula (I-A):

(I-A)

In other embodiments, the compound corresponds in structure to Formula (I-B):

(I-B)

In other embodiments, the compound corresponds in structure to Formula (I-C):

(I-C)

In other embodiments, the compound corresponds in structure to Formula (I-D):

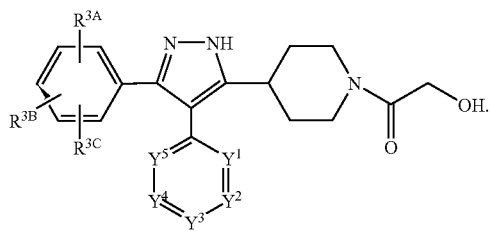

(I-D)

In other embodiments, the compound corresponds in structure to Formula (I-E):

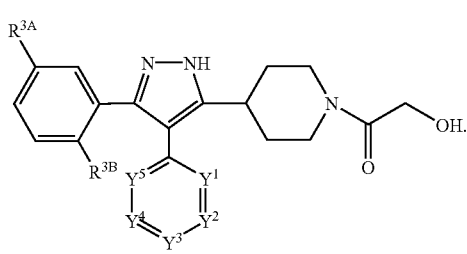
(I-E)

In other embodiments, the compound corresponds in structure to Formula (I-F):

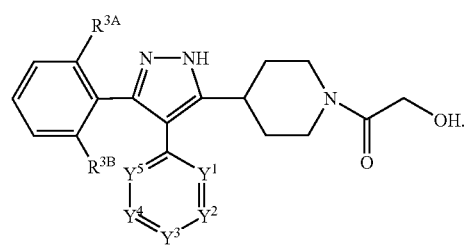
(I-F)

In some preferred embodiments, $R^{3B}$ and $R^{3C}$ are each hydrogen; and $R^{3A}$ is halogen, hydroxy, cyano, amino, alkyl, aminoalkyl, monoalkylamino, dialkylamino, alkoxy, or alkoxyalkyl. Any carbon of the alkyl, aminoalkyl, monoalkylamino, dialkylamino, alkoxy, or alkoxyalkyl optionally is substituted with one or more substituents independently selected from the group consisting of halogen, hydroxy, and cyano. In some such embodiments, the compound corresponds in structure to Formula (I-G):

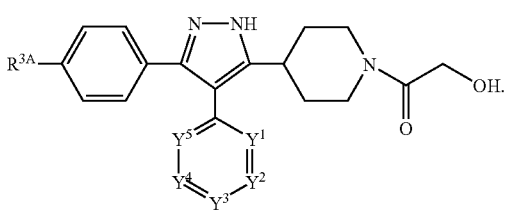
(I-G)

In some other embodiments, the compound corresponds in structure to Formula (I-H):

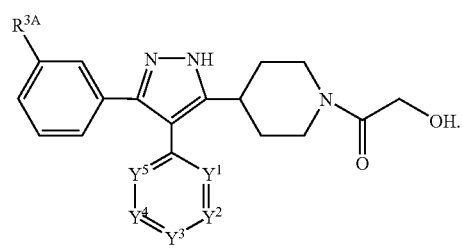
(I-H)

In some other embodiments, the compound corresponds in structure to Formula (I-I):

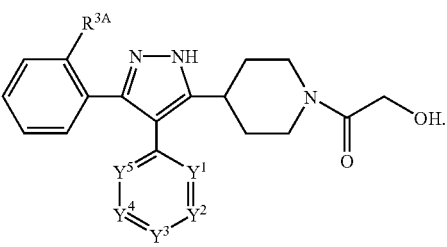
(I-I)

In some preferred embodiments, $R^{3A}$, $R^{3B}$, and $R^{3C}$ are independently selected from the group consisting of hydrogen, chloro, fluoro, hydroxy, cyano, amino, methyl, trifluoromethyl, ethyl, methoxy, and trifluoromethoxy.

In some preferred embodiments, $R^{3C}$ is hydrogen; and $R^{3A}$ and $R^{3B}$ are independently selected from the group consisting of chloro, fluoro, hydroxy, cyano, amino, methyl, trifluoromethyl, ethyl, methoxy, and trifluoromethoxy.

In some preferred embodiments, $R^{3B}$ and $R^{3C}$ are each hydrogen; and $R^{3A}$ is chloro, fluoro, hydroxy, cyano, amino, methyl, trifluoromethyl, ethyl, methoxy, or trifluoromethoxy.

One of $Y^1$, $Y^2$, $Y^3$, $Y^4$, and $Y^5$ is $=C(R^4)-$, i.e., a carbon atom double bonded to one atom, single bonded to an $R^4$ substituent, and single bonded to yet another atom:

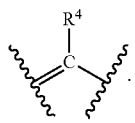

One of $Y^1$, $Y^2$, $Y^3$, $Y^4$, and $Y^5$ is $=N-$, i.e., a nitrogen atom double bonded to one atom and single bonded to another atom:

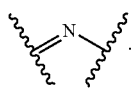

And three of $Y^1$, $Y^2$, $Y^3$, $Y^4$, and $Y^5$ are independently selected from the group consisting of $=C(H)-$ and $=N-$, i.e., three of $Y^1$, $Y^2$, $Y^3$, $Y^4$, and $Y^5$ are independently selected from the group consisting of $=$:

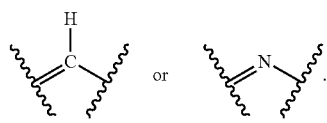

In some preferred embodiments, $Y^1$ is =C(H)— or =N—; $Y^2$ is =C($R^4$)—; $Y^3$ is =N—; and $Y^4$ and $Y^5$ are each =C(H)—.

In some preferred embodiments, $Y^1$ and $Y^3$ are each =N—, $Y^2$ is =C($R^4$)—, and $Y^4$ and $Y^5$ are each =C(H)—.

In some preferred embodiments, $Y^1$ and $Y^3$ are each =N—; and $Y^2$, $Y^4$, and $Y^5$ are each =C(H)—.

In some preferred embodiments, $Y^1$, $Y^2$, $Y^4$, and $Y^5$ are each =C(H)—; and $Y^3$ is =N—.

$R^4$ is hydrogen, halogen, cyano, hydroxy, thiol, carboxy, nitro, alkyl, carboxyalkyl, alkylthio, alkylsulfinyl, alkylsulfonyl, alkylcarbonyl, carbocyclyl, carbocyclylalkyl, carbocyclylalkenyl, carbocyclyloxy, carbocyclylalkoxy, carbocyclyloxyalkyl, carbocyclylthio, carbocyclylsulfinyl, carbocyclylsulfonyl, heterocyclylthio, heterocyclylsulfinyl, heterocyclylsulfonyl, carbocyclylalkoxy, carbocyclylheterocyclyl, heterocyclylalkyl, heterocyclyloxy, heterocyclylalkoxy, amino, aminoalkyl, alkylamino, alkenylamino, alkynylamino, carbocyclylamino, heterocyclylamino, aminocarbonyl, alkoxy, alkoxyalkyl, alkenyloxyalkyl, alkoxyalkylamino, alkylaminoalkoxy, alkoxycarbonyl, carbocyclyloxycarbonyl, heterocyclyloxycarbonyl, alkoxycarbonylamino, alkoxycarbocyclylamino, alkoxycarbocyclylalkylamino, aminosulfinyl, aminosulfonyl, alkylsulfonylamino, alkoxyalkoxy, aminoalkoxy, aminoalkylamino, alkylaminoalkylamino, carbocyclylalkylamino, alkylaminoalkylaminoalkylamino, alkylheterocyclylamino, heterocyclylalkylamino, alkylheterocyclylalkylamino, carbocyclylalkylheterocyclylamino, heterocyclylheterocyclylalkylamino, alkoxycarbonylheterocyclylamino, alkylaminocarbonyl, alkylcarbonylamino, hydrazinyl, alkylhydrazinyl, or carbocyclylhydrazinyl. Any substitutable member of such group optionally is substituted with one or more substituents independently selected from the group consisting of alkyl, alkenyl, hydroxy, halogen, haloalkyl, alkoxy, haloalkoxy, keto, amino, nitro, cyano, alkylsulfonyl, alkylsulfinyl, alkylthio, alkoxyalkyl, carbocyclyloxy, heterocyclyl, and heterocyclylalkoxy.

In some preferred embodiments, $R^4$ is halogen, cyano, hydroxy, thiol, carboxy, nitro, alkyl, carboxyalkyl, alkylthio, alkylsulfinyl, alkylsulfonyl, alkylcarbonyl, carbocyclyl, carbocyclylalkyl, carbocyclylalkenyl, carbocyclyloxy, carbocyclylalkoxy, carbocyclyloxyalkyl, carbocyclylthio, carbocyclylsulfinyl, carbocyclylsulfonyl, heterocyclylthio, heterocyclylsulfinyl, heterocyclylsulfonyl, carbocyclylalkoxy, carbocyclylheterocyclyl, heterocyclylalkyl, heterocyclyloxy, heterocyclylalkoxy, amino, aminoalkyl, alkylamino, alkenylamino, alkynylamino, carbocyclylamino, heterocyclylamino, aminocarbonyl, alkoxy, alkoxyalkyl, alkenyloxyalkyl, alkoxyalkylamino, alkylaminoalkoxy, alkoxycarbonyl, carbocyclyloxycarbonyl, heterocyclyloxycarbonyl, alkoxycarbonylamino, alkoxycarbocyclylamino, alkoxycarbocyclylalkylamino, aminosulfinyl, aminosulfonyl, alkylsulfonylamino, alkoxyalkoxy, aminoalkoxy, aminoalkylamino, alkylaminoalkylamino, carbocyclylalkylamino, alkylaminoalkylaminoalkylamino, alkylheterocyclylamino, heterocyclylalkylamino, alkylheterocyclylalkylamino, carbocyclylalkylheterocyclylamino, heterocyclylheterocyclylalkylamino, alkoxycarbonylheterocyclylamino, alkylaminocarbonyl, alkylcarbonylamino, hydrazinyl, alkylhydrazinyl, or carbocyclylhydrazinyl. Any substitutable member of such group optionally is substituted with one or more substituents independently selected from the group consisting of alkyl, alkenyl, hydroxy, halogen, haloalkyl, alkoxy, haloalkoxy, keto, amino, nitro, cyano, alkylsulfonyl, alkylsulfinyl, alkylthio, alkoxyalkyl, carbocyclyloxy, heterocyclyl, and heterocyclylalkoxy.

In some preferred embodiments, $R^4$ is hydroxy, alkylthio, alkylsulfinyl, alkylsulfonyl, carbocyclyloxy, carbocyclylalkoxy, carbocyclylthio, carbocyclylsulfinyl, carbocyclylsulfonyl, heterocyclylthio, heterocyclylsulfinyl, heterocyclylsulfonyl, carbocyclylalkoxy, heterocyclyloxy, heterocyclylalkoxy, amino, alkylamino, alkenylamino, alkynylamino, carbocyclylamino, heterocyclylamino, alkoxy, alkoxyalkylamino, alkylaminoalkoxy, alkoxycarbonylamino, alkoxycarbocyclylamino, alkoxycarbocyclylalkylamino, aminosulfinyl, aminosulfonyl, alkylsulfonylamino, alkoxyalkoxy, aminoalkoxy, aminoalkylamino, carbocyclylalkylamino, alkylaminoalkylamino, noalkylamino, alkylheterocyclylamino, heterocyclylalkylamino, alkylheterocyclylalkylamino, carbocyclylalkylheterocyclylamino, heterocyclylheterocyclylalkylamino, alkoxycarbonylheterocyclylamino, alkylcarbonylamino, hydrazinyl, alkylhydrazinyl, or carbocyclylhydrazinyl. Any substitutable member of such group optionally is substituted with one or more substituents independently selected from the group consisting of alkyl, alkenyl, hydroxy, halogen, haloalkyl, alkoxy, haloalkoxy, keto, amino, nitro, cyano, alkylsulfonyl, alkylsulfinyl, alkylthio, alkoxyalkyl, carbocyclyloxy, heterocyclyl, and heterocyclylalkoxy.

In some preferred embodiments, $R^4$ is hydroxy, carbocyclyloxy, carbocyclylalkoxy, carbocyclylalkoxy, heterocyclyloxy, heterocyclylalkoxy, amino, alkylamino, alkenylamino, alkynylamino, carbocyclylamino, heterocyclylamino, alkoxy, alkoxyalkylamino, alkylaminoalkoxy, alkoxycarbonylamino, alkoxycarbocyclylamino, alkoxycarbocyclylalkylamino, alkylsulfonylamino, alkoxyalkoxy, aminoalkoxy, aminoalkylamino, alkylaminoalkylamino, carbocyclylalkylamino, alkylaminoalkylaminoalkylamino, alkylheterocyclylamino, heterocyclylalkylamino, alkylheterocyclylalkylamino, carbocyclylalkylheterocyclylamino, heterocyclylheterocyclylalkylamino, alkoxycarbonylheterocyclylamino, alkylcarbonylamino, hydrazinyl, alkylhydrazinyl, or carbocyclylhydrazinyl. Any substitutable member of such group optionally is substituted with one or more substituents independently selected from the group consisting of alkyl, alkenyl, hydroxy, halogen, haloalkyl, alkoxy, haloalkoxy, keto, amino, nitro, cyano, alkylsulfonyl, alkylsulfinyl, alkylthio, alkoxyalkyl, carbocyclyloxy, heterocyclyl, and heterocyclylalkoxy.

In some preferred embodiments, $R^4$ is hydroxy, alkylthio, cyanocarbocyclyloxy, heterocyclyloxy, carbocyclylamino, dialkylaminoalkoxy, or dialkylaminoalkylamino.

In some preferred embodiments, $R^4$ is alkylthio.

In some preferred embodiments, $R^4$ is alkylsulfonyl.

In some preferred embodiments, $R^4$ is hydrogen.

Specific examples of preferred compounds include those corresponding in structure to the following formulas:

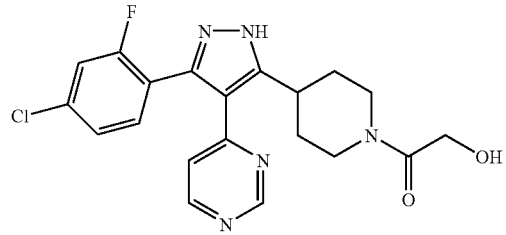

-continued
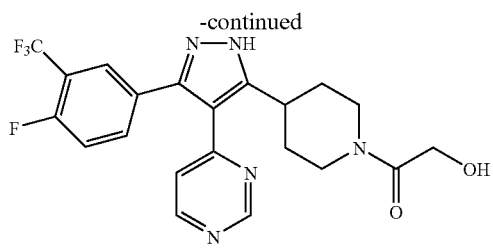
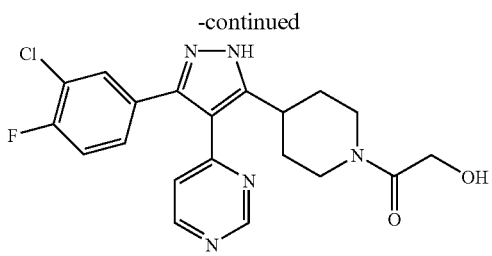
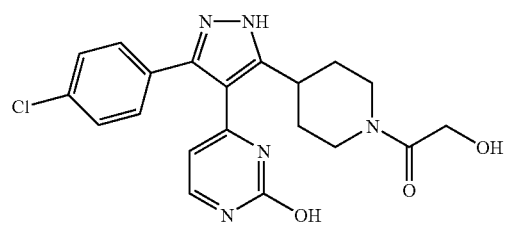
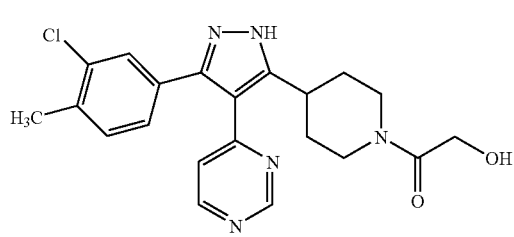
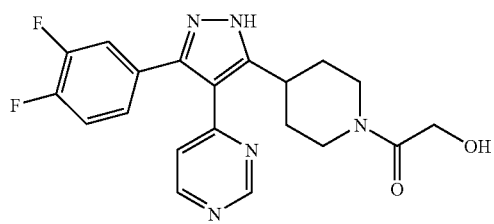
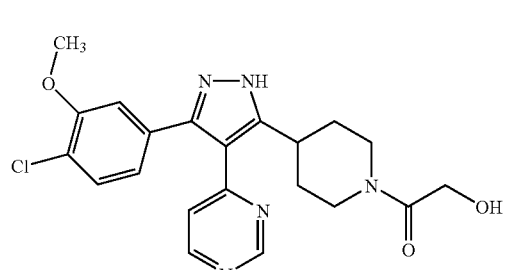
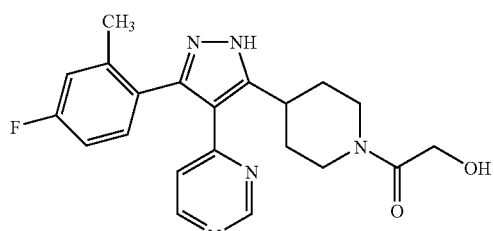
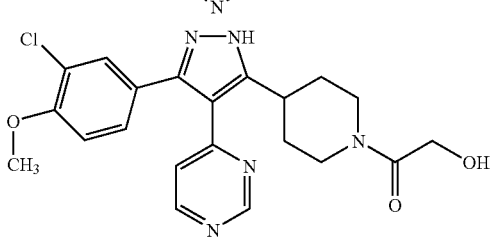
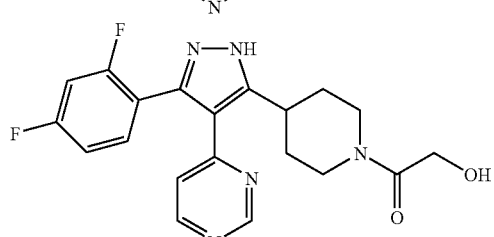
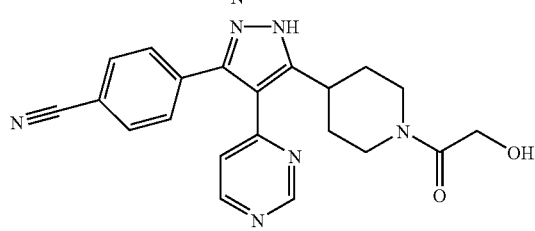
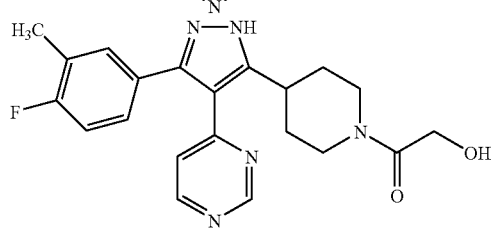
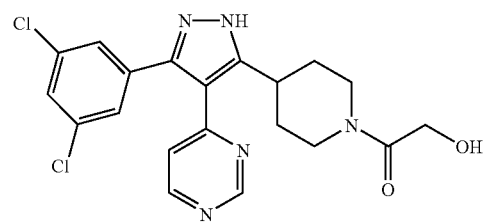
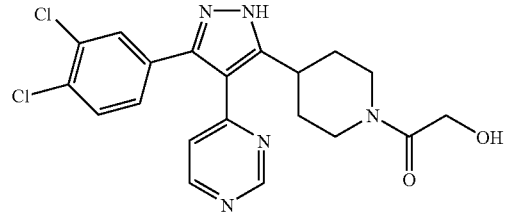

-continued
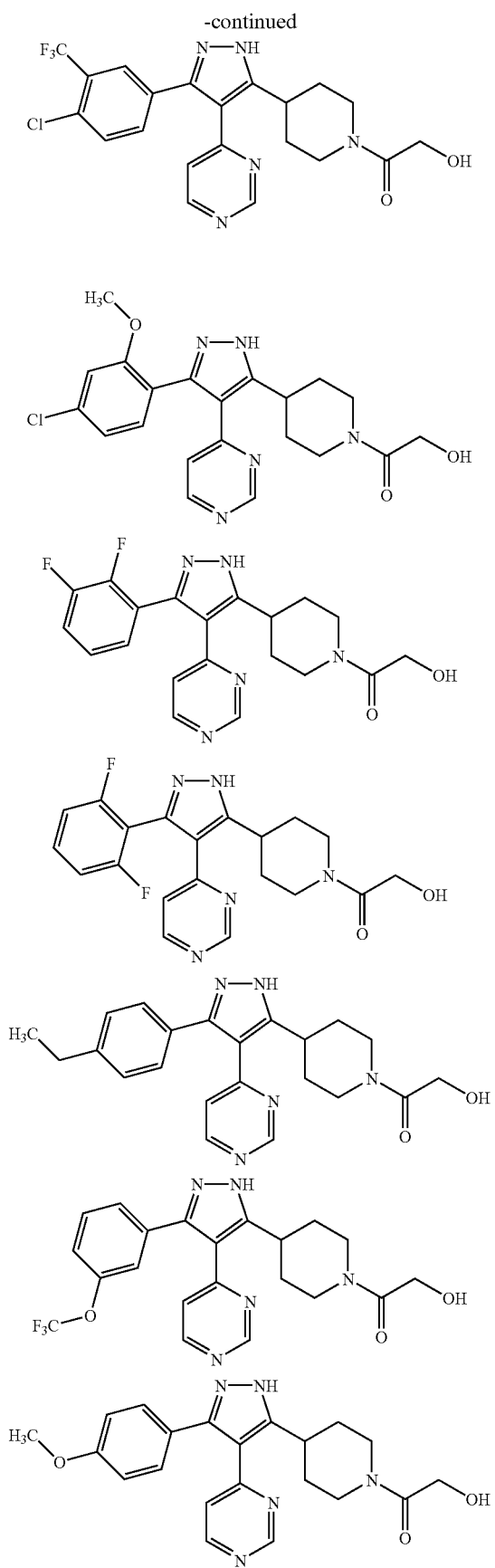
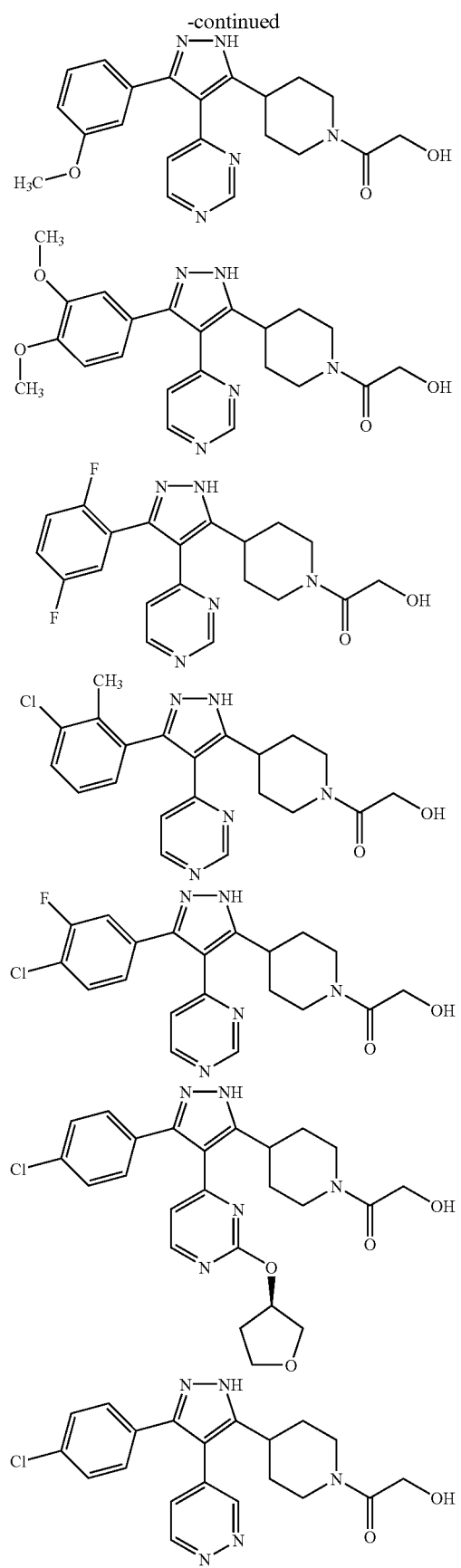

-continued
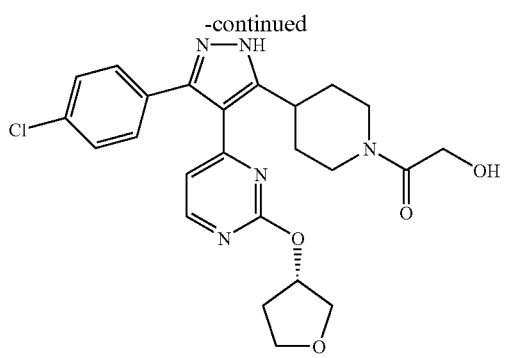
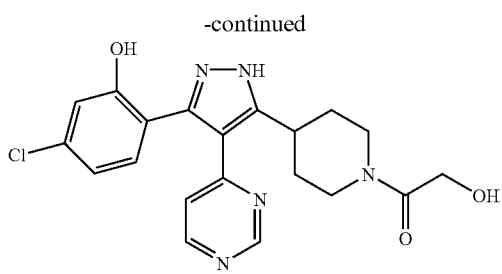
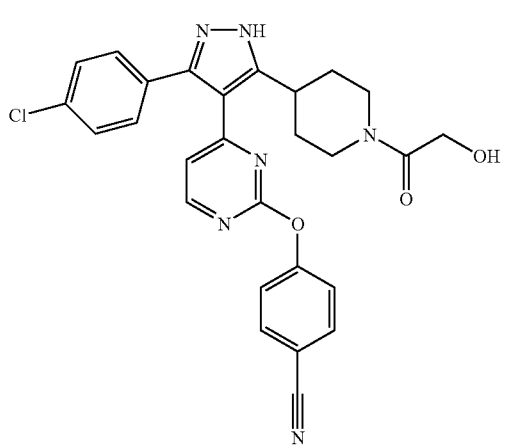
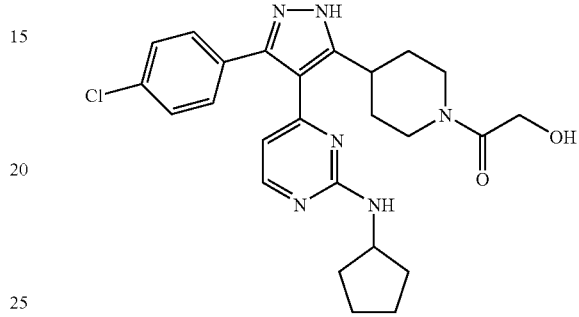
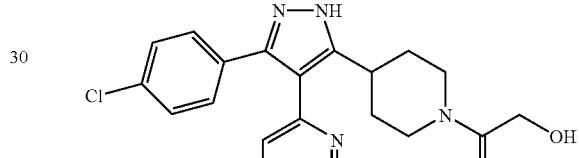
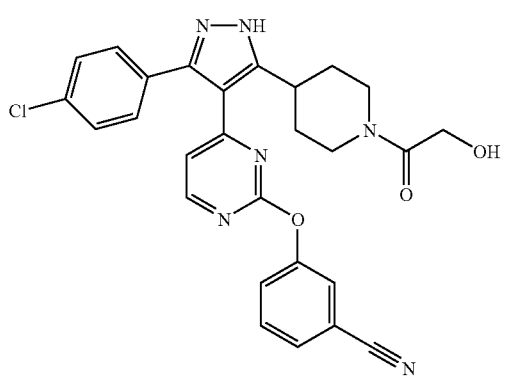
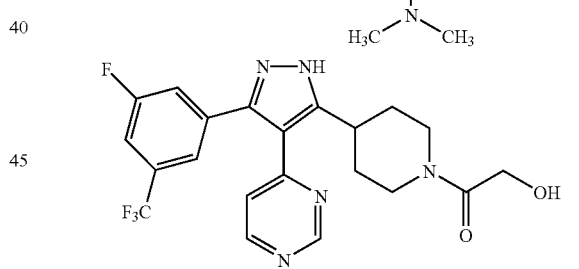
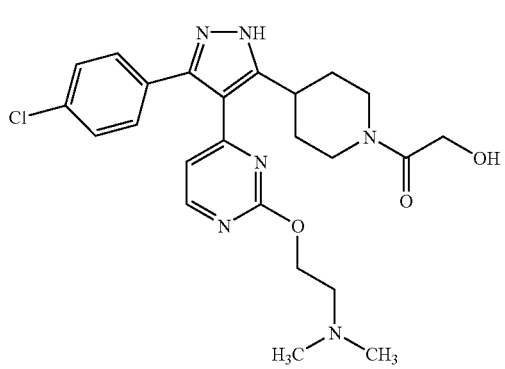
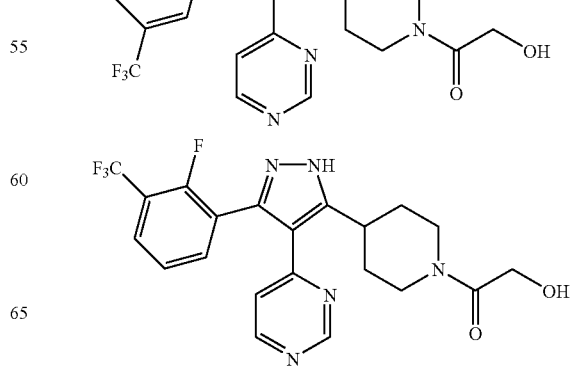

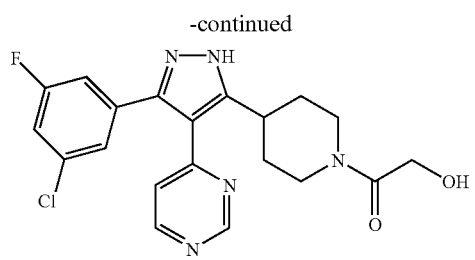
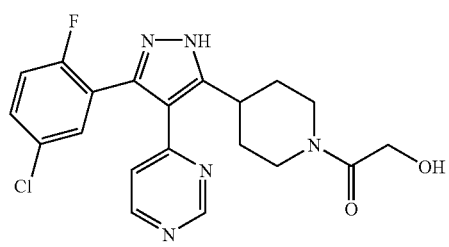
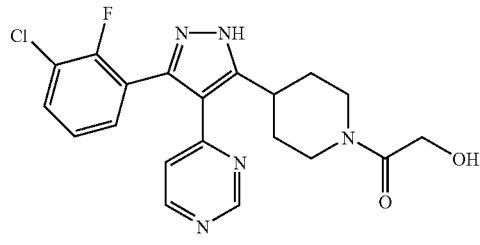
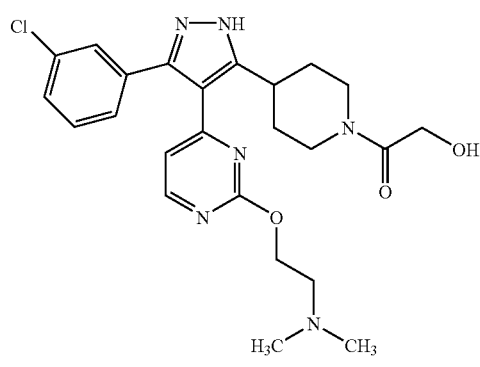
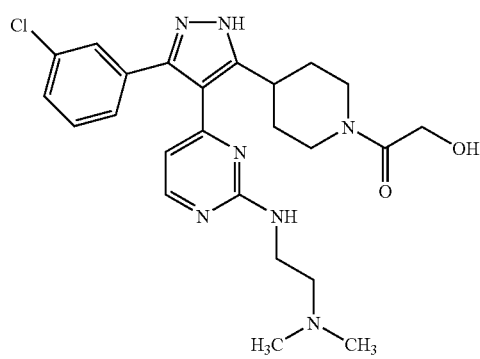
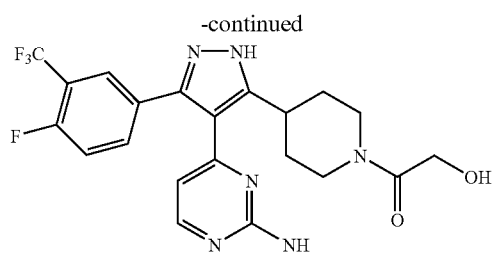
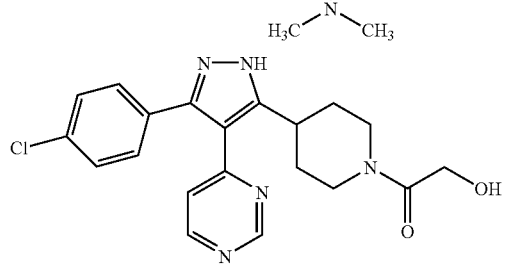
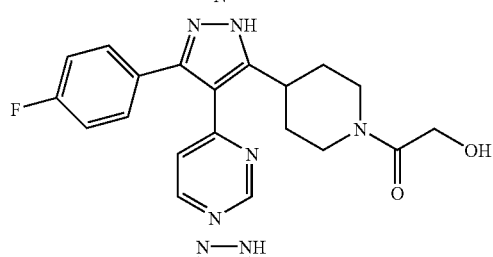
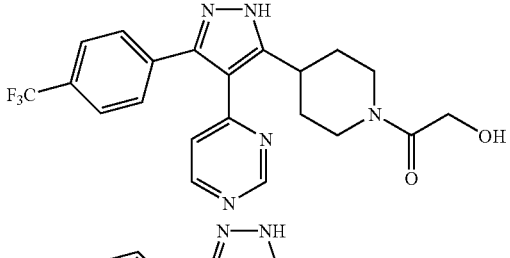
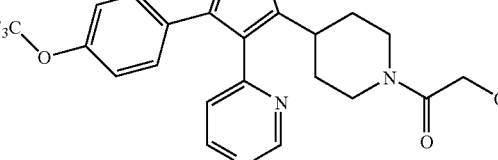
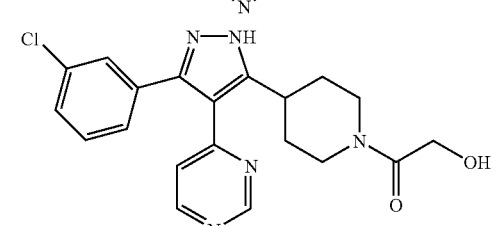
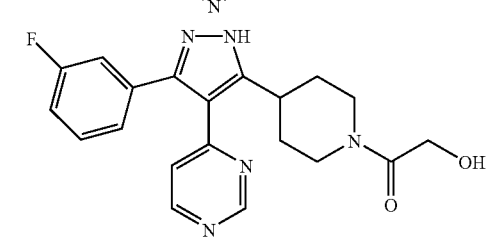

-continued
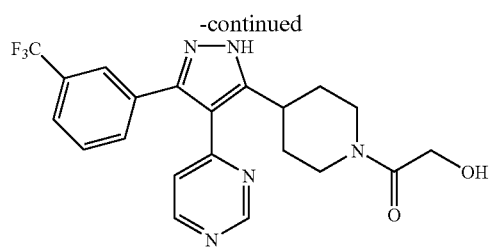
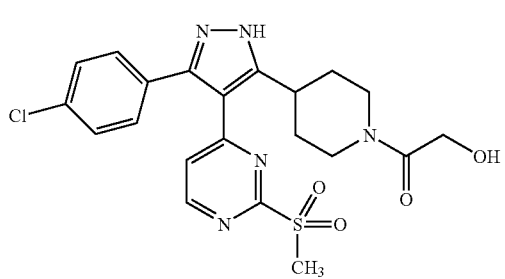
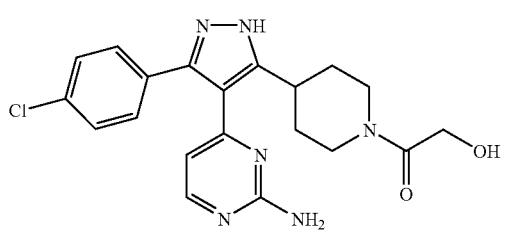
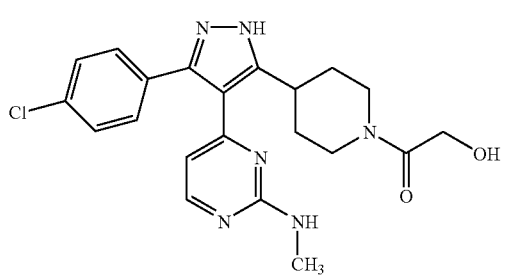
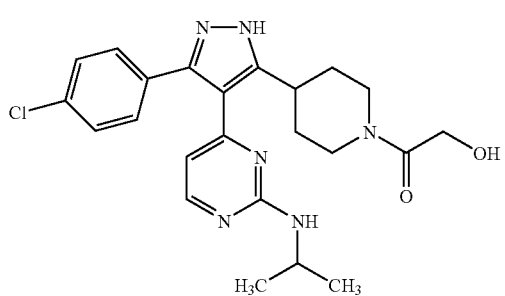
-continued
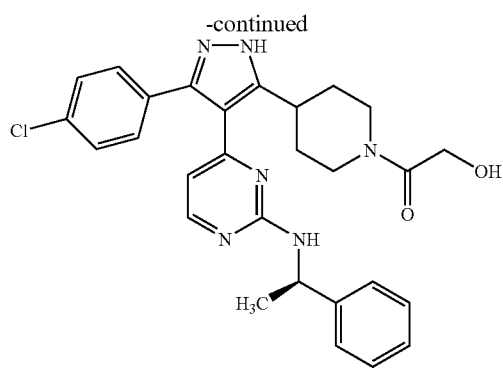
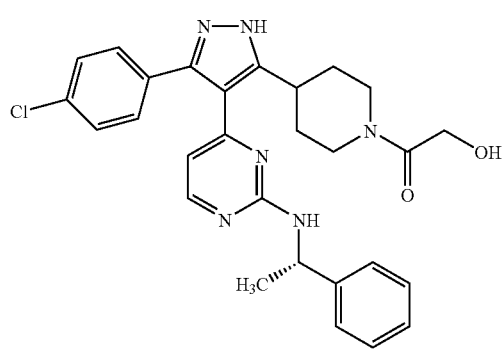
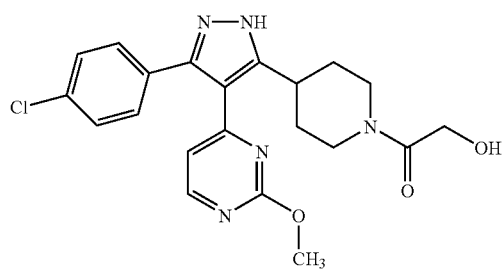
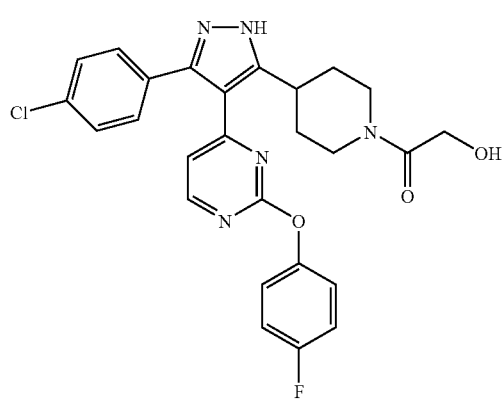

-continued

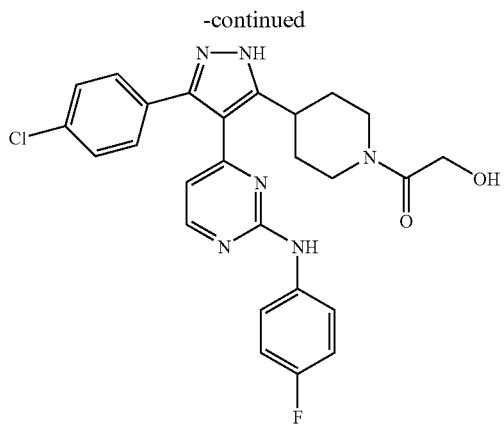

B. Compound Preparation Process

The compound and salts of this invention can be prepared from materials generally available in the art.

B-1. Preparation of Protected Isonipecotic Acid Starting Material

In a preferred embodiment, the synthesis begins by preparing a suitably protected ester of isonipecotic acid. The protecting group ($R^5$) may, for example, be a tert-butyloxycarbonyl radical (or "Boc"). The Boc-protected isonipecotic acid ester may be prepared from a commercially available isonipecotate compound and di-t-butyl dicarbonate:

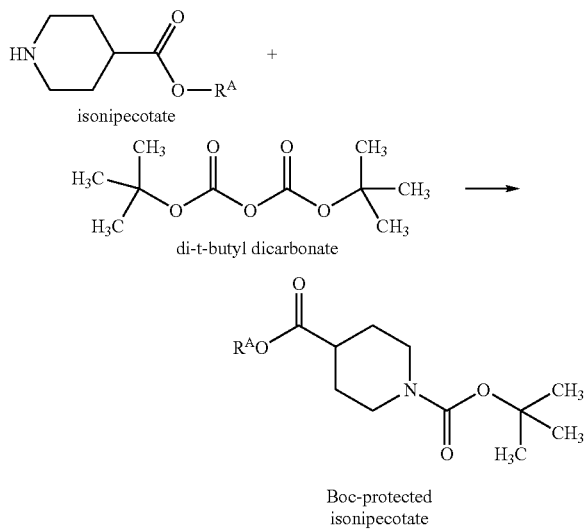

Here, $R^A$ may be, for example, alkyl, preferably $C_1$–$C_6$-alkyl, more preferably methyl or ethyl, and even more preferably ethyl. Thus, for example, the Boc-protected isonipecotic acid ethyl ester may be prepared from commercially available ethyl isonipecotate and di-t-butyl dicarbonate:

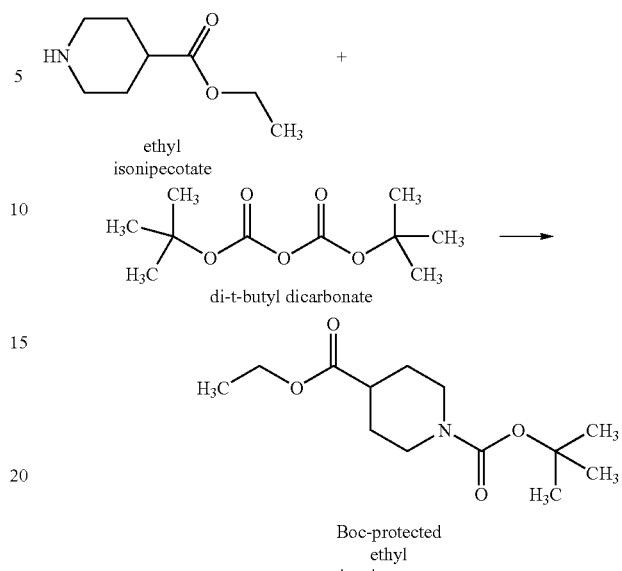

The methyl ester similarly may be prepared from commercially available methyl isonipecotate and di-t-butyl dicarbonate.

The di-t-butyl dicarbonate is preferably charged to a reactor with from about 1.01 to about 1.05 mole equivalents of the isonipecotate in a suitable solvent. The solvent may be, for example, tetrahydrofuran ("THF"). While adding the isonipecotate, the temperature of the resulting mixture preferably is maintained at from about zero to about 15° C. After all the isonipecotate has been added, the mixture is preferably warmed to room temperature (i.e., from about 20 to about 25° C.) and agitated (e.g., stirred) for at least about 1 hour, more preferably from about 1 to 3 hours, and even more preferably about 2 hours. Afterward, the contents are preferably cooled to from about 0 to about 10° C., more preferably to about 0° C., and the solvent is removed. When the solvent is THF, it may be removed by, for example, vacuum distillation.

Another suitable protecting group is acetyl. The acetyl-protected isonipecotate may be prepared from a commercially available ethyl isonipecotate and acetic anhydride:

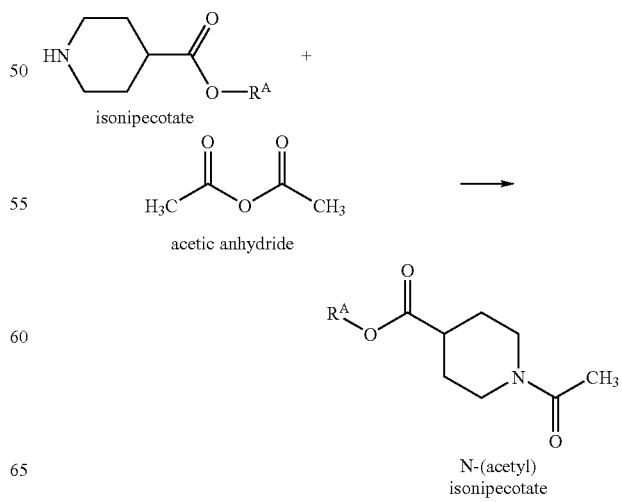

Here, $R^A$ may be, for example, as defined above. Thus, for example, the acetyl-protected isonipecotic acid ethyl ester may be prepared from commercially available ethyl isonipecotate and acetic anhydride:

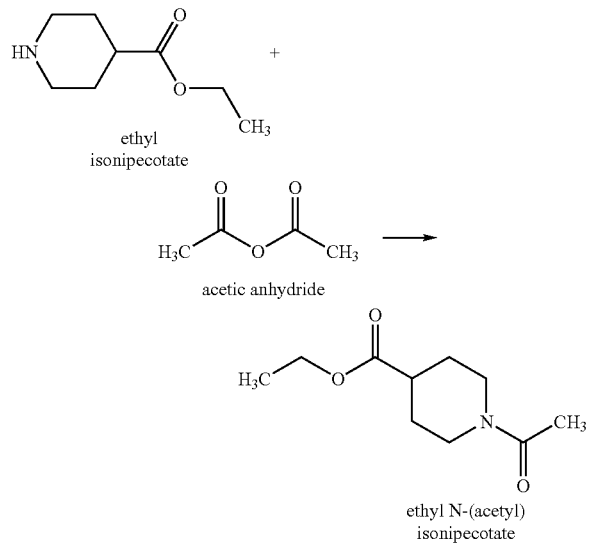

Other nitrogen protecting groups also may be used instead of the tert-butyloxycarbonyl and acetyl radicals, discuss above. Such groups include those corresponding in structure to —C(O)—$R^{5A}$, wherein $R^{5A}$ may be, for example, hydrogen, optionally-substituted alkyl (preferably methyl or ethyl), optionally-substituted aryl (preferably phenyl), or optionally-substituted heteroaryl. Other suitable groups include —C(O)—O—$R^{5B}$, wherein $R^{5B}$ may be, for example, optionally-substituted alkyl (preferably isobutyl and trichloroethyl), optionally-substituted alkenyl (preferably allyl), optionally-substituted aryl (preferably phenyl), optionally-substituted arylalkyl (preferably benzyl), optionally-substituted heteroaryl, or optionally-substituted heteroarylalkyl. Where, for example, the protecting group is —C(O)—$R^{5A}$ or —C(O)—O—$R^{5B}$, the protected isonipecotate may generally be prepared using, for example, the following reaction:

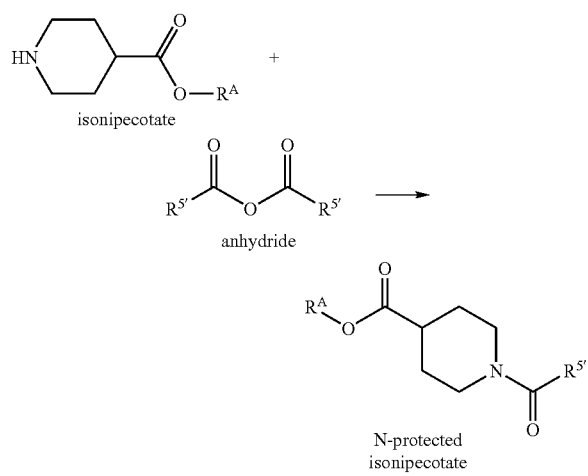

Here, $R^{5'}$ is $R^{5A}$ or —O—$R^{5B}$. Further suitable groups include optionally-substituted allyl, optionally-substituted arylmethyl (preferably phenylmethyl), and optionally-substituted heteroarylmethyl. A discussion relating to various suitable protecting groups may be found in, for example, Greene, T. W.; Wuts, P. G. M.; *Protective Groups in Organic Synthesis;* 3rd Ed.; Wiley: New York, 1999 (incorporated by reference into this patent).

B-2. Ketone Preparation

The protected isonipecotate may be reacted with a suitable methylheteroaryl to form a ketone in an acylation reaction:

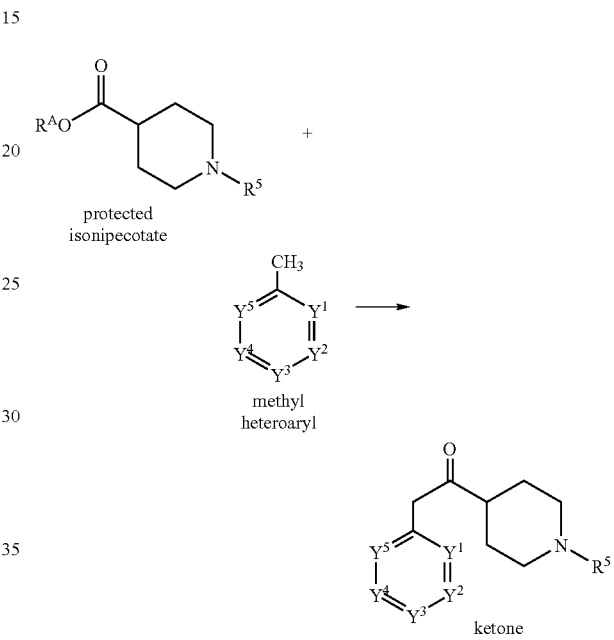

Here, $R^5$ is a nitrogen protecting group, such as a nitrogen protecting group described above. $Y^1$, $Y^2$, $Y^3$, $Y^4$, and $Y^5$ are as defined above, except that if $R^4$ is other than hydrogen, then the one of $Y^1$, $Y^2$, $Y^3$, $Y^4$, and $Y^5$ that is desired to be =C($R^4$)— is, in some instances, preferably =C(SCH$_3$)— at this stage of the process. To illustrate, if it is desired to make a substituted pyrazole wherein the substituent at the 4-position of the pyrazole is a pyrimidinyl group substituted at its 2-position, then the methylheteroaryl group would, in many instances, preferably be:

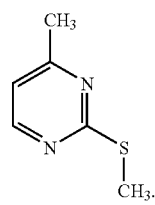

Before beginning this reaction, the methyl anion of the methylheteroaryl preferably is first prepared by treating the methylheteroaryl with from about 2.35 to about 2.49 mole equivalents, and more preferably from about 2.40 to about 2.42 mole equivalents of a base in the presence of an organic solvent (e.g., THF or ether, with THF typically being preferred) under nitrogen at a reduced temperature of preferably no less than about −10° C., and more preferably from about −6° C. to about 10° C. In some embodiments, the temperature is from about zero to about 10° C., and still even more preferably from about zero to about 5° C. The base may be, for example, lithium hexamethyldisilazide ("LiHMDS"), lithium diisopropylamide ("LDA"), or potassium tert-butoxide ("tBuOK"), with tBuOK being particularly preferred. The resulting mixture preferably is stirred for a brief period, typically at least about 0.25 hours, and more preferably from about 0.75 to about 1.25 hour. Subsequently, from about 0.95 to about 1.03 mole equivalents, and more preferably from about 0.95 to about 1.00 mole equivalent of the protected isonipecotate (based on moles of methylheteroaryl) is then added to the methyl anion mixture. In some embodiments, the protected isonipecotate is added slowly, typically over at least about 30 minutes.

Following the addition of the protected isonipecotate, the mixture is agitated (e.g., stirred) for preferably at least about 30 minutes, and, in some embodiments, at least about 2 hours. In some embodiments, for example, the mixture is initially stirred for from about 2 to about 4 hours, and even more preferably from about 3 to about 4 hours at a reduced temperature of from about 0 to about 10° C., more preferably from about 0 to about 5° C., and even more preferably about 5° C. In other embodiments, the mixture is initially stirred for from about 2 to about 20 hours at a temperature of from about −10 to about 10° C., and more preferably from about −6 to about 5° C.

After the initial stirring period, stirring is often continued at an increased temperature (e.g., at least about 5° C.) until at least about 98% of the protected isonipecotate has been consumed. In some embodiments, for example, the increased temperature is preferably from about 5 to about 15° C., and more preferably to about 10° C., while continuing to agitate the mixture. These conditions are particularly preferred where R5 is, for example, tert-butyloxycarbonyl. When conducted in a batch reactor, such conditions are typically maintained for from about 0.8 to about 1.2 hours, and more typically about 1 hour. In some embodiments, a greater temperature (e.g., from about 5 to about 40° C., more preferably from about 15 to about 40° C., and even more preferably from about 25 to about 35° C.) may be used. Use of such a greater temperature (particularly a temperature greater than 25° C.) tends to reduce the acylation reaction time. Such a temperature is particularly suitable where $R^5$ is acetyl. When such a greater temperature is used, the temperature preferably is increased slowly, typically over at least about 30 minutes (especially where the temperature is increased to about 35° C.).

Impurities may be removed from the resulting ketone product mixture using acid/base extraction. In a preferred embodiment, sufficient acid is added to the product mixture to reduce the pH to from about 6 to about 7. Typically, from about 2.28 to about 2.52 mole equivalents, and more preferably about 2.35 to about 2.4 mole equivalents of an acid solution (based on moles of protected isonipecotate) are added to the reaction mixture. The acid may be, for example, aqueous acetic acid or a mineral acid (preferably HCl). During this acid addition, the temperature preferably is maintained at less than about 30° C., with a temperature of less than about 25° C. being preferred in some embodiments.

In some embodiments, the mixture is initially cooled to less than about 20° C., and more preferably from about 5 to about 15° C., and even more preferably about 10° C. before the acid addition.

In some embodiments (particularly where the protecting group is tert-butyloxycarbonyl), the aqueous phase is removed (in, for example, a separatory funnel) following the addition of the acid solution, and from about 0.23 to about 0.27 mole equivalents, and more preferably about 0.25 mole equivalents of an additional acid solution (based on moles of protected isonipecotate) is then added to the organics. The acid may be, for example, ammonium chloride or a dilute mineral acid such as 0.5 N hydrochloric acid. After the acid is added, the aqueous phase is preferably removed. The organic solvent may then be removed from the ketone product using, for example, distillation. If, for example, the solvent is THF, it may be removed by slowly increasing the batch temperature under vacuum (e.g., 200 torr) until it reaches from about 60 to about 65° C.

In other embodiments (particularly where the protecting group is acetyl), the hydrazone formation reaction (discussed below) is carried out in an aqueous environment. In those instances, the acidified ketone product mixture preferably is cooled to less than 20° C., more preferably from about 10 to about 20° C., and still more preferably about 15° C. following the acid addition. The pressure preferably also is decreased to less than atmospheric pressure, such as, for example, about 150 torr. The temperature is then preferably slowly increased to remove the solvents via distillation. During this distillation, the temperature preferably is increased to no greater than about 50° C., and more preferably no greater than 45° C. (particularly where the pressure is about 150 torr). Where the pressure is reduced during the distillation, it preferably is increased back to ambient pressure following the distillation. This preferably is achieved using, for example, nitrogen. Water preferably is added following the distillation. The amount of water preferably is greater than about 1 ml (more preferably from about 2 to about 7 ml, and even more preferably from about 4 to about 6 ml) per gram of the methylheteroaryl used in the ketone formation reaction.

B-3. Hydrazone Preparation

The ketone may next be reacted with toluenesulfonylhydrazide to form a hydrazone in a condensation reaction:

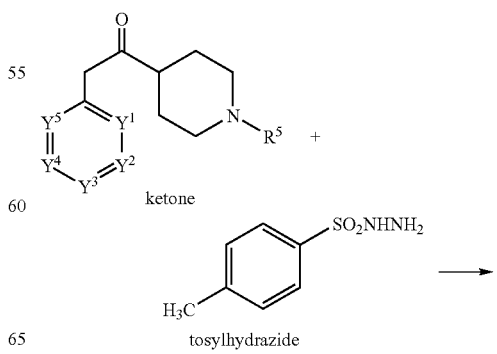

-continued

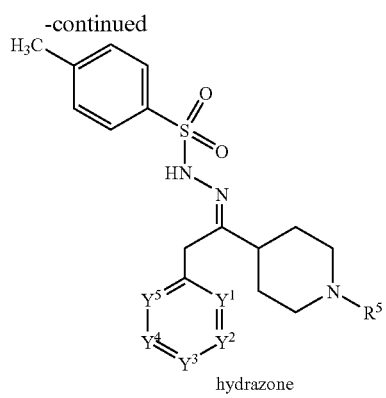

hydrazone

B-3(A). Hydrazone Formation in an Organic Solvent

In some preferred embodiments (such as where $R^5$ is tert-butyloxycarbonyl), the ketone product is combined with an organic solvent, such as toluene, benzene, or THF, with toluene typically being more preferred. Various impurities that may be present in this mixture (e.g., isonipecotic acid and/or ammonium chloride) are preferably removed by adding water, agitating (e.g., stirring) the mixture for a brief period (e.g., 30 min), letting the mixture stand for a brief period (e.g., 1 hour), and then removing the aqueous layer. The remaining organic layer is then combined with toluenesulfonylhydrazide. The mole ratio of toluenesulfonylhydrazide to protected isonipecotate reagent (used in the ketone-forming reaction) is preferably from about 0.87 to about 0.93, and more preferably about 0.9.

After the toluenesulfonylhydrazide has been combined with the ketone, the mixture is preferably heated to a temperature of from about 66 to about 74° C., and more preferably to about 70° C., while being agitated (e.g., stirred). This heating and agitation is preferably continued for from about 1.8 to about 2.2 hours, and more preferably about 2 hours. The mixture is preferably next refluxed at about 70° C. under reduced pressure (e.g., 200 torr) using, for example, a Dean-Stark moisture trap for from about 1.6 to about 2.4 hours, and more preferably 2 hours. The basic principles underlying the design of a Dean-Stark moisture trap are well-known in the art and described in, for example, Dean, E. W. & Stark, D. D., "A Convenient Method for the Determination of Water in Petroleum and Other Organic Emulsions," *J. Indus. and Eng. Chem.*, Vol. 12, No. 5. pp. 486–90 (May 1920) (incorporated herein by reference).

After the heating, the mixture is preferably cooled to from about −5 to about 5° C., and more preferably about 0° C., over from about 1.2 to about 1.8 and more preferably about 1.5 hours. The cooling is then preferably continued for from at least about 10 hours, and more preferably at least about 12 hours. Following the cooling period, the hydrazone solids preferably are separated (using, for example, filtration or centrifugation), washed with a solvent (e.g., toluene, benzene, THF and/or ethyl acetate, and preferably ethyl acetate), and then dried (e.g., under vacuum at an elevated temperature of from about 25 to about 40° C., and more preferably about 40° C.).

B-3(B). Acid-Catalyzed Hydrazone Formation in Aqueous Environment

In other preferred embodiments (such as where $R^5$ is acetyl), the ketone is combined with toluenesulfonylhydrazide in the presence of an aqueous acid solution. The mole ratio of toluenesulfonylhydrazide to protected isonipecotate reagent (used in the ketone-forming reaction) is preferably from about 0.9 to about 1:1, and more preferably about 1:1. A co-solvent also may be charged to the reactor. The co-solvent preferably is a polar solvent. In some embodiments, methanol is particularly preferred. In other embodiments, ethanol is particularly preferred. In still other embodiments, dimethylacetamide ("DMAC") is particularly preferred (this co-solvent, for example, allows for the toluenesulfonylhydrazide reagent to be added as a solution). The amount of co-solvent preferably is at least about 1 ml (more preferably from about 2 to about 8 ml, and even more preferably from about 6 to about 7.5 ml) per gram of methylheteroaryl used in the ketone formation reaction.

After the toluenesulfonylhydrazide (and any co-solvent) has been combined with the ketone in the reactor, the mixture is preferably heated to a temperature of greater than about 25° C., more preferably from about 40 to about 66° C., more preferably from about 40 to about 55° C. while being agitated (e.g., stirred), and even more preferably from about 45 to about 50° C. while being agitated (e.g., stirred). At this point, acid preferably is added. The acid may be selected from a wide variety of acids, but preferably is a mineral acid, with HCl being particularly preferred. In many embodiments, sufficient acid is added to obtain a pH of less than 7, more preferably from about 2 to about 5, even more preferably from about 2 to about 4, and still even more preferably about 3. Typically, at least about 0.01 equivalent of acid (relative to moles of ketone) is charged to the reactor, with from about 0.01 to about 0.1 equivalents being more preferred, and from about 0.025 to about 0.075 equivalents being even more preferred, and about 0.05 equivalents typically being still even more preferred.

The resulting mixture preferably is agitated at the increased temperature until at least about 96% of the ketone has been consumed. Typically, the condensation reaction time under these condition is at least about 15 minutes, and more typically at least about 30 minutes.

Following the condensation reaction, base (e.g., NaOH) preferably is added. The amount of base added preferably is sufficient to increase the pH to from about 6 to about 8, and more preferably about 7. The amount of base typically is at least about 0.01 equivalent of acid (relative to moles of ketone reagent used in the condensation reaction), with from about 0.01 to about 0.1 equivalents being more preferred, and from about 0.025 to about 0.075 equivalents being even more preferred, and about 0.05 equivalents typically being still even more preferred. In some preferred embodiments, the amount of base added preferably is substantially the molar equivalent of the amount of acid added to catalyze the condensation reaction. The base addition preferably is carried out at a temperature falling within the preferred temperature range for the condensation reaction. If no solids precipitate upon the addition of the base, the mixture preferably is seeded with a small amount (e.g., 50 mg) of the desired hydrazone.

Following the base addition, the mixture preferably is agitated for at least about 15 minutes, and more preferably at least about 30 minutes still at a temperature falling within the preferred temperature range for the condensation reaction. Afterward, the mixture preferably is cooled to a temperature of less than 20° C., more preferably to a temperature of from about 5 to about 15° C., and still more preferably to a temperature of about 10° C. This cooling preferably is gradual, and typically is carried out over a period of at least about 1 hour, and more preferably about 1.5 hours.

Following the cooling period, the hydrazone solids preferably are separated (using, for example, filtration or centrifugation), washed with a solvent (e.g., water), and then dried. The drying preferably is conducted under vacuum (e.g. at a pressure of no greater than about 100 torr) and at a temperature of greater than about 25, more preferably greater than about 40° C., and even more preferably from about 40° C. to about 60° C.).

B-4. Preparation of Protected Pyrazole

The hydrazone may next be reacted with a suitable optionally-substituted benzoyl halide to form a protected pyrazole intermediate:

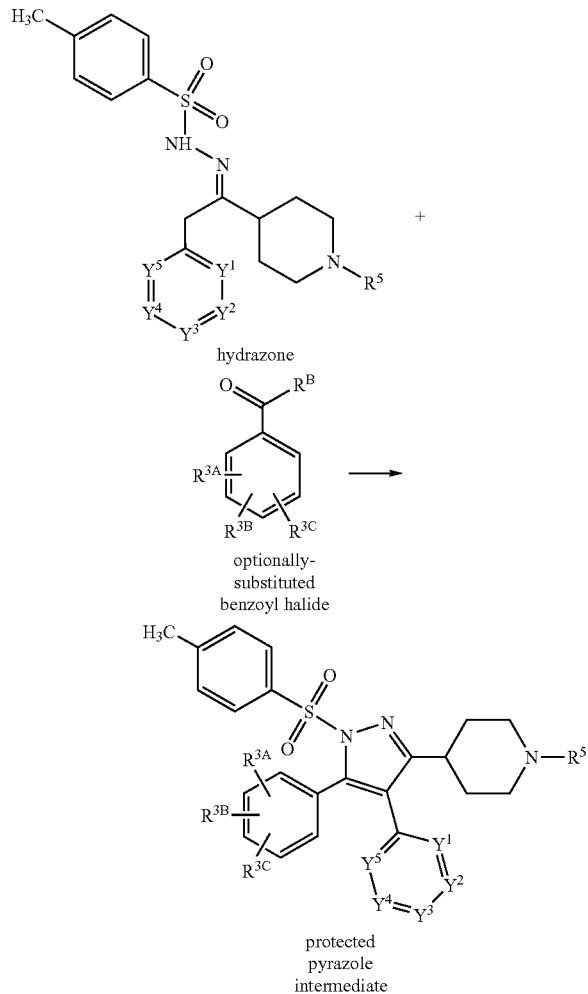

Here, $R^B$ is halogen, preferably chloro.

In a preferred embodiment, the hydrazone is charged to a clean dry reactor (which preferably has been purged with nitrogen), along with a solvent, base, and the benzoyl halide.

The amount of solvent preferably is from about 3:1 to about 5:1 (ml solvent:grams hydrazone solids). In some embodiments, the amount of solvent is from about 4.2:1 to about 4.8:1 (ml solvent:grams hydrazone solids, and still more preferably about 4.5:1 (ml solvent:grams hydrazone solids). In other embodiments, the amount of solvent is from about 3.8 to about 4.2 (ml solvent:grams hydrazone solids), and more preferably about 4:1 (ml solvent:grams hydrazone solids). The solvent may be, for example, THF or toluene.

The amount of base preferably is from about 1.05 to about 1.68 mole equivalents, and more preferably about 1.4 mole equivalents (based on moles of hydrazone). The base may be, for example, LiHMDS, LDA, tBuOK, or triethylamine, with triethylamine being particularly preferred.

To enhance the rate of reaction, an activator of the benzoyl halide may be included in the reaction mixture as well. For example, about 0.1 mole equivalents of 4-N,N-dimethylaminopyridine (based on moles of hydrazone reagent) may be included, particularly where the benzoyl halide is, for example, 4-chlorobenzoylchloride.

The benzoyl halide (typically at room temperature) is preferably slowly charged to the reactor after the hydrazone, solvent, base, and any activator have been charged. Typically, this addition takes place over a period of at least about 5 minutes, preferably at least about 10 minutes, and more preferably at least about 15 minutes. The amount of the benzoyl halide preferably is from about 1.01 to about 1.25 mole equivalents, and more preferably from about 1.20 to about 1.25 mole equivalents (based on moles of hydrazone).

Once the benzoyl halide has been charged, the reaction mixture preferably is heated. In some embodiments, the mixture is heated to a temperature of at least about 50° C., more preferably greater than 50° C., even more preferably greater than 50° C. and no greater than about 65° C., and still even more preferably to about 65° C. In some embodiments, the mixture is heated to reflux. The heating is then preferably continued until at least about 98% of the hydrazone has been consumed. Typically, the heating is continued for greater than 30 minutes, more preferably at least about 1 hour, even more preferably from about 1 to about 2 hours, and still even more preferably about 2 hours. The resulting product mixture is then preferably allowed to cool to room temperature.

B-5. Isolation of the Protected Pyrazole

In some embodiments, it is preferred to isolate the protected pyrazole product from the product mixture. Applicants have found, for example, that such isolation can improve product yield, purity, and reproducibility downstream. To remove existing salt impurities (and any other impurities soluble in water), water may be added to the product mixture. The product mixture is preferably then agitated (e.g., stirred) for at least about 0.5 hours, more preferably from about 0.5 to about 1 hour, and even more preferably about 0.5 hours. Phase separation is then allowed to occur, and the aqueous layer is removed. To remove impurities and color from the organics, an aqueous salt solution (approximately at least about 25% (by weight), more preferably from about 3.5 to about 3.88 mole equivalents (based on moles of hydrazone), and even more preferably about 3.66 mole equivalents (based on moles of hydrazone)) can subsequently (or alternatively) be added to the organic phase. The salt in the salt solution preferably does not exceed the saturation concentration at room tem perature. A particularly advantageous salt solution is aqueous ammonium chloride. As with the water separation, the combined salt solution and organics are agitated for from about 0.5 to about 1 hour, and even more preferably about 0.5 hours. Phase separation is then allowed to occur, and the aqueous layer is removed. The separation may be conducted at room temperature.

Following phase separation to remove impurities, the protected pyrazole intermediate preferably is precipitated out of the organic solvent. This preferably is achieved, at least in part, by using an anti-solvent. An anti-solvent is a second solvent that, when mixed with a first solvent containing a solubilized ingredient (in this case, the protected pyrazole intermediate), causes that ingredient to be less soluble than it is in the first solvent alone. The anti-solvent in this instance may be, for example, a $C_1$–$C_6$ alcohol, preferably isopropyl alcohol ("IPA"). In a preferred embodiment, a preheated mixture (preferably at a temperature of greater than 25° C., more preferably at from about 50 to about 60° C., and even more preferably at 55° C.) of IPA in water (preferably containing about 1:1 (vol:vol) IPA to water) is added to the reaction mixture (preferably after being pre-heated to a temperature of greater than 25° C., more preferably to from about 50 to about 60° C., and even more preferably to about 55° C.) over a time period of at least 1 hour, more preferably from about 1 to about 2 hours, and even more preferably about 1 hour. After the addition is complete, the solution is preferably agitated (e.g., stirred) at a temperature of greater than 25° C., more preferably from about 50 to about 60° C., and even more preferably about 55° C., for at least about 3 hours, more preferably from about 3 to about 5 hours, and even more preferably about 3 hours. The solution is then preferably cooled to a temperature of from about 20 to about 28° C., and more preferably to about 25° C., at a rate of from about 0.1 to about 1° C. per minute, and more preferably at a rate of about 0.3° C. per minute. The slurry is then held at a temperature of from about 20 to about 28° C., and more preferably about 25° C., for at least about 2 hours, more preferably for from about 2 to about 24 hours, and even more preferably for about 2 hours. The precipitate is then preferably removed using, for example, filtration (with, for example, a 4 micron filter cloth) or centrifugation. The solids are preferably washed with additional anti-solvent and/or water, and dried. The solids may be dried using, for example, heat optionally under vacuum. If heat is used, the temperature is preferably from about 70 to about 80° C., and more preferably about 80° C. The concentration of the protected pyrazole intermediate in the cake preferably is greater than 30% (by weight), and in a particularly preferred embodiment is at least about 50% (by weight), more preferably at least about 75% (by weight), even more preferably at least about 95% (by weight), still even more preferably at least about 97% (by weight), and still yet even more preferably at least about 98.5% (by weight).

B-6. Deprotection of the Protected Pyrazole

The protected pyrazole intermediate preferably is de-protected to form a de-protected pyrazole intermediate (also referred to in this patent as an "unsubstituted piperidinyl intermediate"):

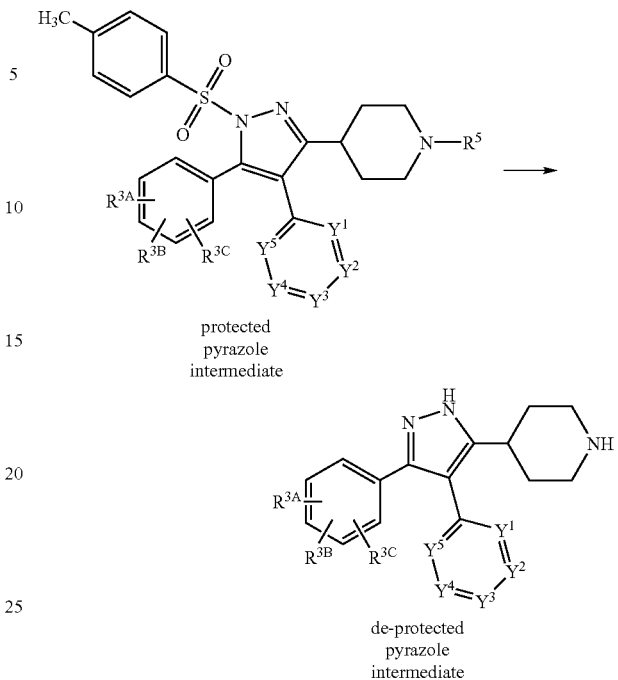

protected pyrazole intermediate de-protected pyrazole intermediate

In some embodiments, the hydrazone formation reaction product mixture is used directly in the pyrazole de-protection reaction. In other embodiments, however, the protected pyrazole is isolated as, for example, described in Section B-5. In such instances, the protected pyrazole is preferably mixed with a solvent to form a slurry before the de-protection. The solvent may be, for example, water, THF, ethyl acetate, ethanol, butanol, isopropyl alcohol, acetone, or toluene. In some particularly preferred embodiments, the solvent is THF or toluene. The amount of solvent preferably is at least about 1:1 (ml solvent:grams protected pyrazole), and more preferably from about 2:1 to about 10:1 (ml solvent:grams protected pyrazole). In some preferred embodiments, for example, the amount of solvent is about 2.5:1 (ml solvent:grams protected pyrazole).

B-6(A). Deprotection Using a Base

In some embodiments, the protected pyrazole intermediate is de-protected using basic conditions. In these embodiments, a base and water are slowly charged to a reactor containing the protected pyrazole solution. The amount of base preferably is from about 2 to about 10 mole equivalents, more preferably from about 4 to about 8 mole equivalents, and even more preferably about 6.0 mole equivalents of base (based on moles of protected pyrazole intermediate). The amount of water may vary widely, but preferably is from about 1 to about 10 ml (more preferably from about 2 to about 6 ml, and even more preferably from about 3 to about 5 ml) per gram of hydrazone reagent used to make the protected pyrazole. Although a wide variety of bases may be suitable, alkali metal hydroxides are preferred, with NaOH often being particularly preferred.

The mixture comprising the protected pyrazole and base preferably is heated to a temperature of greater than 25° C.

Often, for example, the mixture is distilled to remove an organic solvent(s) in the mixture. Normally, at least one such solvent is present, either as a solvent remaining from the reaction forming the protected pyrazole and/or as a solvent added subsequent to the reaction forming the protected pyrazole. In either event, the mixture preferably is distilled at a temperature sufficient to distill off the organic solvent(s). The mixture, for example, may be distilled at a temperature of at least about 65° C. to distill off THF, and at a temperature of at least about 89° C. to distill off triethylamine. The preferred distillation temperature will, in part, depend on $R^5$. If $R^5$ is tert-butyloxycarbonyl, for example, the distillation temperature preferably does not exceed about 80° C. Where, however, $R^5$ is acetyl, a distillation temperature of about 100° C. or greater is often preferred. The heating is preferably continued until at least about 99% of the protected pyrazole has been consumed. Typically, the heating is maintained for at least about 4 hours.

In some preferred embodiments, the de-protected pyrazole is preferably crystallized directly from the de-protection reaction mixture. This crystallization may be achieve, for example, by adding water, reducing the pH, and cooling. The amount of water may vary widely, but preferably is from about 1 to about 10 ml (more preferably from about 2 to about 6 ml, and even more preferably from about 3 to about 5 ml) per gram of hydrazone reagent used to make the protected pyrazole. The temperature of the resulting mixture is preferably decreased to a temperature of no greater than about 50° C., and an acid (preferably a mineral acid, and more preferably HCl) is added to the mixture to decrease the pH to from about 11 to about 12. The mixture is then cooled to a temperature of less than 20° C. (more preferably less than 10° C., and more preferably no greater than about 5° C.), and then stirred while being maintained within that temperature range.

The resulting solids preferably are filtered, washed (preferably with water), and dried. The drying may comprise, for example, heating the solids (e.g., 80° C. at 29 in Hg).

B-6(B). Deprotection Using an Acid

In some embodiments, the protected pyrazole intermediate is de-protected using an acid. In these embodiments, from about 2 to about 12 mole equivalents, and more preferably about 8.0 mole equivalents, of acid (based on moles of protected pyrazole intermediate) is slowly added to the mixture to remove the protecting groups of the pyrazole intermediate. Although many acids may be suitable, the acid preferably has a pKa of no greater than about −3. In a particularly preferred embodiment, the acid comprises a mineral acid, such as HCl or $H_2SO_4$, with HCl generally being more preferred. If the acid comprises HCl, the solvent preferably is toluene. THF, for example, tends to react with HCl to form chlorobutyl alcohol, which, in turn, acts as an alkylating agent that may form additional impurities. Although this invention contemplates use of a co-solvent (e.g., an alcohol, such as, for example, ethanol), this reaction is typically carried out in the absence of a co-solvent.

In some preferred embodiments, the de-protection reaction mixture is maintained at a temperature that is less than 65° C. In some such preferred embodiments, the reaction mixture is maintained at a temperature of less than about 30° C., and more preferably at room temperature, for preferably at least about 1 hour. In some other preferred embodiments, the reaction mixture is maintained at a temperature of from about 25 to about 100° C., more preferably from about 65 to about 75° C., and even more preferably about 70° C., for from about 1.5 to about 3 hours, more preferably from about 2.0 to about 2.5 hours, and even more preferably about 2 hours. After such heating, the mixture preferably is cooled to from about 20 to about 35° C., and more preferably about 25° C.

Following the de-protection (including any displacement reaction), the majority of the pyrazole is in the aqueous phase of the mixture. Additional water is preferably added, and the resulting mixture is agitated (e.g., stirred) for from about 10 to about 60 minutes, and more preferably about 20 minutes. The organics are then preferably removed from the aqueous layer. In a preferred embodiment, from about 7 to about 9 mole equivalents, and more preferably about 8.2 mole equivalents, of base (based on moles of protected pyrazole intermediate) are then slowly added to the mixture until the pH is from about 11 to about 13, and more preferably about 12.6. The base may be, for example, sodium acetate, potassium acetate, potassium hydroxide, or sodium hydroxide, with sodium hydroxide being preferred. After base addition is complete, the mixture preferably is slowly heated to a temperature of greater than 25° C., more preferably to from about 65 to about 80° C., and even more preferably to about 75° C. The heating is then preferably continued for at least about 1 hour, more preferably from about 1 to about 3 hours, even more preferably from about 1.5 to about 2 hours, and still even more preferably about 2 hours. The mixture preferably is subsequently cooled to from about 0° C. to room temperature (more preferably to about 2° C.) over from about 2 to about 5 hours (more preferably about 3 hours), and then maintained at from about 0° C. to room temperature (more preferably about 2° C.) for from about 2 to about 6 hours (more preferably about 4 hours). The precipitate may be collected using, for example, filtration (with, for example, a 4 micron filter cloth) or centrifugation. The resulting cake is preferably washed with deionized water (preferably a plurality of times) and acetonitrile. The cake may be air-dried until a constant weight is achieved. If necessary, the cake may alternatively (or additionally) be dried under vacuum at a temperature of from room temperature to about 70° C.

B-6(C). De-Protection Where $R^4$ is Other than Hydrogen

As noted above, where the desired compound has a non-hydrogen $R^4$ substituent, it is often preferred that the carbon to be bonded to the $R^4$ substituent be bonded to a methylthio group ("—$SCH_3$") in the methylheteroaryl reagent (discussed above in connection with the ketone preparation). In other words, the one of $Y^1$, $Y^2$, $Y^3$, $Y^4$, and $Y^5$ that is desired to be $=C(R^4)$— is preferably $=C(SCH_3)$— (this is particularly preferred where the desired $R^4$ substituent is an amine or oxide). In instances where such a methylthio group is used, the above de-protection protocol is preferably modified to also displace the methylthio group using a suitable reagent for attaching the desired $R^4$ substituent. Thus, for example, where $R^4$ is at the two position of a pyrimidinyl group, the protected pyrazole may be simultaneously de-protected while displacing the methylthio group with the desired $R^4$ substituent using the following general scheme:

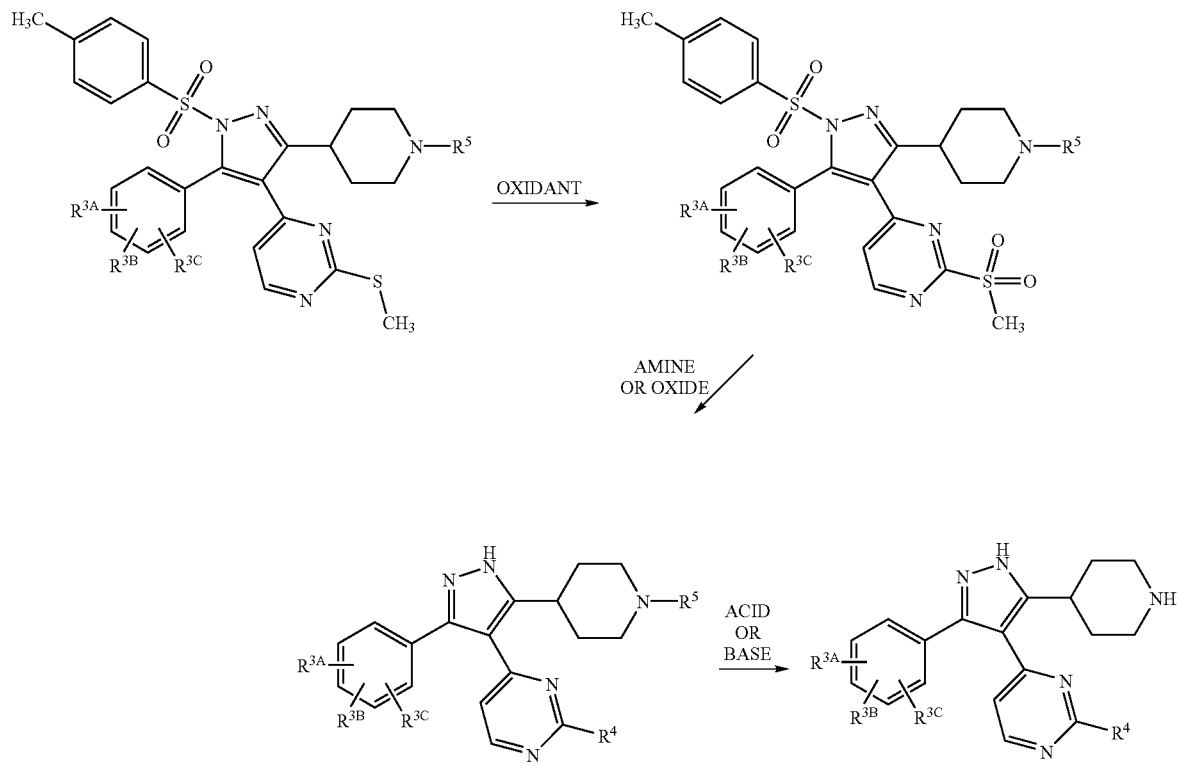

As can be seen from this scheme, the methylthio group is preferably first oxidized to methylsulfonyl with an oxidant (e.g., oxone®, $H_2O_2$, or 3-chloroperbenzoic acid ("mCPBA")) in a suitable solvent, such as dichloromethane, acetonitrile, and/or tetrahydrofuran. After the oxidation, the methylsulfonyl group is preferably displaced with a suitable reagent (typically an amine or oxide) in a suitable solvent, such as tetrahydrofuran, dioxane, dimethylformamide, or acetonitrile. An oxide reagent can typically be generated from its respective alcohol with a suitable base (e.g., LiH-MDS, NaH, LDA, or tBuOK) in a suitable solvent, such as tetrahydrofuran, dioxane, or dimethylformamide. The displacement reaction preferably is conducted at a temperature of from about 20 to about 200° C. Under these conditions, the tosyl protecting group at the 1-position of the pyrazole typically will simultaneously be removed. The de-protection of the piperidinyl group may subsequently be accomplished with trifluoroacetic acid or HCl in a solvent such as dichloromethane or dioxane. In a typically more preferred embodiment, however, the de-protection of the piperidinyl group is accomplished by using the de-protection protocols discussed above for protected pyrazole intermediates generally.

B-6(D). Acetonitrile Trituration of the De-Protected Pyrazole

In some embodiments, the de-protected pyrazole cake is preferably triturated with acetonitrile. This trituration tends to advantageously cause a polymorph transformation that improves the physical characteristics of the de-protected pyrazole intermediate for downstream processes. In a preferred embodiment, acetonitrile is added to the de-protected pyrazole solids in an amount such that the ratio of acetonitrile to solids is at least about 4:1 (ml:grams), more preferably from about 3:1 to about 8:1 (ml:grams), and even more preferably about 5:1 (ml:grams). The mixture is then preferably heated to a temperature that is greater than 25° C., more preferably to at least about 75° C., even more preferably to from about 80 to about 82° C., and still even more preferably to reflux. This heating preferably is continued for at least about 1 hour, more preferably from about 1 to about 6 hours, and even more preferably about 1 hour. The mixture is then preferably cooled to a temperature of no greater than about 30° C., more preferably to from about 2 to about 20° C., even more preferably from about 2 to less than 20° C., and still even more preferably to about 5° C., for at least about 15 minutes, more preferably from about 0.5 to about 2 hours, and even more preferably for about 0.5 hour. The solids are then preferably collected using, for example, filtration (with, for example, a 4 micron filter cloth) or centrifugation. Afterward, the solids are preferably washed with acetonitrile, and then optionally dried. Drying may be achieved by, for example, air drying to a constant weight or by heating the solids to a temperature of at least about 50° C., more preferably to from about 40 to about 85° C., and even more preferably to about 85° C. This heating may optionally be conducted under a vacuum. The concentration of de-protected pyrazole in the resulting cake preferably is at least about 95% (by weight), more preferably at least about 96% (by weight), and even more preferably at least about 99% (by weight).

B-7. Formation of the Desired N-(2-hydroxyacetyl)-5-(4-piperidyl)pyrazole

The de-protected pyrazole intermediate is preferably reacted with a glycolic acid ester to form the desired N-(2-hydroxyacetyl)-5-(4-piperidyl)pyrazole:

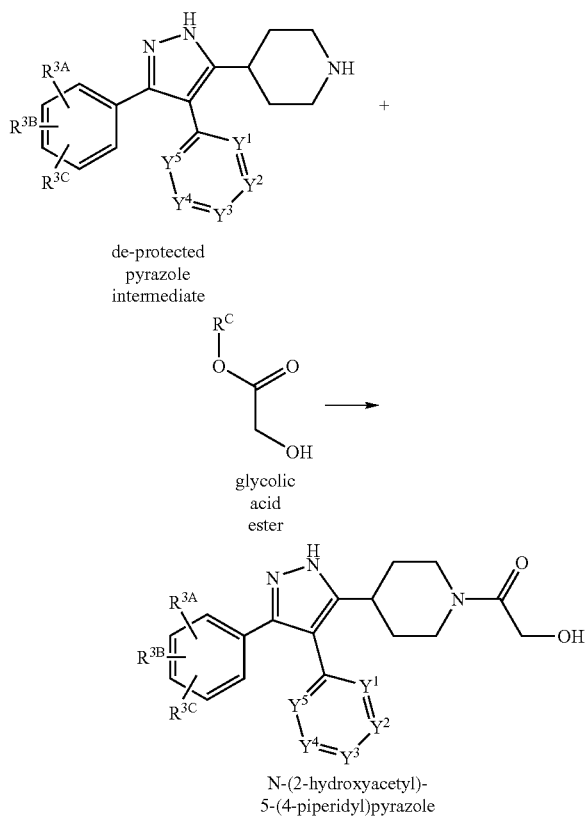

de-protected pyrazole intermediate glycolic acid ester

N-(2-hydroxyacetyl)-5-(4-piperidyl)pyrazole

In a preferred embodiment, a solvate form of the N-(2-hydroxyacetyl)-5-(4-piperidyl)pyrazole product is formed. This is especially preferable where the N-(2-hydroxyacetyl)-5-(4-piperidyl)pyrazole is N-(2-hydroxyacetyl)-5-(4-piperidyl)-4-(4-pyrimidinyl)-3-(4-chlorophenyl)pyrazole. As discussed below, the 1-methyl-2-pyrrolidinone ("N-methylpyrrolidinone" or "NMP") solvate of N-(2-hydroxyacetyl)-5-(4-piperidyl)-4-(4-pyrimidinyl)-3-(4-chlorophenyl)pyrazole is often particularly preferred. In that instance, it is often also preferable to further convert the solvate into another crystalline form, particularly Form I crystalline N-(2-hydroxyacetyl)-5-(4-piperidyl)-4-(4-pyrimidinyl)-3-(4-chlorophenyl)pyrazole.

The glycolic acid ester preferably is $C_1$–$C_6$-alkyl glycolate (i.e., $R^C$ in the above reaction is $C_1$–$C_6$-alkyl), more preferably ethyl glycolate or butyl glycolate, and even more preferably butyl glycolate. The preference for butyl glycolate stems from, for example, its low cost and the fact that it has a boiling point that is above the preferred temperature for the reaction.

The de-protected pyrazole is preferably charged to a reactor with about 2.0 to about 8.0 mole equivalents, more preferably from about 2.0 to about 3.0 mole equivalents, and even more preferably from about 2.5 to about 2.6 mole equivalents of the glycolic acid ester in the presence of a solvent or with neat glycolic acid ester (i.e., without a solvent). Where a solvent is used, it preferably comprises a polar, aprotic solvent and/or alcohol. The solvent preferably is such that the N-(2-hydroxyacetyl)-5-(4-piperidyl)pyrazole is substantially soluble at elevated temperatures (e.g., at least about 60° C. for alcohols and 115° C. for aprotic solvents where the N-(2-hydroxyacetyl)-5-(4-piperidyl) pyrazole is N-(2-hydroxyacetyl)-5-(4-piperidyl)-4-(4-pyrimidinyl)-3-(4-chlorophenyl)pyrazole. The solubility of the N-(2-hydroxyacetyl)-5-(4-piperidyl)pyrazole at elevated temperatures is preferably sufficient to provide at least about 10% (by weight) solution, more typically at least about 15% (by weight) solution, and even more typically at least about 20% (by weight) solution of N-(2-hydroxyacetyl)-5-(4-piperidyl)pyrazole in the solvent. The solubility of the N-(2-hydroxyacetyl)-5-(4-piperidyl)pyrazole at room temperature is preferably less than about 5% (by weight) solution, more typically from about 0.1 to about 5% (by weight) solution, and even more typically from about 1 to about 3% (by weight) solution of the N-(2-hydroxyacetyl)-5-(4-piperidyl) pyrazole in the solvent. Such solvents include, for example, dimethylformamide ("DMF") and/or NMP (particularly where the N-(2-hydroxyacetyl)-5-(4-piperidyl)pyrazole is N-(2-hydroxyacetyl)-5-(4-piperidyl)-4-(4-pyrimidinyl)-3-(4-chlorophenyl)pyrazole). Other solvents that may be suitable include, for example, xylenes. Suitable solvents hypothetically also may include dimethylsulfoxide ("DMSO"). The preferred amount of solvent will vary from solvent to solvent. Typically, from about 1:1 to about 8:1 (mL of solvent:gram of de-protected pyrazole), more typically from about 2:1 to about 4:1 (mL:g), and even more typically from about 2:1 to about 3:1 (mL:g) of the solvent are preferably present. Generally, the preferred solvent is NMP. Thus, the remaining discussion will illustrate the invention using NMP as the solvent.

The reaction may be conducted under standard peptide coupling conditions as described in Schemes D-1 and D-2 and Example D-1 (Step 5) in PCT Publication No. WO 00/31063. In generally more preferred embodiments, however, the reaction is conducted in the presence of 1,8-diazabicyclo[5.4.0]undec-7-ene ("DBU") and/or 1,5-diazabicyclo[4.3.0]non-5-ene, with 1,8-diazabicyclo[5.4.0] undec-7-ene being particularly preferred. It is hypothesized that N,N,N'N'-tetraethyl-N"-cyclohexylguanidine may alternatively be used. Preferably at least about 0.05 mole equivalents, more preferably from about 0.1 to about 0.4 mole equivalents, and even more preferably about 0.1 mole equivalents of the catalyst (preferably 1,8-diazabicyclo [5.4.0]undec-7-ene) are present (based on moles of de-protected pyrazole).

After charging the ingredients to the reactor, the resulting mixture is preferably stirred while being heated to a temperature of greater than 25° C., more preferably to at least about 60° C., even more preferably to from about 90 to about 150° C. In some embodiments, for example, the preferred temperature is about 110° C., while in other embodiments, the preferred temperature is from about 135 to about 140° C. The heating is preferably continued until no greater than 5% (more preferably less than about 4%, even more preferably less than about 3%, still even more preferably less than about 2%, and still yet even more preferably less than about 0.5%) of the starting material remains in the reaction mixture. The amount of starting material may be detected in real time using, for example, liquid chromatographic analysis. Normally, the heating continues for at least about 2 hours, and more typically from about 2 to about 4 hours. In some embodiments, for example, the heating continues for from about 2 to about 3 hours, with a period of about 3 hours being particularly preferred. In other embodiments, the preferred heating time is about 4 hours.

In many preferred embodiments, it is preferable to form a solvate of the N-(2-hydroxyacetyl)-5-(4-piperidyl)pyrazole. In such instances, the mixture preferably is cooled to a temperature of no greater than about 80° C., more preferably to from about 20° C. to about 60° C., and even more preferably to about 25° C. over a time period of at least about 30 minutes, more preferably from about 1 to about 2 hours, and even more preferably about 1 hour. After this initial cooling period, the mixture is preferably cooled to a temperature of less than 20° C., more preferably to from about 0 to about 5° C., and even more preferably to about 0° C. over a time period of at least about 15 minutes, more preferably from about 30 to about 60 minutes, and even more preferably about 30 minutes. This cooling is preferably continued for at least about 1 hour, more preferably from about 1 to about 2 hours, and even more preferably about 2 hours.

In a particularly preferred embodiment, an anti-solvent is added while the mixture is being cooled. In a particularly preferred embodiment, the anti-solvent is added to the mixture during the first cooling period, particularly at the end of the first cooling period. The anti-solvent preferably is a polar solvent, and may be, for example, water, ethyl acetate, methanol, isopropyl alcohol, butanol (e.g., 1-butanol), and/or ethanol. In some embodiments, ethanol is particularly preferred, while in others butanol is particularly preferred. Preferably, from about 0.2:1 to about 10:1 (ml of anti-solvent:grams de-protected pyrazole). In some embodiments (particularly in some where the anti-solvent is ethanol), the amount of anti-solvent is preferably from about 0.2:1 to about 0.3:1 (ml of anti-solvent:grams de-protected pyrazole), and more preferably about 0.22:1 (ml of anti-solvent:grams de-protected pyrazole). In other embodiments (particularly in some embodiments where the anti-solvent is 1-butanol), the amount of anti-solvent is preferably from about 1:1 to about 3:1 (ml of anti-solvent:grams de-protected pyrazole), and more preferably about 2:1 (ml of anti-solvent:grams de-protected pyrazole).

In some embodiments where an anti-solvent is added, the cooling is continued for from about 1 to about 6 hours, and more preferably about 1 hour. The mixture then preferably is cooled further over from about 15 minutes to about 5 hour (more preferably about 30 minutes) to a temperature of from about −5 to about 30° C. (more preferably to from about 0 to about 2° C.), and maintained at that temperature for from about 1 to about 24 hours, and more preferably about 2 hours.

The resulting solids are preferably collected via, for example, filtration (with, for example, 4 micron filter cloth) or centrifugation, washed at least once (preferably 2 times) with a solvent (e.g., NMP or ethyl acetate) and/or anti-solvent, and dried. The resulting cake preferably contains at least about 95% (by weight), more preferably at least about 98% (by weight), and even more preferably at least about 99% by weight solvate. The amount of NMP to N-(2-hydroxyacetyl)-5-(4-piperidyl)pyrazole in the solvate is typically from less than about 200 ppm (or 0.02% (by weight)) to about a molar ratio of about 1:1 (particularly where the solvate is an NMP solvate).

In many preferred embodiments where the N-(2-hydroxyacetyl)-5-(4-piperidyl)pyrazole is N-(2-hydroxyacetyl)-5-(4-piperidyl)-4-(4-pyrimidinyl)-3-(4-chlorophenyl)pyrazole, the NMP solvate is isolated and then converted to Form I crystalline N-(2-hydroxyacetyl)-5-(4-piperidyl)-4-(4-pyrimidinyl)-3-(4-chlorophenyl)pyrazole.

In a particularly preferred embodiment, the solvate is charged to a reactor with a polar solvent. Such a solvent may be, for example, water, ethyl acetate, methanol, isopropyl alcohol, and/or ethanol, and is preferably ethanol (particularly where ethanol was the anti-solvent added to the solvate mixture during cooling). Preferably, from about 50:1 to about 5:1 (ml solvent:gram NMP solvate solids), more preferably from about 10:1 to about 8:1 (ml solvent:gram NMP solvate solids), and even more preferably about 9:1 (ml solvent:gram NMP solvate solids). In addition to the solvent, from about 0.01 to about 0.4 equivalents, and more preferably from about 0.09 to about 0.12 equivalents, of DBU (based on moles of N-(2-hydroxyacetyl)-5-(4-piperidyl)pyrazole) may optionally be charged to the reactor. The presence of this small amount of DBU tends to be, for example, advantageous for saponifying any bis-glycolate impurity present in the mixture.

The solvate/solvent mixture preferably is heated to a temperature of greater than 25° C., more preferably to at least about 50° C., even more preferably to from about 50 to about 80° C., and still even more preferably to reflux. The heating is preferably continued for at least 1 hour, more preferably from about 1 hour to about 5 hours, and still even more preferably about 4 hours. Although Applicants have found that 1 hour is typically sufficient (particularly at reflux where ethanol is the solvent) to convert the solvate to Form 1 crystalline N-(2-hydroxyacetyl)-5-(4-piperidyl)-4-(4-pyrimidinyl)-3-(4-chlorophenyl)pyrazole, Applicants have found that additional heating may often be advantageous for obtaining a purer product.

Following the heating, the mixture preferably is cooled to a temperature of less than 30° C., more preferably to from about 0 to about 30° C., and even more preferably to about 15° C. over a time period of at least about 1 hour, more preferably from about 1.5 to about 5 hours, and even more preferably about 3 hours. Afterward, the solids are collected using, for example, filtration (preferably with a 4 micron filter cloth) or centrifugation. The cake is then preferably washed (preferably in a displacement wash) at least once (and more preferably at least twice) with a polar solvent (preferably the solvent used during the reflux), and then dried. The cake preferably contains less than about 500 ppm of NMP, more preferably less than 300 ppm of NMP, and even more preferably less than 250 ppm of NMP.

C. Tautomeric Forms of the Compounds of this Invention

The present invention also is directed to the tautomeric forms of compounds of Formula (I). As illustrated below, the pyrazoles of Formulas (A) and (B) are magnetically and structurally equivalent because of the prototropic tautomeric nature of the hydrogen:

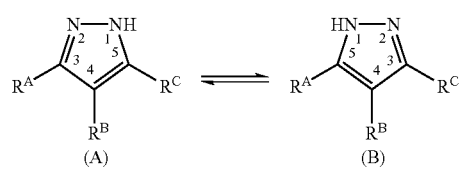

D. Compounds of this Invention Having One or More Asymmetric Carbons

The present invention also comprises compounds of Formula (I) having one or more asymmetric carbons. It is known to those skilled in the art that those pyrazoles of the present invention having asymmetric carbon atoms may exist in diastereomeric, racemic, or optically active forms.

All of these forms are contemplated within the scope of this invention. More specifically, the present invention includes enantiomers, diastereomers, racemic mixtures, and other mixtures thereof.

E. Salts of the Compounds of this Invention

The compounds of this invention may be used in the form of salts derived from inorganic or organic acids. Depending on the particular compound (and/or its crystalline structure), a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically-acceptable. Pharmaceutically-acceptable salts include salts commonly used to form alkali metal salts and to form addition salts of free acids or free bases. In general, these salts typically may be prepared by conventional means with a compound of this invention by reacting, for example, the appropriate acid or base with the compound.

Pharmaceutically-acceptable acid addition salts of the compounds of this invention may be prepared from an inorganic or organic acid. Examples of suitable inorganic acids include hydrochloric, hydrobromic acid, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenyipropionate, picrate, pivalate, thiocyanate, tosylate, and undecanoate.

Pharmaceutically-acceptable base addition salts of the compounds of this invention include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts may be made from amines, such as tromethamine, diethylamine, N,N'-dibenzylethylenediamine, chloroprocaine, diethanolamine, ethylenediamine, meglumine (N-methylglucamine), and procaine. Basic nitrogen-containing groups may be quaternized with agents such as lower alkyl ($C_1$–$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

Particularly preferred salts of the compounds of this invention include hydrochloric acid (HCl) salts, trifluoroacetate ($CF_3COOH$ or "TFA") salts, mesylate salts, and tosylate salts.

F. Preventing or Treating Conditions Using the Compounds Prepared by this Invention This invention is directed, in part, to a method for preventing or treating a condition (typically a pathological condition) in a mammal (e.g., a human, companion animal, farm animal, laboratory animal, zoo animal, or wild animal) having or disposed to having such a condition.

Some embodiments of this invention are directed to a method for preventing or treating a p38-mediated condition. As used herein, the term "p38-mediated condition" refers to any condition (particularly pathological conditions, i.e., diseases and disorders) in which p38 kinase (particularly p38α kinase) plays a role, either by control of p38 kinase itself, or by p38 kinase causing another factor to be released, such as, for example, IL-1, IL-6, or IL-8. A disease state in which, for instance, IL-1 is a major component, and whose production or action is exacerbated or secreted in response to p38, would therefore be considered a disorder mediated by p38.

The compounds of this invention generally tend to be useful for treating or preventing pathological conditions that include, but are not limited to:

(a) inflammation;

(b) arthritis, such as rheumatoid arthritis, spondyloarthropathies, gouty arthritis, osteoarthritis, systemic lupus erythematosus arthritis, juvenile arthritis, osteoarthritis, and gouty arthritis;

(c) neuroinflammation;

(d) pain (i.e., use of the compounds as analgesics), such as neuropathic pain;

(e) fever (i.e., use of the compounds as antipyretics);

(f) pulmonary disorders or lung inflammation, such as adult respiratory distress syndrome, pulmonary sarcoidosis, asthma, silicosis, and chronic pulmonary inflammatory disease;

(g) cardiovascular diseases, such as atherosclerosis, myocardial infarction (such as post-myocardial infarction indications), thrombosis, congestive heart failure, cardiac reperfusion injury, and complications associated with hypertension and/or heart failure such as vascular organ damage;

(h) cardiomyopathy;

(i) stroke, such as ischemic and hemorrhagic stroke;

(j) ischemia, such as brain ischemia and ischemia resulting from cardiac/coronary bypass;

(k) reperfusion injury;

(l) renal reperfusion injury;

(m) brain edema;

(n) neurotrauma and brain trauma, such as closed head injury;

(o) neurodegenerative disorders;

(p) central nervous system disorders (these include, for example, disorders having an inflammatory or apoptotic component), such as Alzheimer's disease, Parkinson's disease, Huntington's Disease, amyotrophic lateral sclerosis, spinal cord injury, and peripheral neuropathy;

(q) liver disease and nephritis;

(r) gastrointestinal conditions, such as inflammatory bowel disease, Crohn's disease, gastritis, irritable bowel syndrome, and ulcerative colitis;

(s) ulcerative diseases, such as gastric ulcer;

(t) ophthalmic diseases, such as retinitis, retinopathies (such as diabetic retinopathy), uveitis, ocular photophobia, nonglaucomatous optic nerve atrophy, and age-related macular degeneration (ARMD) (such as ARMD-atrophic form);

(u) ophthalmological conditions, such as corneal graft rejection, ocular neovascularization, retinal neovascularization (such as neovascularization following injury or infection), and retrolental fibroplasia;

(v) glaucoma, such as primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation, and corticosteroid-induced glaucoma;

(w) acute injury to the eye tissue and ocular traumas, such as post-traumatic glaucoma, traumatic optic neuropathy, and central retinal artery occlusion (CRAO);

(x) diabetes;

(y) diabetic nephropathy;

(z) skin-related conditions, such as psoriasis, eczema, burns, dermatitis, keloid formation, scar tissue formation, and angiogenic disorders;

(aa) viral and bacterial infections, such as sepsis, septic shock, gram negative sepsis, malaria, meningitis, opportunistic infections, cachexia secondary to infection or malignancy, cachexia secondary to acquired immune deficiency syndrome (AIDS), AIDS, ARC (AIDS related complex), pneumonia, and herpes virus;

(bb) myalgias due to infection;

(cc) influenza;

(dd) endotoxic shock;

(ee) toxic shock syndrome;

(ff) autoimmune disease, such as graft vs. host reaction and allograft rejections;

(gg) bone resorption diseases, such as osteoporosis;

(hh) multiple sclerosis;

(ii) disorders of the female reproductive system, such as endometriosis;

(jj) pathological, but non-malignant, conditions, such as hemaginomas (such as infantile hemaginomas), angiofibroma of the nasopharynx, and avascular necrosis of bone;

(kk) benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer, skin cancer such as squamus cell and basal cell cancers, prostate cancer, renal cell carcinoma, and other known cancers that affect epithelial cells throughout the body;

(ll) leukemia;

(mm) lymphoma, such as B cell lymphoma;

(nn) systemic lupus erthrematosis (SLE);

(oo) angiogenesis including neoplasia; and (pp) metastasis.

Some embodiments of this invention are alternatively (or additionally) directed to a method for preventing or treating a TNF-mediated condition. As used herein, the term "TNF-mediated condition" refers to any condition (particularly pathological conditions, i.e., diseases or disorders) in which TNF plays a role, either by control of TNF itself, or by TNF causing another monokine to be released, such as, for example, IL-1, IL-6, and/or IL-8. A disease state in which, for instance, IL-1 is a major component and whose production or action is exacerbated or secreted in response to TNF, would therefore be considered a disorder mediated by TNF.

Examples of TNF-mediated conditions include inflammation (e.g., rheumatoid arthritis), autoimmune disease, graft rejection, multiple sclerosis, a fibrotic disease, cancer, an infectious disease (e.g., malaria, mycobacterial infection, meningitis, etc.), fever, psoriasis, a cardiovascular disease (e.g., post-ischemic reperfusion injury and congestive heart failure), a pulmonary disease, hemorrhage, coagulation, hyperoxic alveolar injury, radiation damage, acute phase responses like those seen with infections and sepsis and during shock (e.g., septic shock, hemodynamic shock, etc.), cachexia, and anorexia. Such conditions also include infectious diseases. Such infectious diseases include, for example, malaria, mycobacterial infection, meningitis. Such infectious diseases also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

As TNF-$\beta$ has close structural homology with TNF-$\alpha$ (also known as cachectin), and because each induces similar biologic responses and binds to the same cellular receptor, the synthesis of both TNF-$\alpha$ and TNF-$\beta$ tend to be inhibited by the compounds of this invention and thus are herein referred to collectively as "TNF" unless specifically delineated otherwise.

Some embodiments of this invention are alternatively (or additionally) directed to a method for preventing or treating a cyclooxygenase-2-mediated condition. As used herein, the term "cyclooxygenase-2-mediated condition" refers to any condition (particularly pathological conditions, i.e., diseases and disorders) in which cyclooxygenase-2 plays a role, either by control of cyclooxygenase-2 itself, or by cyclooxygenase-2 causing another factor to be released. Many cyclooxygenase-2-mediated conditions are known in the art, and include, for example, inflammation and other cyclooxygenase-mediated disorders listed by Carter et al. in U.S. Pat. No. 6,271,253.

In some embodiments of particular interest, the condition treated or prevented by the methods of this invention comprises inflammation.

In some embodiments of particular interest, the condition treated or prevented by the methods of this invention comprises arthritis.

In some embodiments of particular interest, the condition treated or prevented by the methods of this invention comprises rheumatoid arthritis.

In some embodiments of particular interest, the condition treated or prevented by the methods of this invention comprises asthma.

In some embodiments of particular interest, the condition treated or prevented by the methods of this invention comprises a coronary condition.

In some embodiments of particular interest, the condition treated or prevented by the methods of this invention comprises bone loss.

In some embodiments of particular interest, the condition treated or prevented by the methods of this invention comprises B cell lymphoma.

The phrase "preventing a condition" means reducing the risk of (or delaying) the onset of the condition in a mammal that does not have the condition, but is predisposed to having the condition. In contrast, the phrase "treating a condition" means ameliorating, suppressing, or eradicating an existing condition.

A wide variety of methods may be used alone or in combination to administer the pyrazole compounds described above. For example, the compounds may be administered orally, intravascularly (IV), intraperitoneally, subcutaneously, intramuscularly (IM), by inhalation spray, rectally, or topically.

Typically, a compound described in this specification is administered in an amount effective to inhibit p38 kinase (particularly p38α kinase), TNF (particularly TNF-α), and/or cyclooxygenase (particularly cyclooxygenase-2). The preferred total daily dose of the pyrazole compound (administered in single or divided doses) is typically from about 0.01 to about 100 mg/kg, more preferably from about 0.1 to about 50 mg/kg, and even more preferably from about 0.5 to about 30 mg/kg (i.e., mg pyrazole compound per kg body weight). Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular pyrazole compound employed; whether a drug delivery system is utilized; and whether the pyrazole compound is administered as part of a drug combination. Thus, the dosage regimen actually employed can vary widely, and, therefore, can deviate from the preferred dosage regimen set forth above.

The present compounds may be used in co-therapies, partially or completely, in place of other conventional anti-inflammatory, such as together with steroids, cyclooxygenase-2 inhibitors, non-steroidal anti-inflammatory drugs ("NSAIDs"), disease-modifying anti-rheumatic drugs ("DMARDs"), immunosuppressive agents, 5-lipoxygenase inhibitors, leukotriene B4 ("LTB4") antagonists, and leukotriene A4 ("LTA4") hydrolase inhibitors.

G. Pharmaceutical Compositions Containing the Compounds Prepared by this Invention This invention also is directed to pharmaceutical compositions (or "medicaments") comprising the substituted pyrazoles described above (including tautomers of the compounds, and pharmaceutically-acceptable salts of the compounds and tautomers), and to methods for making pharmaceutical compositions comprising those compounds in combination with one or more conventional non-toxic, pharmaceutically-acceptable carriers, diluents, wetting or suspending agents, vehicles, and/or adjuvants (the carriers, diluents, wetting or suspending agents, vehicles, and adjuvants sometimes being collectively referred to in this specification as "carrier materials"); and/or other active ingredients. The preferred composition depends on the method of administration. Formulation of drugs is generally discussed in, for example, Hoover, John E., *Remington's Pharmaceutical Sciences* (Mack Publishing Co., Easton, Pa.: 1975) (incorporated by reference into this specification). See also, Liberman, H. A., Lachman, L., eds., *Pharmaceutical Dosage Forms* (Marcel Decker, New York, N.Y., 1980) (incorporated by reference into this specification). In many preferred embodiments, the pharmaceutical composition is made in the form of a dosage unit containing a particular amount of the active ingredient. Typically, the pharmaceutical composition contains from about 0.1 to 1000 mg (and more typically, 7.0 to 350 mg) of the substituted pyrazole.

Solid dosage forms for oral administration include, for example, hard or soft capsules, tablets, pills, powders, and granules. In such solid dosage forms, the substituted pyrazoles are ordinarily combined with one or more adjuvants. If administered per os, the substituted pyrazoles may be mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation, as may be provided in a dispersion of the compound of this invention in hydroxypropylmethyl cellulose. In the case of capsules, tablets, and pills, the dosage forms also may comprise buffering agents, such as sodium citrate, or magnesium or calcium carbonate or bicarbonate. Tablets and pills additionally may be prepared with enteric coatings.

Liquid dosage forms for oral administration include, for example, pharmaceutically-acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

"Parenteral administration" includes subcutaneous injections, intravenous injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents. Acceptable carrier materials include, for example, water, 1,3-butanediol, Ringer's solution, isotonic sodium chloride solution, bland fixed oils (e.g., synthetic mono- or diglycerides), dextrose, mannitol, fatty acids (e.g., oleic acid), dimethyl acetamide, surfactants (e.g., ionic and non-ionic detergents), and/or polyethylene glycols (e.g., PEG 400).

Formulations for parenteral administration may, for example, be prepared from sterile powders or granules having one or more of the carriers materials mentioned for use in the formulations for oral administration. The substituted pyrazoles may be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

The compounds of this invention preferably make up from about 0.075 to about 30% (w/w) (more preferably 0.2 to 20% (w/w), and even more preferably 0.4 to 15% (w/w)) of a pharmaceutical composition used for topical or rectal administration.

Suppositories for rectal administration may be prepared by, for example, mixing a compound of this invention with a suitable nonirritating excipient that is solid at ordinary temperatures, but liquid at the rectal temperature and will therefore melt in the rectum to release the drug. Suitable excipients include, for example, such as cocoa butter; synthetic mono-, di-, or triglycerides; fatty acids; and/or polyethylene glycols.

"Topical administration" includes transdermal administration, such as via transdermal patches or iontophoresis devices. Compositions for topical administration also include, for example, topical gels, sprays, ointments, and creams.

When formulated in an ointment, the compounds of this invention may be employed with, for example, either a paraffinic or a water-miscible ointment base. When formulated in a cream, the active ingredient(s) may be formulated with, for example, an oil-in-water cream base. If desired, the aqueous phase of the cream base may include, for example at least about 30% (w/w) of a polyhydric alcohol, such as propylene glycol, butane-1,3-diol, mannitol, sorbitol, glycerol, polyethylene glycol, and mixtures thereof.

A topical formulation may include a compound which enhances absorption or penetration of the active ingredient through the skin or other affected areas. Examples of such dermal penetration enhancers include dimethylsulfoxide and related analogs.

When the compounds of this invention are administered by a transdermal device, administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise, for example, a mixture of at least one emulsifier with a fat or an oil or with both a fat and an oil. Preferably, a hydrophilic emulsifier is included together with a lipophilic emulsifier which acts as a stabilizer. It is also preferable to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, given that the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters, for example, may be used. These may be used alone or in combination depending on the properties required. Alternatively, high melting point lipids such as white soft paraffin and/or liquid paraffin or other mineral oils may be used. Formulations suitable for topical administration to the eye also include eye drops wherein the compound of this invention is dissolved or suspended in suitable carrier, typically comprising an aqueous solvent. The compounds of this invention are preferably present in such formulations in a concentration of from about 0.5 to about 20% (w/w) (more preferably 0.5 to 10% (w/w), and often even more preferably about 1.5% (w/w)).

Other carrier materials and modes of administration known in the pharmaceutical art may also be used.

H. Definitions

The term "alkyl" (alone or in combination with another term(s)) means a straight- or branched-chain saturated hydrocarbyl substituent (i.e., a substituent containing only carbon and hydrogen) typically containing from 1 to about 20 carbon atoms, more typically from 1 to about 12 carbon atoms, even more typically from 1 to about 8 carbon atoms, and still even more typically from 1 to about 6 carbon atoms. Examples of such substituents include methyl, ethyl, n-propyl, isopropyl, n-butyl, isobutyl, sec-butyl, tert-butyl, pentyl, iso-amyl, hexyl, and octyl.

The term "alkenyl" (alone or in combination with another term(s)) means a straight- or branched-chain hydrocarbyl substituent containing one or more double bonds and typically from 2 to about 20 carbon atoms, more typically from 2 to about 12 carbon atoms, even more typically from 2 to about 8 carbon atoms, and still even more typically from 2 to about 6 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and decenyl.

The term "alkynyl" (alone or in combination with another term(s)) means a straight- or branched-chain hydrocarbyl substituent containing one or more triple bonds and typically from 2 to about 20 carbon atoms, more typically from 2 to about 12 carbon atoms, even more typically from 2 to about 8 carbon atoms, and still even more typically from 2 to about 6 carbon atoms. Examples of such substituents include ethynyl, 1-propynyl, 2-propynyl, decynyl, 1-butynyl, 2-butynyl, 3-butynyl, and 1-pentynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated carbocyclyl substituent containing from 3 to about 14 carbon ring atoms, more typically from 3 to about 12 carbon ring atoms, and even more typically from 3 to about 8 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be 2 or 3 carbon rings fused together, such as, for example, decalinyl or norpinanyl.

The term "cycloalkylalkyl" (alone or in combination with another term(s)) means alkyl substituted with cycloalkyl. Examples of such substituents include cyclopropylmethyl, cyclobutylmethyl, cyclopentylmethyl, and cyclohexylmethyl.

The term "cycloalkenyl" (alone or in combination with another term(s)) means a partially unsaturated carbocyclyl substituent. Examples of such substituents include cyclobutenyl, cyclopentenyl, and cyclohexenyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, cycloalkyl, cycloalkenyl, aryl, etc.) is indicated by the prefix "$C_x$–$C_y$-", wherein x is the minimum and y is the maximum number of carbon atoms in the substituent. Thus, for example, "$C_1$–$C_6$-alkyl" refers to an alkyl substituent containing from 1 to 6 carbon atoms. Illustrating further, $C_3$–$C_6$-cycloalkyl means a saturated carbocyclyl containing from 3 to 6 carbon ring atoms.

The term "arylalkyl" (alone or in combination with another term(s)) means alkyl substituted with aryl.

The term "benzyl" (alone or in combination with another term(s)) means a methyl radical substituted with phenyl, i.e., the following structure:

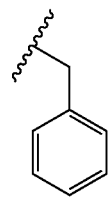

The term "benzene" means the following structure:

The term "hydrogen" (alone or in combination with another term(s)) means a hydrogen radical, and may be depicted as —H.

The term "hydroxy" or "hydroxyl" (alone or in combination with another term(s)) means —OH.

The term "hydroxyalkyl" (alone or in combination with another term(s)) means alkyl substituted with one more hydroxy.

The term "nitro" (alone or in combination with another term(s)) means —$NO_2$.

The term "cyano" (alone or in combination with another term(s)) means —CN, which also may be depicted:

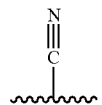

The term "keto" (alone or in combination with another term(s)) means an oxo radical, and may be depicted as =O.

The term "carboxy" or "carboxyl" (alone or in combination with another term(s)) means —C(O)—OH, which also may be depicted as:

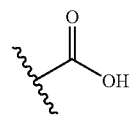

The term "amino" (alone or in combination with another term(s)) means —$NH_2$. The term "monosubstituted amino" (alone or in combination with another term(s)) means an amino substituent wherein one of the hydrogen radicals is replaced by a non-hydrogen substituent. The term "disubstituted amino" (alone or in combination with another term(s)) means an amino substituent wherein both of the hydrogen atoms are replaced by non-hydrogen substituents, which may be identical or different.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I). Typically, a fluorine radical or chlorine radical is preferred, with a fluorine radical often being particularly preferred.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Where there are more than one hydrogens replaced with halogens, the halogens may be the identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 1,1,1-trifluoroethyl, difluoroethyl, pentafluoroethyl, difluoropropyl, dichloropropyl, and heptafluoropropyl. Illustrating further, "haloalkoxy" means an alkoxy substituent wherein at least one hydrogen radical is replaced by a halogen radical. Examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen radical, those halogen radicals may be identical or different (unless otherwise stated).

The term "carbonyl" (alone or in combination with another term(s)) means —C(O)—, which also may be depicted as:

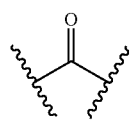

This term also is intended to encompass a hydrated carbonyl substituent, i.e., —$C(OH)_2$—.

The term "aminocarbonyl" (alone or in combination with another term(s)) means —C(O)—$NH_2$, which also may be depicted as:

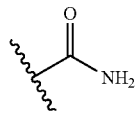

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—CH₃), ethoxy, n-propoxy, isopropoxy, n-butoxy, iso-butoxy, sec-butoxy, and tert-butoxy.

The term "alkylthio" (alone or in combination with another term(s)) means —S-alkyl. For example, "methylthio" is —S—CH₃. Other examples of alkylthio substituents include ethylthio, propylthio, butylthio, and hexylthio.

The term "alkylcarbonyl" or "alkanoyl" (alone or in combination with another term(s)) means —C(O)-alkyl. For example, "ethylcarbonyl" may be depicted as:

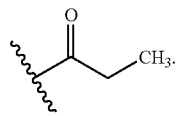

Examples of other often preferred alkylcarbonyl substituents include methylcarbonyl, propylcarbonyl, butylcarbonyl, pentylcarbonyl, and hexylcarbonyl.

The term "aminoalkylcarbonyl" (alone or in combination with another term(s)) means —C(O)-alkyl-NH₂. For example, "aminomethylcarbonyl" may be depicted as:

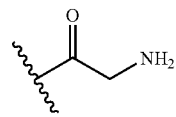

The term "alkoxycarbonyl" (alone or in combination with another term(s)) means —C(O)—O-alkyl. For example, "ethoxycarbonyl" may be depicted as:

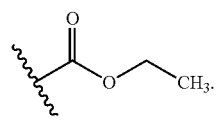

Examples of other often preferred alkoxycarbonyl substituents include methoxycarbonyl, ethoxycarbonyl, propoxycarbonyl, butoxycarbonyl, pentoxycarbonyl, and hexyloxycarbonyl.

The term "carbocyclylcarbonyl" (alone or in combination with another term(s)) means —C(O)-carbocyclyl. For example, "phenylcarbonyl" may be depicted as:

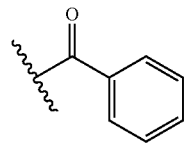

Similarly, the term "heterocyclylcarbonyl" (alone or in combination with another term(s)) means —C(O)-heterocyclyl.

The term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl. For example, "phenyloxycarbonyl" may be depicted as:

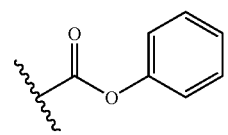

The term "carbocyclylalkoxycarbonyl" (alone or in combination with another term(s)) means —C(O)—O-alkyl-carbocyclyl. For example, "phenylethoxycarbonyl" may be depicted as:

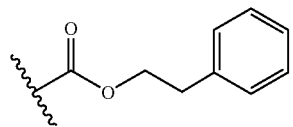

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl.

The term "thiol" (alone or in combination with another term(s)) means a sulfhydryl substituent, and may be depicted as —SH.

The term "sulfonyl" (alone or in combination with another term(s)) means —S(O)₂—, which also may be depicted as:

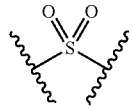

Thus, for example, "alkyl-sulfonyl-alkyl" means alkyl-S(O)₂-alkyl. Examples of typically preferred alkylsulfonyl substituents include methylsulfonyl, ethylsulfonyl, and propylsulfonyl.

The term "aminosulfonyl" (alone or in combination with another term(s)) means —S(O)₂—NH₂, which also may be depicted as:

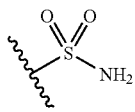

The term "sulfinyl" or "sulfoxido" (alone or in combination with another term(s)) means —S(O)—, which also may be depicted as:

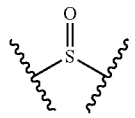

Thus, for example, "alkylsulfinylalkyl" or "alkylsulfoxidoalkyl" means alkyl-S(O)-alkyl. Typically preferred alkylsulfinyl groups include methylsulfinyl, ethylsulfinyl, butylsulfinyl, and hexylsulfinyl.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofurnayl, tetradydrofurnayl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiadiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

A heterocyclyl alternatively may be 2 or 3 rings fused together, wherein at least one such ring contains a heteroatom as a ring atom (i.e., nitrogen, oxygen, or sulfur). Such substituents include, for example, indolizinyl, pyrindinyl, pyranopyrrolyl, 4H-quinolizinyl, purinyl, naphthyridinyl, pyridopyridinyl (including pyrido[3,4-b]-pyridinyl, pyrido [3,2-b]-pyridinyl, or pyrido[4,3-b]-pyridinyl), and pteridinyl. Other examples of fused-ring heterocyclyls include benzo-fused heterocyclyls, such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", or "benzothiofuranyl"), isobenzothienyl (also known as "isobenzothiophenyl", "isothionaphthenyl", or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "2-fused' ring" heterocyclyl (alone or in combination with another term(s)) means a saturated, partially saturated, or aryl heterocyclyl containing 2 fused rings. Examples of 2-fused-ring heterocyclyls include indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as 1,3,5-, 1,2,4- or 1,2,3-tiiazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as 1,2-, 1,4-, 2,3- and 2,1-benzopyronyl, quinolinyl, isoquinolinyl, cinnolinyl, quinazolinyl, and 1,4-benzoxazinyl.

The term "heterocyclylalkyl" (alone or in combination with another term(s)) means alkyl substituted with a heterocyclyl.

The term "heterocycloalkyl" (alone or in combination with another term(s)) means a fully saturated heterocyclyl.

In some preferred embodiments, a carbocyclyl or heterocyclyl optionally is substituted with one or more substituents independently selected from the group consisting of halogen, hydroxy (—OH), cyano (—CN), nitro (—NO$_2$), thiol (—SH), carboxy (—C(O)—OH), amino (—NH$_2$), keto (=O), aminocarbonyl, alkyl, aminoalkyl, carboxyalkyl, alkylamino, alkylaminoalkyl, aminoalkylamino, alkylaminocarbonyl, aminocarbonylalkyl, alkoxycarbonylalkyl, alkenyl, alkynyl, alkylthioalkyl, alkylsulfinyl, alkylsulfinylalkyl, alkylsulfonyl, alkylsulfonylalkyl, alkylthio, carboxyalkylthio, alkylcarbonyl (also known as "alkanoyl"), alkylcarbonyloxy, alkoxy, alkoxyalkyl, alkoxycarbonyl, alkoxycarbonylalkoxy, alkoxyalkylthio, alkoxycarbonylalkylthio, carboxyalkoxy, alkoxycarbonylalkoxy, carbocyclyl, carbocyclylaminocarbonyl, carbocyclylaminoalkyl, carbocyclylalkoxy, carbocyclyloxyalkyl, carbocyclylalkoxyalkyl, carbocyclylthioalkyl, carbocyclylsulfinylalkyl, carbocyclylsulfonylalkyl, carbocyclylalkyl, carbocyclyloxy, carbocyclylthio, carbocyclylalkylthio, carbocyclylamino, carbocyclylalkylamino, carbocyclylcarbonylamino, carbocyclylcarbonyl, carbocyclylalkyl, carbocyclylcarbonyloxy, carbocyclyloxycarbonyl, carbocyclylalkoxycarbonyl, carbocyclyloxyalkoxycarbocyclyl, carbocyclylthioalkylthiocarbocyclyl, carbocyclylthioalkoxycarbocyclyl, carbocyclyloxyalkylthiocarbocyclyl, heterocyclyl, heterocyclylaminocarbonyl, heterocyclylaminoalkyl, heterocyclylalkoxy, heterocyclyloxyalkyl, heterocyclylalkoxyalkyl, heterocyclylthioalkyl, heterocyclylsulfinylalkyl, heterocyclylsulfonylalkyl, heterocyclylalkyl, heterocyclyloxy, heterocyclylthio, heterocyclylalkylthio, heterocyclylamino, heterocyclylalkylamino, heterocyclylcarbonylamino, heterocyclylcarbonyl, heterocyclylalkylcarbonyl, heterocyclyloxycarbonyl, heterocyclylcarbonyloxy, heterocyclylalkoxycarbonyl, heterocyclyloxyalkoxyheterocyclyl, heterocyclylthioalkylthioheterocyclyl, heterocyclylthioalkoxyheterocyclyl, and heterocyclyloxyalkylthioheterocyclyl.

In some preferred embodiments, a carbocyclyl or heterocyclyl optionally is substituted with one or more substituents independently selected from the group consisting of halogen, hydroxy, cyano, nitro, thiol, carboxy, amino, aminocarbonyl, $C_1$–$C_6$-alkyl, amino-$C_1$–$C_6$-alkyl, keto, carboxy-$C_1$–$C_6$-alkyl, $C_1$–$C_6$-alkylamino, $C_1$–$C_6$-alkylamino-$C_1$–$C_6$-alkyl, amino-$C_1$–$C_6$-alkylamino, $C_1$–$C_6$-alkylaminocarbonyl, aminocarbonyl-$C_1$–$C_6$-alkyl, $C_1$–$C_6$-alkoxycarbonyl-$C_1$–$C_6$-alkyl, $C_2$–$C_6$-alkenyl, $C_2$–$C_6$-alkynyl, $C_1$–$C_6$-alkylthio-$C_1$–$C_6$-alkyl, $C_1$–$C_6$-alkylsulfinyl, $C_1$–$C_6$-alkylsulfinyl-$C_1$–$C_6$-alkyl, $C_1$–$C_6$-alkylsulfonyl, $C_1$–$C_6$-alkylsulfonyl-$C_1$–$C_6$-alkyl, $C_1$–$C_6$-alkylthio, carboxy-$C_1$–$C_6$-alkylthio, $C_1$–$C_6$-alkylcarbonyl, $C_1$–$C_6$-alkylcarbonyloxy, $C_1$–$C_6$-alkoxy, $C_1$–$C_6$-alkoxy-$C_1$–$C_6$-alkyl, $C_1$–$C_6$-alkoxycarbonyl, $C_1$–$C_6$-alkoxycarbonyl-$C_1$–$C_6$-alkoxy, $C_1$–$C_6$-alkoxy-$C_1$–$C_6$-alkylthio, $C_1$–$C_6$-alkoxycarbonyl-$C_1$–$C_6$-alkylthio, carboxy-$C_1$–$C_6$-alkoxy, $C_1$–$C_6$-alkoxycarbonyl-$C_1$–$C_6$-alkoxy, aryl, arylaminocarbonyl, arylamino-$C_1$–$C_6$-alkyl, aryl-$C_1$–$C_6$-alkoxy, aryloxy-$C_1$–$C_6$-alkyl, aryl-$C_1$–$C_6$-alkoxy-$C_1$–$C_6$-alkyl, arylthio-$C_1$–$C_6$-alkyl, arylsulfinyl-$C_1$–$C_6$-alkyl, arylsulfonyl-$C_1$–$C_6$-alkyl, aryl-$C_1$–$C_6$-alkyl, aryloxy, arylthio, aryl-$C_1$–$C_6$-alkylthio, arylamino, aryl-$C_1$–$C_6$-alkylamino, arylcarbonylamino, arylcarbonyl, aryl-$C_1$–$C_6$-alkylcarbonyl, arylcarbonyloxy, aryloxycarbonyl, aryl-$C_1$–$C_6$-alkoxycarbonyl, aryloxy-$C_1$–$C_6$-alkoxyaryl, arylthio-$C_1$–$C_6$-alkylthioaryl, arylthio-$C_1$–$C_6$-alkoxyaryl, aryloxy-$C_1$–$C_6$-alkylthioaryl, cycloalkyl, cycloalkyl aminocarbonyl, cycloalkyl amino-$C_1$–$C_6$-alkyl, cycloalkyl-$C_1$–$C_6$-alkoxy, cycloalkyl oxy-$C_1$–$C_6$-alkyl, cycloalkyl-$C_1$–$C_6$-alkoxy-$C_1$–$C_6$-alkyl, cycloalkyl thio-$C_1$–$C_6$-alkyl, cycloalkyl sulfinyl-$C_1$–$C_6$-alkyl, cycloalkyl sulfonyl-$C_1$–$C_6$-alkyl, cycloalkyl-$C_1$–$C_6$-alkyl, cycloalkyloxy, cycloalkylthio, cycloalkyl-$C_1$–$C_6$-alkylthio, cycloalkylamino, cycloalkyl-$C_1$–$C_6$-alkylamino, cycloalkylcarbonylamino, cycloalkylcarbonyl, cycloalkyl-$C_1$–$C_6$-alkylcarbonyl, cycloalkylcarbonyloxy, cycloalkyloxycarbonyl, cycloalkyl-$C_1$–$C_6$-alkoxycarbonyl, heteroaryl, heteroarylaminocarbonyl, heteroarylamino-$C_1$–$C_6$-alkyl, heteroaryl-$C_1$–$C_6$-alkoxy, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, heteroarylsulfinyl-$C_1$–$C_6$-alkyl, heteroarylsulfonyl-$C_1$–$C_6$-alkyl, heteroaryl-$C_1$–$C_6$-alkyl, heteroaryloxy, heteroarylthio, heteroaryl-$C_1$–$C_6$-alkylthio, heteroarylamino, heteroaryl-$C_1$–$C_6$-alkylamino, heteroarylcarbonylamino, heteroarylcarbonyl, heteroaryl-$C_1$–$C_6$-alkylcarbonyl, heteroaryloxycarbonyl, heteroarylcarbonyloxy, and heteroaryl-$C_1$–$C_6$-alkoxycarbonyl. Here, any substitutable carbon optionally is substituted with one or more halogen. In addition, the cycloalkyl, aryl, and heteroaryl typically have 3 to 6 ring atoms, and more typically 5 or 6 ring atoms.

In some preferred embodiments, a carbocyclyl or heterocyclyl optionally is substituted with one or more substituents independently selected from the group consisting of halogen, hydroxy, carboxy, keto, alkyl, alkoxy, alkoxyalkyl, alkylcarbonyl (also known as "alkanoyl"), aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl.

In some preferred embodiments, a carbocyclyl or heterocyclyl optionally is substituted with one or more substituents independently selected from the group consisting of halogen, hydroxy, carboxy, keto, $C_1$–$C_6$-alkyl, $C_1$–$C_6$-alkoxy, $C_1$–$C_6$-alkoxy-$C_1$–$C_6$-alkyl, $C_1$–$C_6$-alkylcarbonyl, aryl, aryl-$C_1$–$C_6$-alkyl, aryl-$C_1$–$C_6$-alkoxy, aryl-$C_1$–$C_6$-alkoxy-$C_1$–$C_6$-alkyl, aryl-$C_1$–$C_6$-alkoxycarbonyl, cycloalkyl, cycloalkyl-$C_1$–$C_6$-alkyl, cycloalkyl-$C_1$–$C_6$-alkoxy, cycloalkyl-$C_1$–$C_6$-alkoxy-$C_1$–$C_6$-alkyl, and cycloalkyl-$C_1$–$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with one or more halogen. The aryls or cycloalkyls typically have from 3 to 6 ring atoms, and more typically from 5 to 6 ring atoms.

In some preferred embodiments, a carbocyclyl or heterocyclyl optionally is substituted with up to three substituents independently selected from the group consisting of halogen, hydroxy, alkyl, alkoxy, amino, alkylthio, keto, and alkylamino.

In some preferred embodiments, a carbocyclyl or heterocyclyl optionally is substituted with up to three substituents independently selected from the group consisting of halogen, hydroxy, $C_1$–$C_6$-alkyl, $C_1$–$C_6$-alkoxy, amino, $C_1$–$C_6$-alkylthio, keto, and $C_1$–$C_6$-alkylamino.

In some preferred embodiments, a carbocyclyl or heterocyclyl optionally is substituted with up to three substituents independently selected from the group consisting of halogen, nitro, alkyl, haloalkyl, alkoxy, haloalkoxy, and amino.

In some preferred embodiments, a carbocyclyl or heterocyclyl optionally is substituted with up to three substituents independently selected from the group consisting of halogen, nitro, $C_1$–$C_6$-alkyl, halo-$C_1$–$C_6$-alkyl, $C_1$–$C_6$-alkoxy, halo-$C_1$–$C_6$-alkoxy, and amino.

In some preferred embodiments, a carbocyclyl or heterocyclyl optionally is substituted with up to three substituents independently selected from the group consisting of halogen, alkyl, haloalkyl, alkoxy, and haloalkoxy.

In some preferred embodiments, a carbocyclyl or heterocyclyl optionally is substituted with up to three substituents independently selected from the group consisting of halogen, $C_1$–$C_6$-alkyl, halo-$C_1$–$C_6$-alkyl, $C_1$–$C_6$-alkoxy, and halo-$C_1$–$C_6$-alkoxy.

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted", a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitutions on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "substituent" and "radical" are interchangeable.

A prefix attached to a multi-component substituent only applies to the first component. To illustrate, the term "alkylcycloalkyl" contains two components: alkyl and cycloalkyl. Thus, the $C_1$–$C_6$- prefix on $C_1$–$C_6$-alkylcycloalkyl means that the alkyl component of the alkylcycloalkyl contains from 1 to 6 carbon atoms; the $C_1$–$C_6$- prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

The term "pharmaceutically-acceptable" is used adjectivally in this specification to mean that the modified noun is appropriate for use as a pharmaceutical product or as a part of a pharmaceutical product.

With reference to the use of the words "comprise" or "comprises" or "comprising" in this patent (including the claims), Applicants note that unless the context requires otherwise, those words are used on the basis and clear understanding that they are to be interpreted inclusively, rather than exclusively, and that Applicants intend each of those words to be so interpreted in construing this patent, including the claims below.

The following are definitions for various abbreviations:

"boc" is tert-butoxycarbonyl.

"CBC" is 4-chlorobenzoyl chloride.

"DBU" is 1,8-diazabicyclo[5.4.0]undec-7-ene.

"DMAP" is dimethylaminopyridine.

"DMF" is dimethylformamide.

"DMSO" is dimethylsulfoxide.

"DSC" is differential scanning calorimetry.

"equiv." is equivalent.

"h" or "hr" is hour or hours.

"HCl" is hydrochloric acid.

"IPA" is isopropyl alcohol.

"KF" is coulometric water determination according to the Karl Fisher method.

"LDA" is lithium diisopropylamide.

"LiHMDS" is lithium hexamethyldisilazide.

"mCPBA" is 3-chloroperbenzoic acid.

"min" is minute or minutes.

"MW" is molecular weight.

"NaH" is sodium hydride.

"NaOH" is sodium hydroxide.

"NMP" is 1-methyl-2-pyrrolidinone (also called, for example, "N-methylpyrrolidinone", "1-methyl-2-pyrrolidone", "N-methylpyrrolidone", "N-methyl-2-pyrrolidinone", "methylpyrrolidinone", and "N-methyl-α-pyrrolidone").

"$N_2$" is nitrogen gas.

"ROI" is residue on ignition.

"tBuOK" is potassium tert-butoxide.

"TFA" is trifluoroacetic acid.

"THF" is tetrahydrofuran.

"Ethanol 3A" is 95% absolute ethanol and 5% methanol (HPLC grade).

EXAMPLES

The following examples are merely illustrative, and not limiting to the reminder of this disclosure in any way. These examples are directed to the preparation of a particularly preferred compound (N-(2-hydroxyacetyl)-5-(4-piperidyl)-4-(4-pyrimidinyl-3-(4-chlorophenyl)pyrazole) and a salt.

One skilled in the art, however, can prepare other compounds (and salts thereof) falling within the scope of Formula I above by applying the general principles illustrated in this example and other portions of the this specification alone or in combination with existing knowledge in the art. Existing knowledge in the art includes, for example, PCT Publication No. WO 00/31063 (incorporated herein by reference).

Example 1

Preparation of N-(2-hydroxyacetyl)-5-(4-piperidyl)-4-(4-pyrimidinyl)-3-(4-chlorophenyl)pyrazole Part A. Preparation of ethyl N-(t-butoxycarbonyl)isonipecotate (3):

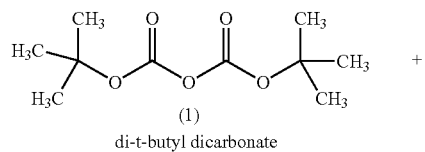
(1)
di-t-butyl dicarbonate

+

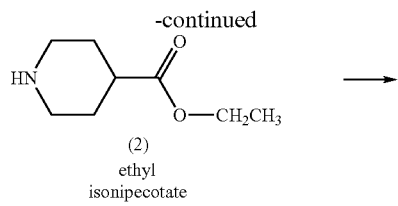
(2)
ethyl isonipecotate

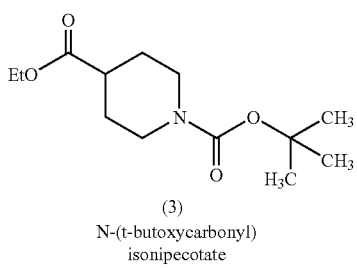
(3)
N-(t-butoxycarbonyl) isonipecotate

This reaction was conducted in a jacketed, 49 L reactor equipped with a retreat curve agitator, nitrogen purge system, and condenser system. The reactor was charged with di-t-butyl dicarbonate (1) in tetrahydrofuran ("THF") (75%, 4.674 Kg, 16.06 mol) and tetrahydrofuran (5.50 Kg, 76.3 moles). After cooling the mixture to 0° C., ethyl isonipecotate (2) (2.500 Kg, 15.90 mol) was charged to the reactor while maintaining the contents at a temperature of from 0 to 15° C. After all the ethyl isonipecotate was added, the contents were warmed to 25° C., and then stirred for 2 hours at that temperature. The mixture was then cooled to 0° C. The THF was then removed by vacuum distillation until the batch temperature reached 80° C. Afterward, the contents were cooled to 25° C. This yielded 3.99 Kg of product in the form of an amber oil. The concentration of the Boc-protected ethyl isonipecotate (3) was 96.3% (by weight).

TABLE 1

Reaction Summary for Part A

| | MW | equiv. | wt (kg) | moles | density (g/mL) | volume (L) |
|---|---|---|---|---|---|---|
| materials | | | | | | |
| compound (1) (75%) | 218.25 | 1.01 | 4.674 | 16.06 | 0.913 | 5.12 |
| tetrahydrofuran | 72.11 | 4.8 | 5.50 | 76.3 | 0.889 | 6.19 |
| compound (2) | 157.21 | 1.00 | 2.500 | 15.90 | 1.020 | 2.45 |
| product | | | | | | |
| compound (3) | 257.33 | (1.00) | (4.092) | (15.90) | | |

The numbers in parenthesis in the above table are theoretical..

Part B. Preparation of the N-(t-butoxycarbonyl)-1-(4-piperidyl)-2-(4-pyrimidyl)-1-ethanone (5).

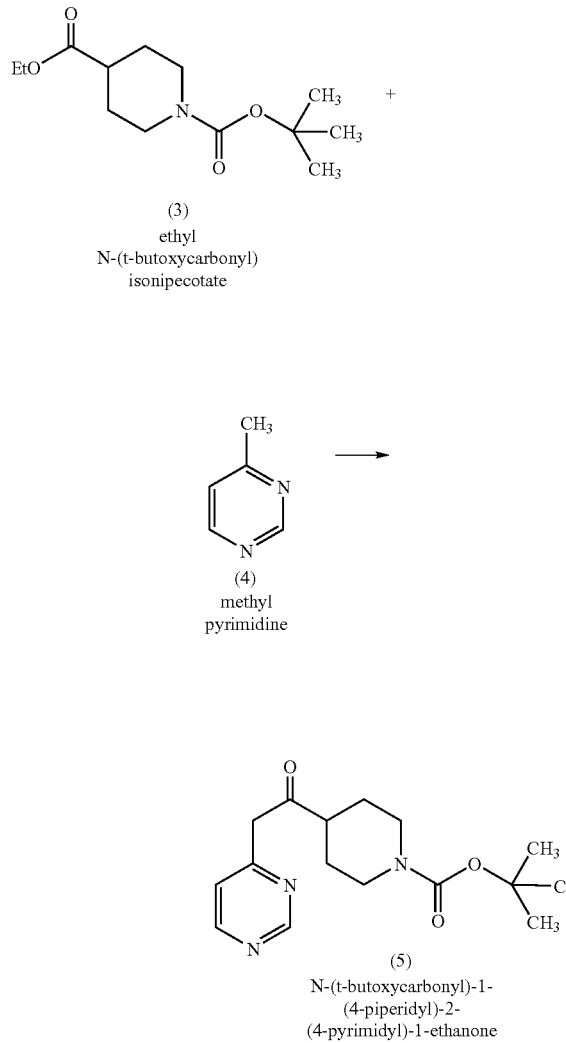

(3) ethyl N-(t-butoxycarbonyl) isonipecotate (4) methyl pyrimidine (5) N-(t-butoxycarbonyl)-1-(4-piperidyl)-2-(4-pyrimidyl)-1-ethanone This reaction was conducted in the same jacketed, 49 L reactor equipped with retreat curve agitator, nitrogen purge system, bottom valve for removal of a lower portion of the contents, and Dean-Stark trap and condenser system. The reactor was first purged with nitrogen. Afterward, 20% potassium t-butoxide in THF (21.06 Kg, 37.54 mol) was charged to the reactor under $N_2$ using a cannula system. This solution was then cooled to 0° C., and the reactor was next charged with 4-methylpyrimidine (4) (1.53 Kg, 16.27 mol) while maintaining the temperature of the reactor contents at from 0 to 5° C. Immediately afterward, the Boc-protected ethyl isonipecotate (3) prepared as shown in Part A (3.99 Kg, 15.51 mol) was charged neat over 30 minutes while continuing to maintain the reactor contents at a temperature of from 0 to 5° C. Afterward, the reactor contents were stirred for 3 hours while being maintained at 5° C. The temperature of the reactor contents was then increased to 10° C., and then maintained at that temperature for 1 hour. Subsequently, 33% aqueous acetic acid solution (6.71 Kg, 36.88 mol) was charged to the reaction mixture while maintaining the reaction mixture at below 30° C. After stirring the resulting mixture for 30 minutes, it was allowed to stand for 30 minutes. The aqueous layer was then separated. Afterward, ammonium chloride solution (2.96 Kg, 3.87 mol) was charged to the reactor. The resulting mixture was stirred for 30 minutes. After allowing the mixture to stand for 30 minutes, the aqueous layer was separated. The THF was removed from the organic remaining layer by slowly raising the batch temperature under vacuum (200 torr) until the temperature reached 60–65° C. using a distillation apparatus. The final concentrate was in the form of an amber oil. This oil and toluene (12.22 Kg, 132.6 mol) were combined in the reactor, and the resulting mixture was stirred at room temperature for 15 minutes. Afterward, water (4.01 kg, 222.5 mol) was added to the reactor, and stirring was continued for an additional 30 minutes at room temperature. The reactor contents were allowed to stand for 60 minutes. The aqueous layer was then separated. The top layer (i.e., the organic layer) was then used as is to prepare the hydrazone in Part C.

TABLE 2

Reaction Summary for Part B

| materials | MW | equiv. | wt (kg) | moles | density (g/mL) | volume (L) |
|---|---|---|---|---|---|---|
| potassium t-butoxide in THF (20%) | 112.2 | 2.42 | 21.06 | 37.54 | 0.902 | 23.3 |
| compound (3) | 257.3 | 1.00 | 3.99 | 15.51 | 1.034 | 3.86 |
| compound (4) | 94.11 | 1.05 | 1.53 | 16.27 | 1.031 | 1.48 |
| 33% acetic acid solution | 60.05 | 2.40 | 6.71 | 36.88 | 1.049 | 6.4 |
| 7% ammonium chloride solution | 53.49 | 0.25 | 2.96 | 3.87 | | |
| toluene | 92.14 | 10.20 | 12.22 | 132.6 | 0.865 | 14.1 |
| water | 18.02 | 14.35 | 4.01 | 222.5 | 1.000 | 4.01 |

Part C. Preparation of the N-(t-butoxycarbonyl)-1-(4-piperidyl)-2-(4-pyrimidyl)-1-ethanone p-toluenesulfonyl hydrazone (7).

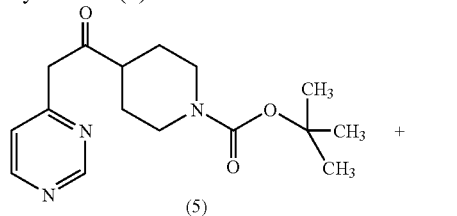

(5)
N-(t-butoxycarbonyl)-1-
(4-piperidyl)-2-(4-pyrimidyl)-1-ethanone

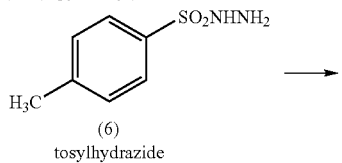

(6)
tosylhydrazide

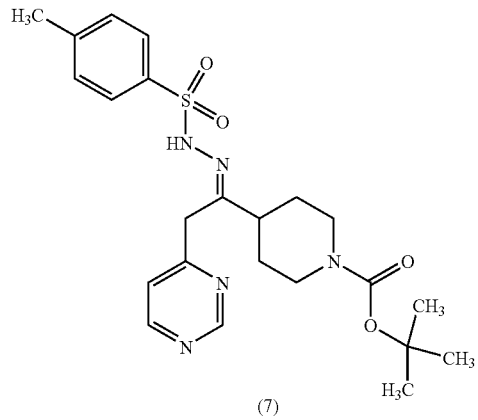

(7)
N-(t-butoxycarbonyl)-1-
(4-piperidyl)-2-(4-pyrimidyl)-1-
ethanone p-toluenesulfonyl hydrazone Toluenesulfonylhydrazide (6) (2.6 Kg, 13.96 mol) was combined with the reaction mixture from Part B in the same reactor. The resulting mixture was heated to 70° C. while being stirred and maintained at this temperature for 2 hours. The reaction mixture was then refluxed at 70° C. under reduced pressure (200 torr) using the Dean-Stark moisture trap for 1 hour. Afterward, the mixture was cooled to 0° C. over 1.5 hours, and then maintained at 0° C. for at least 12 hours. The resulting solids were collected using a filter (using a 4 micron filter cloth). The wet cake was then washed with toluene (3.79 Kg, 41.13 mol, 0 to 5° C.), followed by ethyl acetate (3.95 Kg, 44.83 mol, 0 to 5° C.). After the cake was dried on the filter for 2 hours, and then transferred to a vacuum oven at 40° C. for at least 4 hour. This yielded 5.15 Kg (70%) of a light yellow solid. The concentration of hydrazone (7) was 99.2% (by weight).

TABLE 3

Reaction Summary for Part C

| | MW | equiv. | wt (kg) | moles | density (g/mL) | volume (L) |
|---|---|---|---|---|---|---|
| materials | | | | | | |
| compound (6) | 186.2 | 0.90 | 2.60 | 13.96 | | |

TABLE 3-continued

Reaction Summary for Part C

| | MW | equiv. | wt (kg) | moles | density (g/mL) | volume (L) |
|---|---|---|---|---|---|---|
| toluene | 92.14 | 2.65 | 3.79 | 41.13 | 0.865 | 4.38 |
| ethyl acetate | 88.10 | 2.89 | 3.95 | 44.83 | 0.902 | 4.38 |
| product | | | | | | |
| compound (7) | 473.60 | (1.00) | (7.34) | (15.51) | | |

The numbers in parenthesis in the above table are theoretical.

Part D. Preparation of tert-butyl 4-{5-(4-chlorophenyl)-1-[(4-methylphenyl)sulfonyl]-4-pyrimidin-4-yl-1H-pyrazol-3-yl}piperidine-1-carboxylate (9).

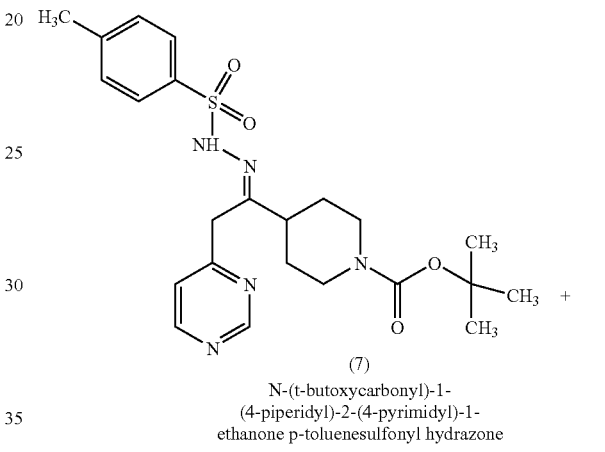

(7)
N-(t-butoxycarbonyl)-1-
(4-piperidyl)-2-(4-pyrimidyl)-1-
ethanone p-toluenesulfonyl hydrazone

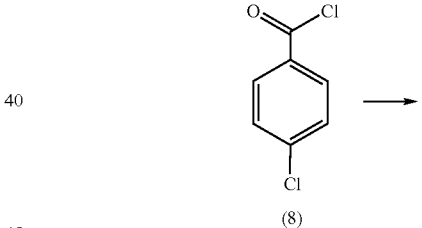

(8)
4-chlorobenzoyl chloride

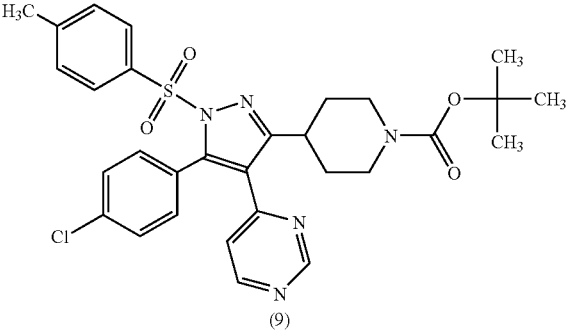

(9)
tert-butyl 4-{5-(4-chlorophenyl)-1-
[(4-methylphenyl)sulfonyl]-4-
pyrimidin-4-yl-1H-pyrazol-3-yl}
piperidine-1-carboxylate This reaction was conducted in the same jacketed, 49 L reactor equipped with a retreat curve agitator, metering pump, nitrogen purge system, and condenser system. The reactor was first purged with nitrogen at room temperature. The clean, dry reactor was then charged with the hydrazone (7) prepared as shown in Part C (2.77 Kg, 5.85 mol), dimethylaminopyridine ("DMAP") (0.0715 Kg, 0.585 mol), tetrahydrofuran (12.47 Kg, 173.04 mol), and triethylamine (0.829 Kg, 8.19 mol). Next, 4-chlorobenzoyl chloride (8) ("CBC") (1.28 Kg, 7.31 moles) was added to the reactor over 20 minutes using a pump at such a rate as to keep the internal temperature less than 40° C. The contents turned deep yellow and formed a precipitate. After the addition of the 4-chlorobenzoyl chloride, the reaction mixture was heated to 65° C. over 30 minutes, and then maintained at that temperature for 5 hours. Subsequently, the temperature of the mixture was decreased to room temperature, and water (2.77 kg, 153.7 mol) was added. The resulting mixture was stirred for 0.5 hours. Subsequently, the organic and aqueous phases were allowed to separate, and the aqueous phase was removed from the bottom of the reactor. To the remaining organic layer was added 22% aqueous ammonium chloride solution (4.62 L). The resulting mixture was stirred for 0.5 hours. The stirring was stopped and the organic and aqueous phases were allowed to separate. The aqueous phase was removed from the bottom of the reactor. An IPA-water mixture (1:1 (vol:vol); 22.16 L) was then added to the remaining organics over 2 hours. Subsequently, the resulting mixture was stirred for 5 hours. The solids were filtered (4 micron filter cloth), washed with IPA-water (1:1 (vol:vol); 7.39 L), and dried on the filter for 2 hours. The wet cake was transferred to a vacuum oven at 80° C. (house vacuum) for 6 hours. This yielded 2.85 Kg (84.6%) of solids. The concentration of the protected pyrazole intermediate (9) was 99.0% (by weight).

TABLE 4

Reaction Summary for Part D

| material | MW | equiv. | wt (Kg) | moles | density (g/mL) | volume (L) |
|---|---|---|---|---|---|---|
| compound (7) | 473.59 | 1.0 | 2.77 | 5.85 | | |
| tetrahydrofuran (THF) | 72.11 | 29.58 | 12.47 | 173.04 | 0.889 | 14.0 |
| compound (8) | 175.01 | 1.25 | 1.28 | 7.31 | 1.377 | 0.93 |
| triethylamine (TEA) | 101.19 | 1.43 | 0.829 | 8.19 | 0.726 | 1.14 |
| 4-dimethylamino pyridine (DMAP) | 122.17 | 0.102 | 0.0715 | 0.585 | | |
| water | 18 | 26.3 | 2.77 | 153.7 | 1.000 | 2.77 |
| 22% NH₄Cl | 53.49 | 3.5 | | 18.47 | | 4.62 |
| IPA-water anti-solvent | | | | | | 22.16 |
| IPA-water cake wash | | | | | | 7.39 |
| product | | | | | | |
| compound (9) | 594.13 | (1.0) | (3.48) | (5.85) | | |

The numbers in parenthesis in the above table are theoretical.

Part E. Preparation of 5-(4-piperidyl)-4-(4-pyrimidinyl)-3-(4-chlorophenyl)pyrazole (10).

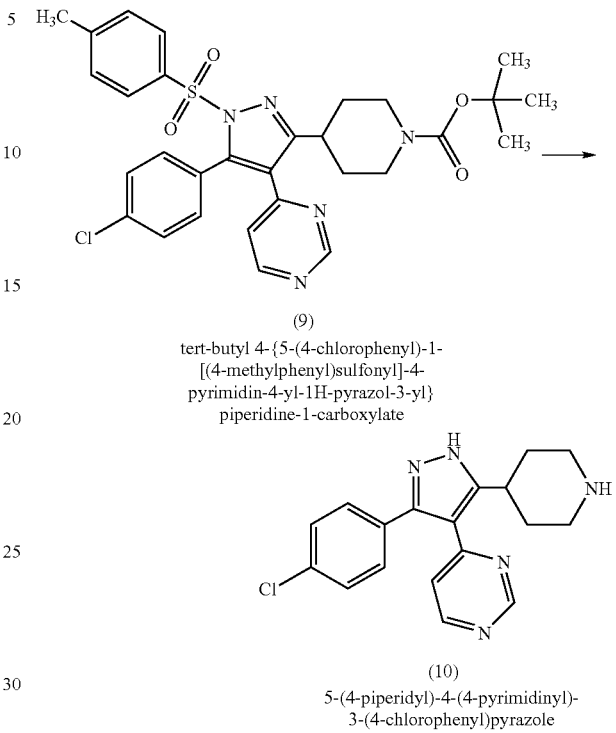

(9)
tert-butyl 4-{5-(4-chlorophenyl)-1-[(4-methylphenyl)sulfonyl]-4-pyrimidin-4-yl-1H-pyrazol-3-yl} piperidine-1-carboxylate

(10)
5-(4-piperidyl)-4-(4-pyrimidinyl)-3-(4-chlorophenyl)pyrazole

The following discussion describes two variations of this reaction:

A. First Variation

In the first variation, the above reaction was conducted in the same jacketed, 49 L reactor equipped with a retreat curve agitator, nitrogen purge, and metering pump. The reactor was charged with the protected pyrazole intermediate (9) prepared as shown in Part D (5.0 Kg, 8.42 mol) and toluene (10.0 kg, 108.5 mol). After initiating stirring, 37% HCl (6.64 Kg, 67.4 mol) was added over 15 minutes via a pump. Immediate gas evolution and a temperature increase from 22.2° C. to 28.4° C. were observed. Two phases appeared within 10 minutes. The temperature was maintained at 20° C. for 1.0 hour. Afterward, water (20 Kg, 1110 mol) was added, and the resulting mixture was stirred for 20 minutes. The organic and aqueous phases were then separated, and the aqueous phase was introduced back into the reactor. The reactor was then additionally charged with 6 N NaOH (10.0 Kg, 60.2 mol) via a pump over 30 minutes. This increased the pH to 12, and caused a white/off-white slurry to form. The mixture was heated to 75° C. over 30 minutes, and then held at that temperature for an additional 2 hours. Subsequently, the mixture was cooled to 25° C. The solids were filtered with a 4 micron filter cloth, washed with deionized water (3×15 Kg), and air-dried for 45 minutes, i.e., until a constant weight (LOD<50%) was observed. The resulting cake was introduced into the reactor, along with acetonitrile (15 Kg). This mixture was heated to reflux, and then maintained at reflux for 1 hour. Subsequently, the mixture was cooled to 5° C., and then maintained at that temperature for 30 minutes. The solids were filtered with a 4 micron filter cloth, washed with acetonitrile (15 Kg), and dried in a vacuum oven at 85° C. for 12 hours (LOD<1%). This yielded 2.64 Kg (92%) of slightly off-white solids. The concentration of 5-(4-piperidyl)-4-(4-pyrimidinyl)-3-(4-chlorophenyl)pyrazole was greater than 97% (by weight). No single impurity was present at >1% (by weight). The residue on ignition ("ROI") was <1%, and the coulometric water determination according to the Karl Fisher method ("KF") also was <1%.

water (2×15 L). The final pH of the rinse was 7.5. The cake was pulled dry for 60 minutes. This provided wet cake with a 19.4% LOD. The wet cake was charged back to the reactor, along with acetonitrile (15.0 kg, 19.1 L). The resulting mixture was heated to reflux (82° C.), and held at that temperature for 2 hours and 29 minutes. The slurry was then cooled to 5° C., and then held at that temperature for 30 minutes. The resulting product was filtered and then filter pulled dry until no mother languor was coming off the filter. The cake was rinsed with acetonitrile (18 L) and then pulled dry for 2 hours. The wet cake (LOD 12.2%) was transferred to a vacuum dryer at 85° C. for 16 hours and 20 minutes (although it is believed that a time period of from 6 to 12 hours would have been sufficient). This provided 2.64 Kg at 92.2% isolated yield.

TABLE 5

Reaction Summary for Part E (First Variation)

| material | MW | equiv. vs. compound (9) | wt (Kg) | wt ratio to compound (9) | moles | density (g/mL) | volume (L) |
| --- | --- | --- | --- | --- | --- | --- | --- |
| compound (9) | 594.13 | 1.0 | 5.0 | 1 | 8.42 | — | — |
| 37% HCl | 36.46 | 8.0 | 6.64 @ 37% | 1.3 | 67.4 | 1.200 | 5.53 |
| toluene | 92.14 | 12.9 | 10.0 | 2 | 108.5 | 0.865 | 11.6 |
| 6 N NaOH | 40.0 | 7.2 | 10.0 @ 6N | 2 | 60.2 | 1.22 | 8.2 |
| water addition | 18.02 | 132 | 20.0 | 4 | 1,110 | 1.000 | 20.0 |
| water wash #1 | 18.02 | 99 | 15.0 | 3 | 832 | 1.000 | 15.0 |
| water wash #2 | 18.02 | 99 | 15.0 | 3 | 832 | 1.000 | 15.0 |
| water wash #3 | 18.02 | 99 | 15.0 | 3 | 832 | 1.000 | 15.0 |
| acetonitrile trituration | 41.05 | 43 | 15.0 | 3 | 365 | 0.786 | 19.0 |
| acetonitrile wash | 41.05 | 43 | 15.0 | 3 | 365 | 0.786 | 19.0 |
| product compound (10) | 339.83 | (1.0) | (2.86) | | (8.42) | | |

The numbers in parenthesis in the above table are theoretical.

B. Second Variation

In the second variation, the above reaction was likewise conducted in the same jacketed, 49 L reactor equipped with a retreat curve agitator, nitrogen purge, and metering pump. The reactor was charged with the protected pyrazole intermediate (9) prepared as shown in Part D (5.0 Kg, 8.42 mol) and toluene (10.0 kg, 108.5 mol). After initiating stirring, 37% HCl (6.64 Kg, 67.4 mol) over 16 minutes. A temperature increase from 20 to 28° C. was observed during the addition. The temperature of the mixture was then increased to 70° C. over a 30 minutes period (1.5° C./minute), and held at 70° C. for 2 hours. The mixture was then cooled to 23° C. over 1 hour. After adding water (20 L), the mixture was stirred for 30 minutes. Agitation was then halted, and the phases were allowed to separate for 57 min. The bottom phase (i.e., the aqueous phase, which contained product) was removed from the reactor. After removing the top phase (i.e., the organic phase), the reactor was rinsed with toluene, followed by water, to remove residuals. The aqueous phase containing the product was then transferred back to the reactor. The reactor was then additionally charged with 6 N NaOH (10.0 kg, 54.74 mol, 6.5 equiv.) over 27 minutes. The observed final pH was 12.25. The reaction mixture was then heated to 75° C. over 30 minutes and held at that temperature for 2 hours. The slurry was then quickly cooled to 25° C. The product (in the form of solids) was collected by filtration using a pressure filter, and washed on the filter with Part F. Preparation of the NMP solvate of N-(2-hydroxyacetyl)-5-(4-piperidyl)-4-(4-pyrimidinyl)-3-(4-chlorophenyl)pyrazole (12).

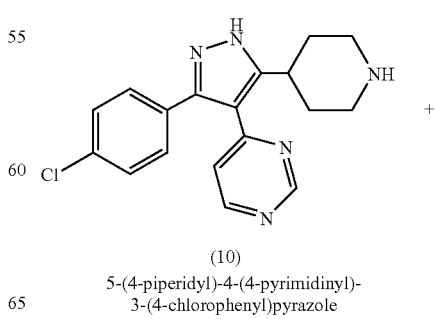

(10)
5-(4-piperidyl)-4-(4-pyrimidinyl)-
3-(4-chlorophenyl)pyrazole

-continued

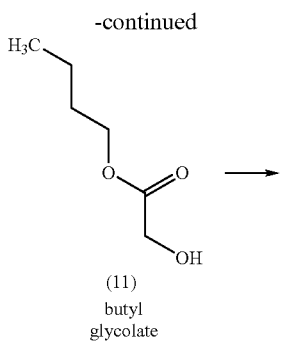

(11)
butyl
glycolate

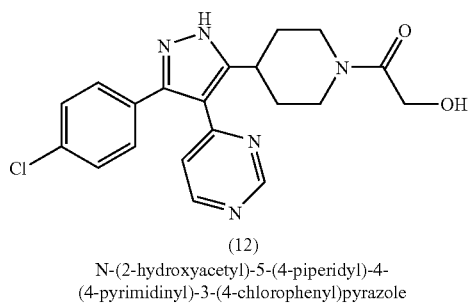

(12)
N-(2-hydroxyacetyl)-5-(4-piperidyl)-4-
(4-pyrimidinyl)-3-(4-chlorophenyl)pyrazole The following discussion describes three variations of this reaction:

A. First Variation

This reaction was conducted in a jacketed, 0.1 L reactor equipped with an agitator, nitrogen purge, thermocouple, and condenser. The reactor was charged with 5-(4-piperidyl)-4-(4-pyrimidinyl)-3-(4-chlorophenyl)pyrazole (10) prepared as shown in Part E (10 g, 0.029 mol); 1-methyl-2-pyrrolidinone (20 g, 0.20 mol); butyl glycolate (11) (9.7 g, 0.073 mol), and 1,8-diazabicyclo[5.4.0]undec-7-ene ("DBU") (0.45 g, 0.0029 mol). After stirring was initiated, the mixture was heated to about 110° C., and then maintained at that temperature for 3 hours. At that point, it was determined by HPLC that conversion from starting material to product had ceased (i.e., <3 area % starting material remained). The reactor contents were then cooled to 25° C. over 1 hour. Ethanol 3A (1.74 g, 0.038 mol) was then charged to the reactor. The resulting mixture was maintained at 25° C. for an additional hour, and then further cooled to 0° C. over 30 minutes. This temperature was maintained for an additional 2 hours. The solids were collected via filtration using a 4 micron filter cloth, washed with NMP (2×18 g), and air-dried on the filter giving rise to the NMP solvate of the desired product, which was analyzed via differential scanning calorimetry ("DSC"). The solids were introduced to the reactor along with 100 mL of ethanol. The resulting mixture was then heated to reflux, and maintain at reflux for 4 hours. Afterward, the mixture was cooled to 15° C. over 3 hours. The product was then isolated by filtration using a 4 micron filter cloth, washed (using a displacement wash) with ethanol 3A (2×33 g), and air-dried on the filter. This yielded 9.0 g of white/off-white/yellow crystals (78% yield) (HPLC weight % >98%).

TABLE 6

Reaction Summary for Part F

| | MW | equiv. | wt. (g) | moles | density (g/mL) | volume (mL) |
|---|---|---|---|---|---|---|
| materials | | | | | | |
| compound (10) | 339.83 | 1.00 | 10.0 | 0.029 | | |
| 1-methyl-2-pyrrolidinone | 99.13 | 6.96 | 20.0 | 0.20 | 1.028 | 15.6 |
| 1,8-Diazabicyclo-(5.4.0)undec-7-ene | 152.24 | 0.10 | 0.45 | 0.0029 | 1.018 | 0.44 |
| compound (11) | 132.16 | 2.5 | 9.7 | 0.073 | 1.019 | 9.5 |
| Ethanol 3A | 46.01 | 1.31 | 1.7 | 0.038 | 0.790 | 2.2 |
| 1-methly-2-pyrrolidinone (wash) | 99.13 | 6.26 | 18.0 | 0.18 | 1.028 | 17.5 |
| 1-methly-2-pyrrolidinone (wash) | 99.13 | 6.26 | 18.0 | 0.18 | 1.028 | 17.5 |
| Ethanol 3A | 46.01 | 59.2 | 79 | 1.72 | 0.790 | 100 |
| Ethanol 3A (wash) | 46.01 | 24.7 | 33 | 0.72 | 0.790 | 26.1 |
| Ethanol 3A (wash) product | 46.01 | 24.7 | 33 | 0.72 | 0.790 | 26.1 |
| compound (12) | 397.86 | (1.00) | (11.5) | (0.029) | | |

The numbers in parenthesis in the above table are theoretical.

B. Second Variation

In the second variation, the reaction was conducted in a jacketed, 49 L reactor equipped with a retreat curve agitator, nitrogen purge, and metering pump. This reactor was charged with 5-(4-piperidyl)-4-(4-pyrimidinyl)-3-(4-chlorophenyl)pyrazole (10) prepared as shown in Part E (1.9 Kg, 5.6 mol) and 1-Methyl-2-pyrrolidinone (3.8 Kg, 38.3 mol). After initiating agitation at 75 rpm and allowing the mixture to stir for 6 minutes, the reactor was further charged with butyl glycolate (11) (1.85 Kg, 14 mol, added via an addition funnel) and DBU (85.12g, 0.54 mol) while continuing to stir the contents. The mixture was then heated to 110° C. over 23 minutes, and then held at that temperature for 3 hours. A sample taken 15 minutes after the 110° C. temperature had been reached indicated a 87.2% conversion of the 5-(4-piperidyl)-4-(4-pyrimidinyl)-3-(4-chlorophenyl)pyrazole (10), a sample taken 60 minutes after the 110° C. temperature had been reached indicated a 98.7% conversion of the 5-(4-piperidyl)-4-(4-pyrimidinyl)-3-(4-chlorophenyl)pyrazole (10), and a sample taken 120 minutes after the 110° C. temperature had been reached indicated a 99.7% conversion of the 5-(4-piperidyl)-4-(4-pyrimidinyl)-3-(4-chlorophenyl)pyrazole (10). After the heating, the reaction mixture was cooled to approximately 25° C. over 1 hour and 5 minutes (the final baffle temperature was 28.5° C., while the contents at the bottom were at 22.2° C.). A sample was taken, and then the reactor was charged with Ethanol 3A (12.35 Kg, 268 mol) over 55 minutes. After the ethanol was charged, a sample was taken. The mixture was then stirred for 65 minutes. A sample taken after the first 30 minutes of the stirring indicated that 2.8% of the N-(2-hydroxyacetyl)-5-(4-piperidyl)-4-(4-pyrimidinyl)-3-(4-chlorophenyl)pyrazole product (12) remained in solution, and a sample taken after 60 minutes of the stirring indicated that 3.4% of the N-(2-hydroxyacetyl)-5-(4-piperidyl)-4-(4-pyrimidinyl)-3-(4-chlorophenyl)pyrazole product (12) was in solution. The mixture was next heated to reflux over 1 hour and 2 minutes, and then maintained at reflux for 4 hours. Supernatant and solid samples were collected every 30 minutes. After the 4 hours of refluxing, the mixture was cooled to 5° C. at a rate of 0.25° C./minute, and then maintained at that temperature overnight. The resulting product was filtered, providing 17.46 Kg of filtrate. The cake was washed with ethanol 3A (2×3.14 Kg (68.3 mol). The washed cake was then pull dried to LOD=0.67%. The amount of resulting wet cake was 2.00 Kg (89.7% non-assay adjusted molar yield). The NMP concentration in the wet cake was determined using gas chromatography ("GC") to be 518 ppm. The NMP concentration in the wet cake using the GC method with solid phase micro-extraction ("SPME") was 580 ppm.

A portion of the wet cake (1.0 Kg, 2.51 mole) was then combined with ethanol 3A (9.0 Kg, 11.38 L, 196 mol) by vacuum in the same reactor. Agitation was set to 80 RPM. The mixture was heated to reflux (i.e., 78–80° C.) over 33 minutes, and then held at reflux for 3 hours and 10 minutes. Samples were taken after the first 1 hour and 10 minutes, after the first 2 hours and 10 minutes, and at the end of the 3 hours and 10 minutes. The mixture was then cooled to 5° C. over 3 hours and 10 minutes, and held at 5° C. overnight (i.e., approximately 16 hours and 50 minutes). Samples were taken during the cool-down period. The solids were filtered using a pressure filter, and a sample was taken from the mother liquor. The amount of mother liquor collected was 8.68 Kg. The cake was washed with ethanol 3A (2×3.14 Kg (68.3 mol), samples taken after each wash). The cake was then pull dried for 1–2 hours to LOD=0.31%. This produced 0.892 Kg of wet cake (89.6% non-assay adjusted molar yield). Total impurities in the cake were determined to be 0.46% (by weight), with NMP being present at a concentration of 0.01% (by weight) and 5-(4-piperidyl)-4-(4-pyrimidinyl)-3-(4-chlorophenyl)pyrazole (10) being at a concentration of 0.01% (by weight).

C. Third Variation

In the third variation, the reaction was conducted in a jacketed, 0.1 L reactor equipped with an agitator, nitrogen purge, thermocouple, and condenser. This reactor was charged with 5-(4-piperidyl)-4-(4-pyrimidinyl)-3-(4-chlorophenyl)pyrazole (10) prepared as shown in Part E (1.9 Kg, 5.6 mol, LOC=0.40%) and 1-Methyl-2-pyrrolidinone (3.8 Kg, 38.3 mol). After initiating stirring at 75 RPM, the reactor was further charged with butyl glycolate (11) (1.85 Kg, 14 mol) via an addition funnel and DBU (85.08 g, 0.56 mol) while continuing to stir the contents. The mixture was then heated to 110° C. over 50 minutes, and then held at that temperature for 3 hours and 25 minutes. A sample taken 15 minutes after the 110° C. temperature had been reached indicated a 89.8% conversion of the 5-(4-piperidyl)-4-(4-pyrimidinyl)-3-(4-chlorophenyl)pyrazole (10), a sample taken 60 minutes after the 110° C. temperature had been reached indicated a 99.1% conversion of the 5-(4-piperidyl)-4-(4-pyrimidinyl)-3-(4-chlorophenyl)pyrazole (10), and a sample taken 180 minutes after the 110° C. temperature had been reached indicated a 99.6% conversion of the 5-(4-piperidyl)-4-(4-pyrimidinyl)-3-(4-chlorophenyl)pyrazole (10). The mixture was cooled to 40° C. over 2 hours and 20 minutes, and a sample was taken. The reactor was then charged with ethanol 3A (0.76 Kg, 16.5 mol) over 23 minutes. After the ethanol was added, a sample of the solid was taken. The mixture was heated to reflux over 1 hour and 20 minutes, and then held at reflux for 4 hours. Supernatant and solid samples were collected every 60 minutes. After the refluxing, the mixture was cooled to 5° C. at a rate of 0.25° C./min, and then held at that temperature overnight. Samples of the solid and supernatant were collected. The mixture was then filtered, producing 3.54 Kg of filtrate (a sample of the filtrate was collected). The cake was washed with methyl t-butyl ether ("MTBE", 2×3.14 Kg (35.6 mol), samples of the MTBE were collected after each wash). The washed cake was then pull dried for 1 hour and 15 minutes (LOD=0.47%). This produced 2.56 Kg of wet cake. The non-assay adjusted yield was 92.1%. The NMP concentration in the wet cake was determined using gas chromatography to be 518 ppm. The NMP concentration in the wet cake using the GC method with SPME was 580 ppm. The wet cake was then treated using two alternative procedures:

i. First Alternative Wet Cake Treatment

A portion of the wet cake prepared above (1.2 Kg, LOD-0.47%) was charged to the same reactor, along with ethanol 3A (9.0 Kg, 11.38 L) via vacuum. This produced a thick slurry. The agitator speed was set to 95 RPM. The slurry was heated to reflux (i.e., 78–80° C.) over 16 minutes, and then held at reflux for 5 hours. Samples were collected when the mixture first reached reflux, 102 minutes later, 162 minutes later, 186 minutes later, and 251 minutes later. The mixture was then cooled to 5° C. over 2 hours and 46 minutes, and then held at that temperature overnight (i.e., 11 hours and 59 minutes). The product was filtered with a pressure filter producing 8.50 Kg of mother liquor (a sample of the mother liquor was collected). The cake was washed with ethanol (2×1.60 Kg, samples taken after each wash). The cake was then pull dried for a few hours. This produced 1.07 Kg of wet cake (LOD=18.0%). After collecting a sample, the wet cake was then dried in a vacuum dryer at 50° C. over a approximately a weekend. This produced 0.894 Kg wet cake (LOD=0.51%) with a 93.0% non-assay adjusted molar yield. Total impurities in the cake were determined to be 0.45% (by weight), with NMP being present at a concentration of 0.01% (by weight) and 5-(4-piperidyl)-4-(4-pyrimidinyl)-3-(4-chlorophenyl)pyrazole (10) being at a concentration of 0.01% (by weight).

ii. Second Alternative Wet Cake Treatment

A second portion of the wet cake (4 g) was charged to a nitrogen-purged, 100 ml, jacketed vessel equipped with a chiller and an overhead stirrer. Ethanol 3A (34.2 g ethanol and 1.8 g methanol) and DBU (0.15 g) were pre-mixed, and then charged to the reactor while stirring the contents at 250 RPM. Stirring was continued for 1 hour at room temperature. The contents were then heated to reflux for 1 hour, and then cooled to 0° C. for 3 hours. The next day, the solids were filtered and washed with ethanol 3A. The resulting cake was pull-dried overnight with house vacuum. The solids were then placed in a vacuum oven at approximately 50° C. for another several hours.

Example 2

Preparation of an HCl salt of N-(2-hydroxyacetyl)-5-(4-piperidyl)-4-(4-pyrimidinyl)-3-(4-chlorophenyl)pyrazole

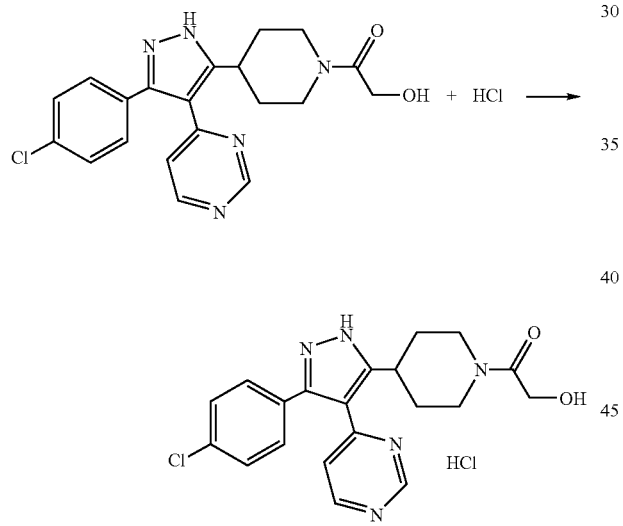

A 10-mL, one-necked, round-bottomed flask equipped with a tubing adapter connected to a nitrogen bubbler and a magnetic stirring bar was charged with N-(2-hydroxyacetyl)-5-(4-piperidyl)-4-(4-pyrimidinyl)-3-(4-chlorophenyl)pyrazole (0.398 g, 1.0 mmol) and 3.0 mL of ethanol. Hydrogen chloride was then added as a 1.0 M solution in ethanol (1.25 mL, 1.25 mmol). The resulting suspension was stirred at room temperature for 1 hour, and then heated to reflux. The hot solution was filtered to remove a small amount of insoluble material. The filtrate was then stirred at room temperature for 2 hours. The suspension that formed was then cooled in an ice-water bath and stirred for an additional 2 hours. The suspension of crystals was filtered, and the collected solid was dried for 2 hours at 40° C. under oil-pump vacuum to afford 0.381 g of the HCl salt as a yellow crystalline solid. The salt had the following characteristics: $^1$H NMR (DMSO-$d_6$; 400 MHz) δ: 1.7 (m, 2H), 1.9 (d, 2H), 2.7 (t, 1H), 3.0 (t, 1H), 3.4 (m, 1H), 3.8 (d, 1H), 4.1 (q, 2H), 4.5 (d, 1H), 7.2 (d, 1H), 7.4–7.5 (m, 4H), 8.7 (d, 1H), 9.3 (s, 1H). Microanalysis: Calculated for ($C_{20}H_{20}ClN_5O_2$).HCl.0.2(EtOH): C, 55.24; H, 5.04; N, 15.79. Found: C, 54.97; H, 5.04; N, 15.72.

Example 3

Preparation of N-(2-hydroxyacetyl)-5-(4-piperidyl)-4-(4-pyrimidinyl)-3-(4-chlorophenyl)pyrazole Using an Acetyl Protecting Group on the Isonipecotate Nitrogen Part A. Preparation of N-acetyl ethyl isonipecotate (3):

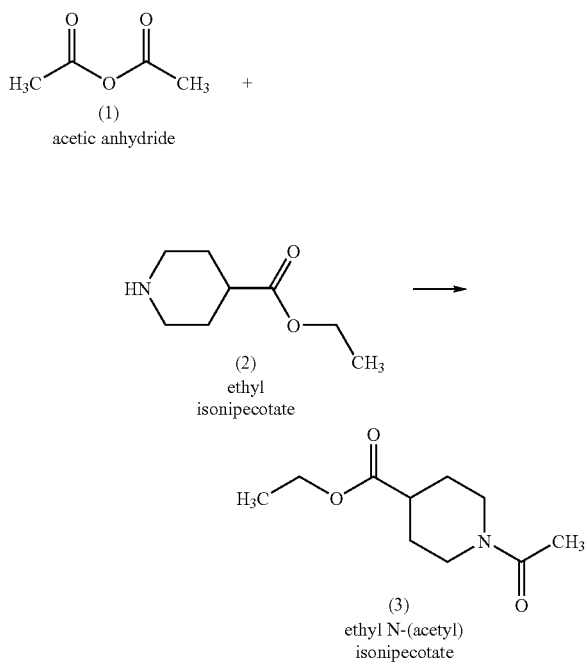

Ethyl isonipecotate (91 ml) was placed into a 100 ml, three-necked flask fitted with a pressure equalizing funnel and an overhead stirrer. Tetrahydrofuran (200 ml) was then added, and the resulting mixture was cooled with an ice water bath. The pressure equalizing addition funnel was charged with acetic anhydride (59 ml), and the acetic anhydride was then added over 2 hr with stirring. After addition the reaction was stirred for a further hour. The mixture was diluted with ethyl acetate and washed with saturated NaHCO$_3$ (7 times with 100 ml). The organic layer was dried over MgSO$_4$ and filtered. The ethyl acetate was then removed in vacuo to yield 98.97 g (86% yield) of product as a pale yellow liquid. The product had the following characteristics: $^1$H NMR (CDCl$_3$, 300 MHz) δ 4.40–4.29 (1H, m), 4.12–4.03 (2H, m,), 3.79–3.69 (1H, m), 3.20–3.02 (1H, m), 2.81–2.68 (1H, m), 2.51–2.40 (1H, m), 2.04–2.02 (3H, multiple singlets), 1.89–1.80 (2H, m), 1.70–1.49 (2H, m), 1.24–1.14 (3H, m). $^{13}$C NMR (CDCl$_3$, 75 MHz) δ174.34, 169.01, 60.74, 45.82, 41.09, 28.58, 27.99, 21.60, 21.59, 14.37.

Part B. Preparation of N-(acetyl)-1-(4-piperidyl)-2-(4-pyrimidyl)-1-ethanone (5).

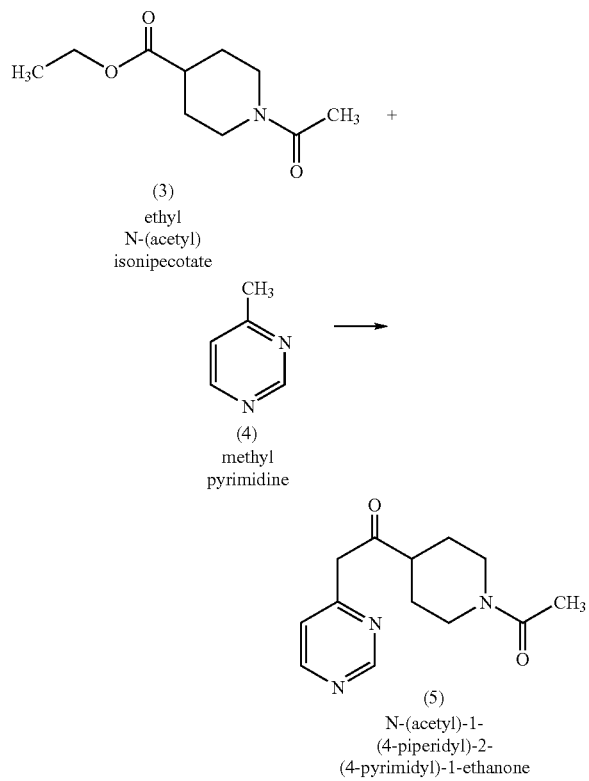

This reaction was conducted in a 1000 ml, 4-neck jacketed Ace reactor with a mechanical stirrer, nitrogen inlet, addition funnel or condenser or distilling head with receiver, thermocouple, and Teflon paddle agitator. The reactor was first purged with nitrogen. Afterward, a solution of 20% potassium t-butoxide in tetrahydrofuran (286.2 g, 258 ml, 0.51 moles of potassium t-butoxide, 2.4 equivalents relative to moles of methyl pyrimidine (4), from Callery (Evans City, Pa.)). After cooling the solution to 0° C., 4-methypyrimidine (4) (20.0 g, 20.6 ml, 0.2 13 moles, from SKW (Marietta, Ga.)) was charged neat over 30 mm while maintaining the temperature at less than 5° C. Afterward, the mixture was stirred for 60 mm while maintaining the temperature at 0° C. N-acetyl ethyl isonipecotate (3) (42.3 g, 42 ml, 0.213 moles, 1.0 equivalent relative to moles of methyl pyrimidine (4)) was then charged neat over 30 mm while maintaining the temperature at less than 5° C. The resulting mixture stirred for 30 mm at 0° C. The temperature was then increased to 35° C. over 30 mm, and then maintained at 35° C. for at least 1 hr (until at least 98% of the ethyl N-(acetyl)isonipecotate (3) was consumed, as measured by chromatography). Afterward, the mixture was cooled to 10° C., and 3M HCl (166 ml, 0.499 moles, 2.35 equivalent relative to moles of methyl pyrimidine (4)) was charged over approximately 45 mm to decrease the pH to 6–7 while maintaining the temperature at less than 25° C. Subsequently, the temperature was decreased to 15° C., and the pressure was decreased to 150 torr. The temperature was then slowly increased, and the solvents were removed by distillation until the temperature reached 45° C. The pressure was then increased to ambient with nitrogen. Subsequently, water (94 ml, 4.7 ml per gram of methyl pyrimidine (4)) was charged while cooling the mixture to 40° C.

Part C. Preparation of the N-(acetyl)-1-(4-piperidyl)-2-(4-pyrimidyl)-1-ethanone p-toluenesulfonyl hydrazone (7).

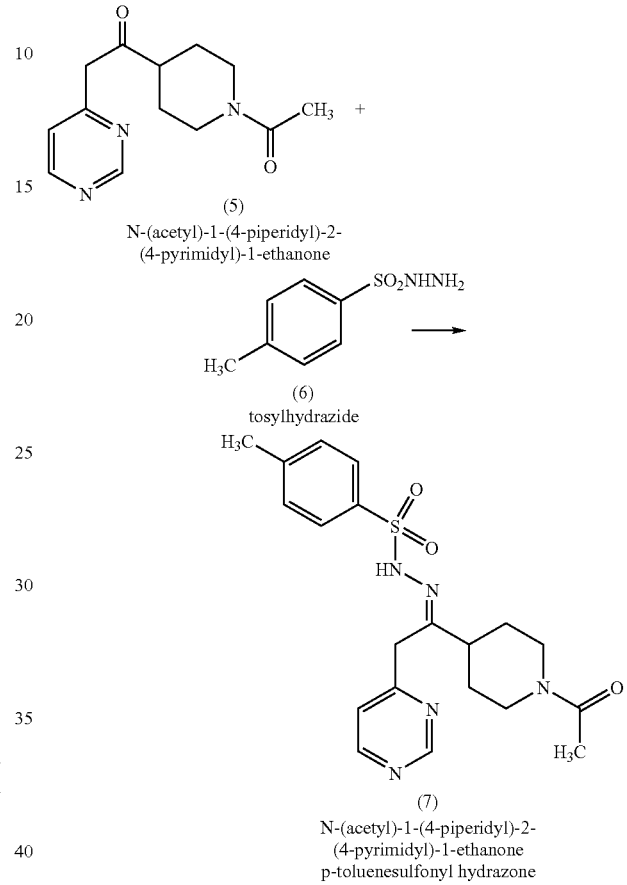

This reaction also was conducted in the reactor of Part B. Toluenesulfonylhydrazide (6) (40.8 g, 0.2 13 moles, 1.0 equivalent relative to moles of methyl pyrimidine (4) used in Part B, 97% purity, from Aldrich (Milwaukee, Wis.)) was charged to the reaction mixture product from Part B. Afterward, methanol (134 ml, 6.7 ml per gram of 4-methyl pyrimidine (4) used in Part B) was charged. The resulting mixture was heated to a temperature of 50° C. After adjusting the pH to 3 using 3M HCl (3.5 ml, 0.011 moles, 0.05 equivalents relative to moles of methyl pyrimidine (4) used in Part B), the mixture was stirred at 50° C. for at least 30 minutes (until at least 96% of the N-(acetyl)-1-(4-piperidinyl)-2-(4-pyrimidinyl)-1-ethanone (5) was consumed, as measured by chromatography). A 10% NaOH solution (4.3 ml, 0.011 moles, 0.05 equivalents relative to moles of methyl pyrimidine (4) used in Part B) was added to adjust the pH to 7. The temperature of the mixture was then maintained at 50° C. for at least 30 minutes. Subsequently, the mixture was cooled to 10° C. over 1.5 hours, and then maintained at 10° C. for at least 4 hr. The solids were filtered, washed with 200 ml of water, and dried at 50° C. and at a pressure of no greater than 100 Torr to yield the product in the form of a pale orange solid. The hydrazone product existed as a mixture of tautomers and isomers in solution. Proton and carbon spectra were collected in deuteroacetonitrile solution. Most proton resonances are reported as multiplets, although fine structure was observed, since evidence existed that the tautomers were in equilibrium. Chemical shifts were referenced to the solvent. The product was characterized as follows: $^1$H NMR (CD$_3$CN, 500 MHz) δ 10.84 (1H, b), 9.00 (1H, d, J=1.33 Hz), 8.66 (1H, d, J=5.12 Hz), 7.79 (2H, m), 7.36 (3H, m), 4.24 (1H, d, J=13.3 Hz), 3.76 (3H, s), 3.68 (1H, d, J=13.6 Hz), 2.96 (1H, m), 2.53 (1H, m), 2.40 (1H, m), 2.36 (3H, s), 1.95 (3H, s), 1.61 (2H, m), 1.30 (1H, m), 1.15 (1H, m). $^{13}$C NMR (CD$_3$CN, 100 MHz) δ 169.40, 166.64, 159.73, 159.60, 158.84, 145.20, 137.11, 130.51, 130.51, 128.83, 128.83, 122.39, 46.57, 44.90, 41.52, 38.60, 30.39, 29.79, 21.69, 21.62. Anal. Calcd. For C$_{20}$H$_{25}$N$_5$O$_3$S: C, 57.81; H, 6.06; N, 16.85. Found: C, 57.67; H, 6.20; N, 16.84.

Part D. Preparation of 1-{4-[5-(4-chloro-phenyl)-4-pyrimidin-4-yl-1-(toluene-4-sulfonyl)-1H-pyrazol-3-yl]-piperidin-1-yl}-ethanone (9).

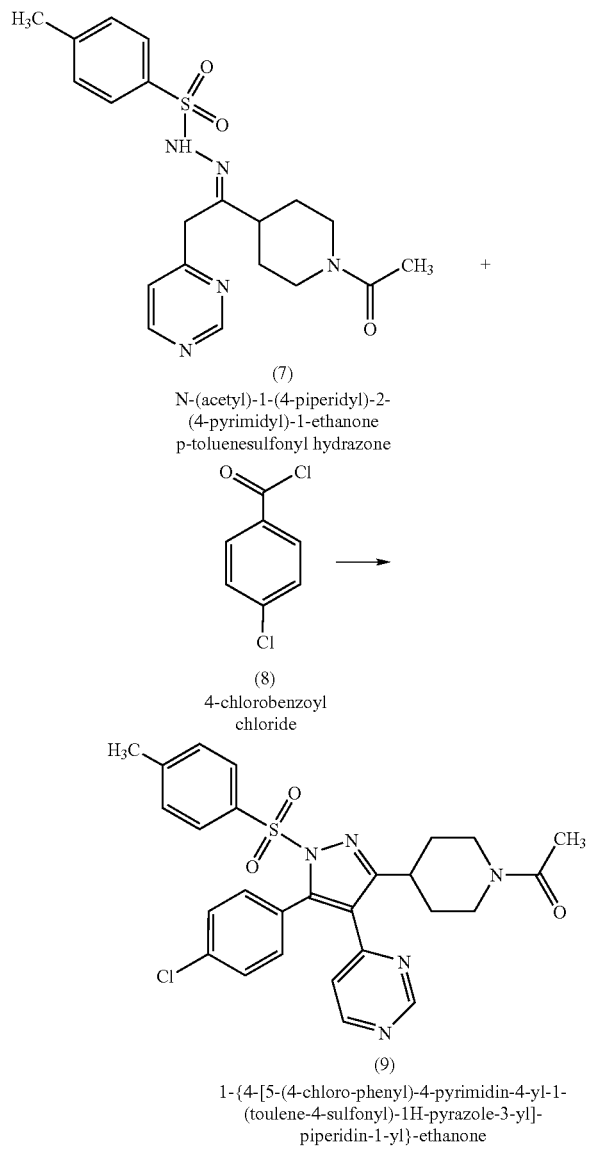

(7)
N-(acetyl)-1-(4-piperidyl)-2-(4-pyrimidyl)-1-ethanone p-toluenesulfonyl hydrazone (8)
4-chlorobenzoyl chloride (9)
1-{4-[5-(4-chloro-phenyl)-4-pyrimidin-4-yl-1-(toulene-4-sulfonyl)-1H-pyrazole-3-yl]-piperidin-1-yl}-ethanone This reaction was conducted in a 250 mL round bottom flask having a nitrogen inlet, addition funnel or condenser or distilling head with receiver, thermocouple, and magnetic stir bar. The reactor was first purged with nitrogen. Afterward, the N-acetyl hydrazone (7) from Part C (5.0 g, 0.0120 mole), 4-dimethylaminopyridine ("DMAP", 0.146 g, 0.0012 mole, 0.1 equivalents relative to moles of hydrazone (7), 99% purity, from Aldrich), and tetrahydrofuran ("THF", 20 ml, 4 ml per gram of hydrazone (7), from Aldrich) were charged to the reactor, and stirring was initiated. Triethylamine (1.70 g, 2.3 ml, 0.0168 moles, 1.4 equivalents relative to moles of hydrazone (7), 99% purity, from EM Science (Gibbstown, N.J.)) was then charged. Subsequently, the 4-chlorobenzoyl chloride (8) (2.59 g, 1.9 ml, 0.0148 moles, 1.23 equivalents relative to moles of hydrazone (7), 98% purity, from Aldrich) was charged neat at 25° C. over 15 mm. The reaction was exothermic, and increased the temperature to approximately 40° C. The resulting mixture was heated to reflux, and then maintained at reflux for at least 2 hr (until at least 98% of the N-acetyl hydrazone (7) was consumed, as measured by chromatography (remaining N-acetyl hydrazone (7) was calculated using the following formula: 100×(area % hydrazone/area % hydrazone+area % protected pyrazole)) at 254 nm)).

Part E. Preparation of 5-(4-piperidyl)-4-(4-pyrimidinyl)-3-(4-chlorophenyl)pyrazole (10).

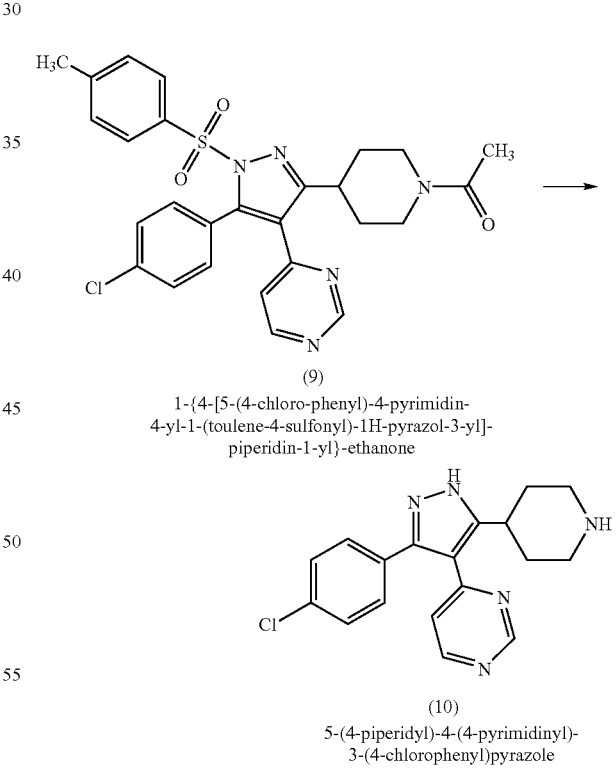

(9)
1-{4-[5-(4-chloro-phenyl)-4-pyrimidin-4-yl-1-(toulene-4-sulfonyl)-1H-pyrazol-3-yl]-piperidin-1-yl}-ethanone

(10)
5-(4-piperidyl)-4-(4-pyrimidinyl)-3-(4-chlorophenyl)pyrazole

This reaction also was conducted in the reactor of Part D. NaOH (2.92 g, 0.0722 moles, 99% purity) and water (20 ml) was then charged to the reaction mixture product of Part D.

The reactor was configured for distillation, and the solvents were removed while increasing the temperature until the reaction mixture reached 101° C. (THF distills at a vapor temperature of 65° C., followed by triethylamine at 89° C.). Afterward, the reactor was reconfigured for reflux. The mixture was then maintained at reflux for at least 4 hr (until at least 99% of the 1-{4-[5-(4-chloro-phenyl)-4-pyrimidin-4-yl-1-(toluene-4-sulfonyl)-1H-pyrazol-3-yl]-piperidin-1-yl}-ethanone (9) was consumed, as measured by chromatography). Water (20 ml) was then charged (to crystallize the 5-(4-piperidyl)-4-(4-pyrimidinyl)-3-(4-chlorophenyl)pyrazole product (10)). Subsequently, the mixture was cooled to less than 50° C., and 6N HCl (1.20 ml, 0.007 moles) was charged to the reactor to decrease the pH to 11–12. After the HCl addition, the mixture was further cooled to 5° C. and stirred for 1 hr. The solids were then filtered, washed with water, dried at a temperature of 80° C. and a pressure of 29 in. Hg to yield the product in the form of an off-white solid.

Part F. Preparation of N-(2-hydroxyacetyl)-5-(4-piperidyl)-4-(4-pyrimidinyl)-3-(4-chlorophenyl)pyrazole (12).

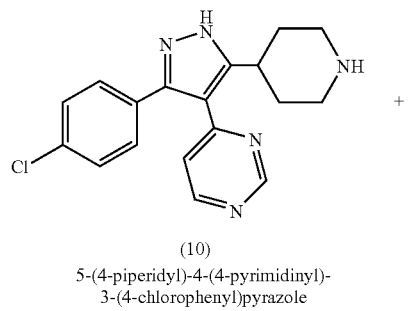

(10)
5-(4-piperidyl)-4-(4-pyrimidinyl)-
3-(4-chlorophenyl)pyrazole

+

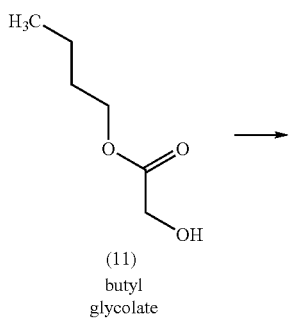

(11)
butyl
glycolate

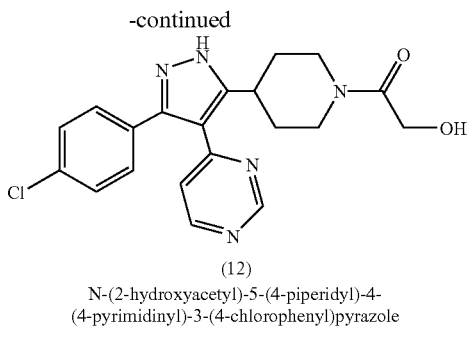

(12)
N-(2-hydroxyacetyl)-5-(4-piperidyl)-4-
(4-pyrimidinyl)-3-(4-chlorophenyl)pyrazole This reaction was conducted in a round bottom flask reactor equipped with a half-moon shaped paddle, thermocouple, oil bath, condenser, and nitrogen adapter. The reaction was monitored using HPLC. 5-(4-piperidyl)-4-(4-pyrimidinyl)-3-(4-chlorophenyl)pyrazole (10) (60 g, 0.177 moles) from Part E, butyl glycolate (11) (59.97 g, 58.86 ml, 0.454 moles, 2.57 equivalents relative to moles of butyl glycolate (11), 95% purity, from Fluka), 1,8-diazabicyclo[5.4.0]undec-7-ene ("DBU", 2.69 g, 2.64 ml, 0.01 moles, 0.1 equivalents relative to moles of butyl glycolate (11), 98% purity, from Aldrich), and xylenes (180 ml, ≧98.5% purity, from Aldrich) were charged to the reactor. This resulted in a very thick slurry. Mixing was slowly initiated, and then increased gradually while also initiating heating. The mixture was heated to reflux (135–140° C.), and then maintained at reflux for 4 h while monitoring the reaction using HPLC. After conversion of the ceased 5-(4-piperidyl)-4-(4-pyrimidinyl)-3-(4-chlorophenyl)pyrazole (10) (when only 2–4 area % of the 5-(4-piperidyl)-4-(4-pyrimidinyl)-3-(4-chlorophenyl)pyrazole (10) remains), the mixture was cooled to 100° C. 1-BuOH (120 ml, 99.8%, HPLC grade, Aldrich) was then charged to the reactor. The resulting mixture was heated at 125° C. for 5 min, and then cooled to 25° C. The resulting solids were isolated by filtration using a fritted funnel, and the mother liquor was used to aid in removal of the slurry from the reactor. The resulting solids were washed (in a displacement wash) with ethyl acetate (180 ml) twice, keeping the washes separate (the mother liquor was brown, the first wash contained some color, and the second was nearly clear). Afterward, the solids were air dried on the filter to yield product in ~92–94% yield. HPLC area % >98–99%. The above HPLC monitoring was carried out using an HP 1100 system and the following gradient: 80% water/acetonitrile to 100% acetonitrile (in 8 min then hold for 2 min with 100% acetonitrile) with both water and acetonitrile containing 0.1% TFA. The column used was a Zorbax XDB-C8 column (part #993967.906; 4.6 mm×15 cm). The column temperature was 50° C. The wavelength used was 254 nm. Samples were typically prepared by adding one drop to 1 ml of methanol/methylene chloride solution (1:1 by volume).

Example 4

Alternative Preparation and Isolation of N-(acetyl)-1-(4-piperidyl)-2-(4-pyrimidyl)-1-ethanone (5)

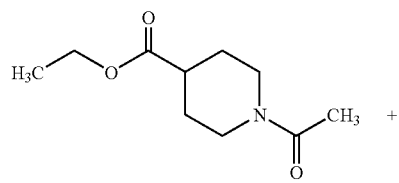

(3)
ethyl
N-(acetyl)
isonipecotate

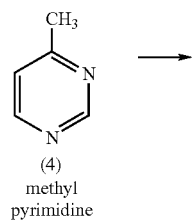

(4)
methyl
pyrimidine

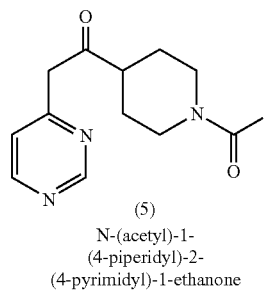

(5)
N-(acetyl)-1-
(4-piperidyl)-2-
(4-pyrimidyl)-1-ethanone

This reaction was carried out in a 400 ml jacketed reactor. Potassium t-butoxide (28.5 g, 241 mmol) and anhydrous tetrahydrofuran ("THF", 226 ml) were charged to the reactor. The mixture was stirred and cooled to −6° C. 4-methylpyrimidine (4) (9.9 g, 105 mmol) was charged to the reactor over 10 min. When the addition was approximately 75% complete, a yellow solid precipitated and the temperature briefly rose to −4° C. After stirring the suspension at −6° C. for 1 hr, N-acetyl ethyl isonipecotate (3) (20.9 g) was charged and the mixture was stirred for 19 hr at −6° C. The resulting dark brown suspension was warmed to 0° C., and 80 mL of 3 M HCl was added over 20 min. The temperature rose to 9° C. during the addition, and the color of the mixture became yellow. The mixture was stirred at 25° C. for 2 hr. Afterward, water (10 ml) was added, the temperature was increased to 30° C. The resulting mixture was extracted with one 100 mL and one 50 mL portion of toluene. The combined organic phase was partially concentrated via distillation at atmospheric pressure to remove most of the THF. When the batch temperature reached 95° C., the mixture was cooled, and distillation was continued at approximately 160 Torr until the volume of the concentrate was approximately 75 ml. The solution was then cooled to 0° C., and stirred for 4 hr to crystallize the product. The product was filtered, and the cake was washed with a small amount of heptane. Drying produced 11.4 g of 1-(1-acetylpiperidin-4-yl)-2-pyrimidin-4-ylethanone (44% yield) as a yellow solid, HPLC-APCI/MS m/z: M+1 248.2 (100). The compound existed as a mixture of enol and ketone tautomers in deuterochloroform: $^1$H NMR (300 MHz, CDCl$_3$, δ): 14.6 (br s, 0.65H), 9.16 (s, 0.35H), 8.77 (s, 0.65H), 8.70 (d, J=5.2 Hz, 0.35H), 8.39 (d, J=5.6 Hz, 0.65H), 7.29 (d, J=5.2 Hz, 0.35H), 6.82 (d, J=5.6 Hz, 0.65H), 5.31 (s, 0.65H), 4.72 (m, 0.65H), 4.57 (m, 0.35H), 3.97 (s, 1H), 3.88 (m, 0.65H), 3.13 (m, 1H), 2.56–2.85 (m, 1.35H), 2.44 (m, 0.65H), 2.12 (s, 2H), 2.10 (m, 2H), 1.50–1.75 (m, 2H).

Example 5

Alternative Preparation and Isolation of 1-{4-[5-(4-chlorophenyl)-4-pyrimidin-4-yl-1-(toluene-4-sulfonyl)-1H-pyrazole-3-yl]-piperidine-1-yl}-ethanone (9)

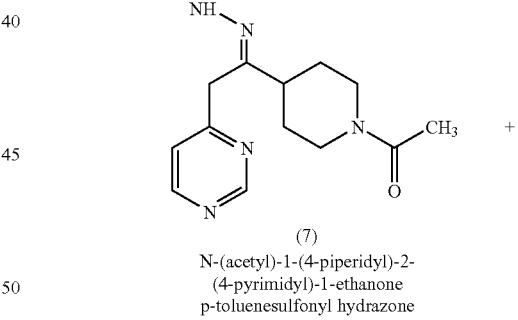

(7)
N-(acetyl)-1-(4-piperidyl)-2-
(4-pyrimidyl)-1-ethanone
p-toluenesulfonyl hydrazone

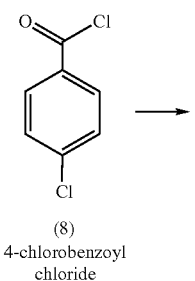

(8)
4-chlorobenzoyl
chloride

-continued

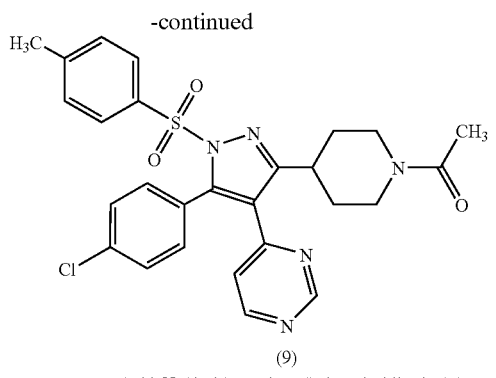

(9)
1-{4-[5-(4-chloro-phenyl)-4-pyrimidin-4-yl-1-(toulene-4-sulfonyl)-1H-pyrazole-3-yl]-piperidin-1-yl}-ethanone This reaction was carried out in a 100 ml round bottom flask. N'-[(1E)-1-(1-acetylpiperidin-4-yl)-2-pyrimidin-4-ylethylidene]-4-methylbenzenesulfonohydrazide (7) (5g, 11 mmol) was charged to the reactor, followed by tetrahydrofuran ("THF", 31 ml), which, in turn, was followed by 2.15 ml of triethylamine ("TEA", 2.15 ml) and 4-dimethylaminopyridine ("DMAP", 0.134 g). 4-Chlorobenzoyl chloride (8) ("4-CBC", 2.09 ml) was then charged all at once while stirring the mixture. The reaction was brought to reflux. Liquid chromatography indicated that the reaction was complete in just over 1 hr. The solution was washed with saturated ammonium chloride (2×25 ml), and the THF was removed in vacuo to yield a yellow oil (11.18 g), which solidified upon sitting. Recrystallization from ethanol/water yielded 4.88 g of a white powder (76% yield). The product had the following characteristics: $^1$H NMR (CDCl$_3$, 300 MHz) δ 9.20 (1H, s), 7.63 (2H, d, J=8.4 Hz), 7.45 (2H, d, J=8.4 Hz), 7.30 (2H, d, J=8.1 Hz), 7.29 (1H, s), 7.21 (2H, d, J=8.4 Hz), 6.64 (1H, d, J=5.1 Hz), 4.71–4.52 (1H, m), 4.01–3.82 (1H, m), 3.59–3.44 (1H, m), 3.28–3.08 (1H, m), 2.84–2.58 (1H, m), 2.46 (3H, s), 2.16 (3H, s), 2.02–1.62 (4H, m). $^{13}$C NMR (CDCl$_3$, 75 MHz) δ 169.11, 158.91, 146.39, 136.80, 134.55, 132.01, 130.13, 129.19, 126.72, 34.91, 31.15, 22.01, 21.69.

Example 6

Preparation and Isolation of 4-[3-(1-acetylpiperidin-4-yl)-5-(4-chlorophenyl)-1H-pyrazol-4-yl]pyrimidine (10A)

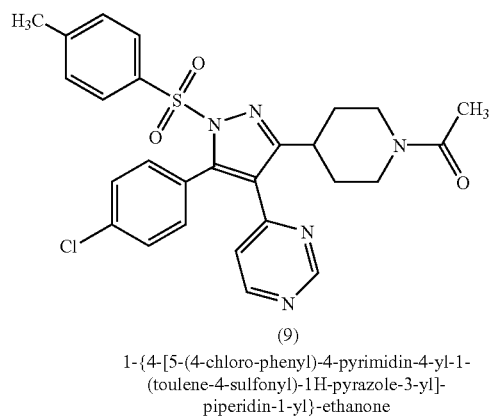

(9)
1-{4-[5-(4-chloro-phenyl)-4-pyrimidin-4-yl-1-(toulene-4-sulfonyl)-1H-pyrazole-3-yl]-piperidin-1-yl}-ethanone

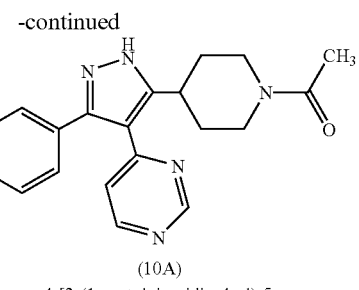

(10A)
4-[3-(1-acetylpiperidin-4-yl)-5-(4-chlorophenyl)-1H-pyrazol-4yl]pyrimidine This reaction was carried out in a 50 ml round bottom flask. 4-{3-(1-Acetylpiperidin-4-yl)-5-(4-chlorophenyl)-1-[(4-methylphenyl)sulfonyl]-1H-pyrazole-4-yl}pyrimidine (9) (0.5 g) charged to the reactor, followed by ethanol (5 ml), which, in turn, was followed by potassium carbonate (1 g). The mixture was stirred until completion of the reaction, as indicated by liquid chromatography. The ethanol was then removed in vacuo, and the resulting solid was dissolved in ethyl acetate. The organic layer washed with water, and concentrated in vacuo to yield a white solid. The product had the following characteristics: $^1$H NMR (CDCl$_3$, 300 MHz) δ 9.27 (1H, s), 8.54 (1H, broad-s), 7.36 (4H, s), 7.01 (1H, d, J=5.1 Hz), 4.82–4.72 (1H, m), 4.02–3.90 (1H, m), 3.72–3.59 (1H, m), 3.30–3.18 (1H, m), 2.79–2.62 (1H, m), 2.18 (3H, s), 2.15–1.78 (4H, m).

Example 7

Alternative Preparation of 5-(4-piperidyl)-4-(4-pyrimidinyl)-3-(4-chlorophenyl)pyrazole (10) Using Acidic Deprotection

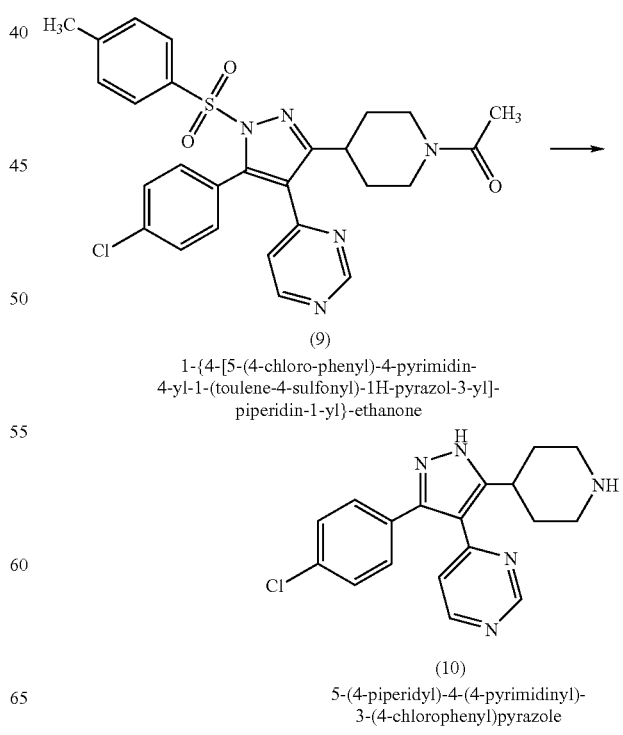

This reaction was conducted in a 250 ml round bottom flask. To 4-{3-(1-acetylpiperidin-4-yl)-5-(4-chlorophenyl)-1-[(4-methylphenyl)sulfonyl]-1H-pyrazole-4-yl}pyrimidine (9) (6.86 g) was added 6 M HCl (40 ml). The mixture was stirred and heated to reflux. The reaction was monitored by HPLC, and determined to be complete after 2.5 hr. The mixture was then cooled in an ice/water bath, and 6 M NaOH was slowly added until the pH was between 13–14. The resulting product was isolated via vacuum filtration to yield 3.25 g of 4-[3-(4-chlorophenyl)-5-piperidine-4-yl-1H-pyrazol-4-yl]pyrimidine (79.8% yield) as a white solid.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A process for making a substituted pyrazole, a tautomer of the substituted pyrazole, or a salt of the substituted pyrazole or tautomer, wherein:

the substituted pyrazole corresponds in structure to Formula (I):

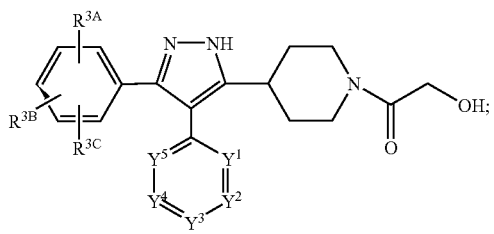

(I)

and the process comprises combining an isonipecotate with an anhydride; and the isonipecotate corresponds in structure to Formula (VI):

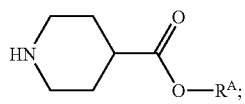

(VI)

and the anhydride corresponds in structure to Formula (V):

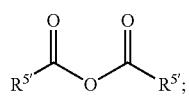

(V)

and $R^A$ is alkyl; and $R^{3A}$, $R^{3B}$, and $R^{3C}$ are independently selected from the group consisting of hydrogen, halogen, hydroxy, cyano, amino, alkyl, aminoalkyl, monoalkylamino, dialkylamino, alkoxy, and alkoxyalkyl, wherein:

any carbon of the alkyl, aminoalkyl, monoalkylamino, dialkylamino, alkoxy, or alkoxyalkyl optionally is substituted with one or more substituents independently selected from the group consisting of halogen, hydroxy, and cyano; and one of $Y^1$, $Y^2$, $Y^3$, $Y^4$, and $Y^5$ is =C($R^4$)—; and one of $Y^1$, $Y^2$, $Y^3$, $Y^4$, and $Y^5$ is =N—; and three of $Y^1$, $Y^2$, $Y^3$, $Y^4$, and $Y^5$ are independently selected from the group consisting of =C(H)— and =N—; and $R^4$ is selected from the group consisting of hydrogen, halogen, cyano, hydroxy, thiol, carboxy, nitro, alkyl, carboxyalkyl, alkylthio, alkylsulfinyl, alkylsulfonyl, alkylcarbonyl, carbocyclyl, carbocyclylalkyl, carbocyclylalkenyl, carbocyclyloxy, carbocyclylalkoxy, carbocyclyloxyalkyl, carbocyclylthio, carbocyclylsulfinyl, carbocyclylsulfonyl, heterocyclylthio, heterocyclylsulfinyl, heterocyclylsulfonyl, carbocyclylalkoxy, carbocyclylheterocyclyl, heterocyclylalkyl, heterocyclyloxy, heterocyclylalkoxy, amino, aminoalkyl, alkylamino, alkenylamino, alkynylamino, carbocyclylamino, heterocyclylamino, aminocarbonyl, alkoxy, alkoxyalkyl, alkenyloxyalkyl, alkoxyalkylamino, alkylaminoalkoxy, alkoxycarbonyl, carbocyclyloxycarbonyl, heterocyclyloxycarbonyl, alkoxycarbonylamino, alkoxycarbocyclylamino, alkoxycarbocyclylalkylamino, aminosulfinyl, aminosulfonyl, alkylsulfonylamino, alkoxyalkoxy, aminoalkoxy, aminoalkylamino, alkylaminoalkylamino, carbocyclylalkylamino, alkylaminoalkylaminoalkylamino, alkylheterocyclylamino, heterocyclylalkylamino, alkylheterocyclylalkylamino, carbocyclylalkylheterocyclylamino, heterocyclylheterocyclylalkylamino, alkoxycarbonylheterocyclylamino, alkylaminocarbonyl, alkylcarbonylamino, hydrazinyl, alkylhydrazinyl, and carbocyclylhydrazinyl, wherein:

any substitutable member of such group optionally is substituted with one or more substituents independently selected from the group consisting of alkyl, alkenyl, hydroxy, halogen, haloalkyl, alkoxy, haloalkoxy, keto, amino, nitro, cyano, alkylsulfonyl, alkylsulfinyl, alkylthio, alkoxyalkyl, carbocyclyloxy, heterocyclyl, and heterocyclylalkoxy; and $R^{5'}$ is selected from the group consisting of $R^{5A}$ and —O—$R^{5B}$; and $R^{5A}$ is selected from the group consisting of hydrogen, optionally-substituted alkyl, optionally-substituted aryl, and optionally-substituted heteroaryl; and $R^{5B}$ is selected from the group consisting of optionally-substituted alkyl (except for unsubstituted tert-butyl), optionally-substituted alkenyl, optionally-substituted aryl, optionally-substituted arylalkyl, optionally-substituted heteroaryl, and optionally-substituted heteroarylalkyl.

2. A process according to claim 1, wherein:

$R^{5A}$ is selected from the group consisting of alkyl, aryl, and heteroaryl; and $R^{5B}$ is selected from the group consisting of alkyl (except for tert-butyl), alkenyl, aryl, arylalkyl, heteroaryl, and heteroarylalkyl.

3. A process according to claim 1, wherein $R^{5'}$ is methyl.

4. A process according to claim 1, wherein $R^{5'}$ is ethyl.

5. A process according to claim 1, wherein $R^{5'}$ is phenyl.

6. A process according to claim 1, wherein:

$R^5$ is —O—$R^{5B}$, and
$R^{5B}$ is selected from the group consisting of isobutyl, trichioroethyl, allyl, phenyl, and benzyl.

7. A process according to claim 1, wherein $R^4$ is ethyl.

8. A process according to claim 7, wherein the substituted pyrazole corresponds in structure to the following formula:

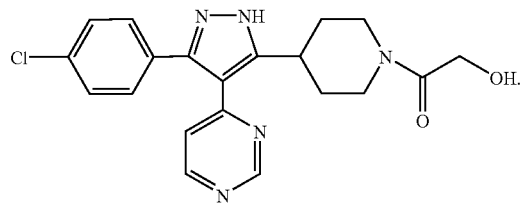

* * * * *